United States Patent
Bolduc et al.

(12)

(10) Patent No.: US 6,280,460 B1
(45) Date of Patent: *Aug. 28, 2001

(54) DEVICES AND METHODS FOR PERFORMING VASCULAR ANASTOMOSIS

(75) Inventors: Lee R. Bolduc, Mountain View; James R. Gannoe, Redwood City; Theodore C. Johnson, Atherton, all of CA (US)

(73) Assignee: Heartport, Inc., Redwood City, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/023,876

(22) Filed: Feb. 13, 1998

(51) Int. Cl.[7] .................................................. A61B 17/06

(52) U.S. Cl. ........................................ 606/222; 606/144

(58) Field of Search ........................... 606/222, 144–159, 606/123–126, 223, 224, 228, 139

(56) References Cited

U.S. PATENT DOCUMENTS

| | | |
|---|---|---|
| 1,251,258 | 12/1917 | Magill . |
| 1,918,890 | 7/1933 | Bacon . |
| 2,434,030 | 1/1948 | Yeomans . |

(List continued on next page.)

FOREIGN PATENT DOCUMENTS

| | | |
|---|---|---|
| 0137685 | 4/1985 | (EP) . |
| 2108418 | 5/1986 | (GB) . |
| 7711347 | 4/1979 | (NL) . |
| 1097301 | 6/1984 | (SU) . |

OTHER PUBLICATIONS

Vogelfanger et al., "A Concept of Automation in Vascular Surgery: A Preliminary Report on a Mechanical Instrument for Arterial Anastomosis," *Can J. Surg*, Apr. 1958; 1;262–265.

Inokuchi, "A New Type of Vessel–Suturing Apparatus," *AMA Archives of Surgery*, Dec. 1958; 77:954–957.

Inokuchi, "Stapling Device for End–to–side Anastomosis of Blood Vessels," *AMA Archives of Surgery*, Mar. 1961; 82:337–341

(List continued on next page.)

*Primary Examiner*—Michael Buiz
*Assistant Examiner*—Lien Ngo
(74) *Attorney, Agent, or Firm*—Jens E. Hoekendijk

(57) ABSTRACT

Devices and methods for performing vascular anastomosis. A needle passer is used to pass one or more needles through tissue to thread one or more lengths of suture through the tissue. The needle passer is operable using one hand and includes a handle supporting a shaft assembly carrying first and second sets of needles connected by lengths of suture. An actuator assembly uncovers the first set of needles, moves them into a radially extended position, and then passes them through tissue, for example, the wall of a patient's aorta. The needle passer may be pistol-shaped with a trigger that is moved in one direction to sequentially uncover, radially extend, and move the first set of needles through the aorta around an aortotomy. The needles may then be pulled away from the patient to thread the suture through the tissue. A delivery device is used to deliver a member adapted to be secure to body tissue, such as a vascular conduit. The delivery device includes a shaft and a collar mounted for relative movement. The shaft supports a vascular conduit so that an end of the conduit is disposed against the collar. A sealing element may be positioned on the collar beneath the end of the conduit. The needles in the second set are removed from the needle passer and are placed through the conduit and sealing element and into the collar. The shaft is then moved through the collar to move the vascular conduit along the suture into contact with the aorta. The delivery device is then removed and the respective ends of each suture length secured to fix the end of the vascular conduit to the aorta.

22 Claims, 45 Drawing Sheets

U.S. PATENT DOCUMENTS

| | | |
|---|---|---|
| 2,638,901 | 5/1953 | Sugarbaker . |
| 2,707,783 | 5/1955 | Sullivan . |
| 3,040,748 | 6/1962 | Klein et al. . |
| 3,080,564 | 3/1963 | Strekopitov et al. . |
| 3,193,165 | 7/1965 | Akhalaya et al. . |
| 3,217,557 | 11/1965 | Martinot . |
| 3,252,643 | 5/1966 | Strepkopytov et al. . |
| 3,254,650 | 6/1966 | Collito . |
| 3,254,651 | 6/1966 | Collito . |
| 3,269,630 | 8/1966 | Fleicher . |
| 3,388,847 | 6/1968 | Kasulin et al. . |
| 3,452,615 | 7/1969 | Gregory . |
| 3,494,533 | 2/1970 | Green et al. . |
| 3,519,187 | 7/1970 | Kapitanov . |
| 3,552,626 | 1/1971 | Astafiev et al. . |
| 3,589,589 | 6/1971 | Akopov . |
| 3,593,903 | 7/1971 | Astafiev et al. . |
| 3,638,652 | 2/1972 | Kelley . |
| 3,692,224 | 9/1972 | Astafiev et al. . |
| 3,774,615 | 11/1973 | Lim et al. . |
| 3,805,793 | 4/1974 | Wright . |
| 4,166,466 | 9/1979 | Jarvik . |
| 4,304,236 | 12/1981 | Conta et al. . |
| 4,319,576 | 3/1982 | Rothfuss . |
| 4,325,376 | 4/1982 | Klieman et al. . |
| 4,350,160 | 9/1982 | Kolesov et al. . |
| 4,352,358 | 10/1982 | Angelchik . |
| 4,366,819 | 1/1983 | Kaster . |
| 4,368,736 | 1/1983 | Kaster . |
| 4,505,414 | 3/1985 | Filipi . |
| 4,523,592 | 6/1985 | Daniel . |
| 4,553,542 | 11/1985 | Schenck et al. . |
| 4,573,468 | 3/1986 | Conta et al. . |
| 4,576,167 | 3/1986 | Noiles . |
| 4,586,503 | 5/1986 | Kirsch et al. . |
| 4,593,693 | 6/1986 | Schenck . |
| 4,603,693 | 8/1986 | Conta et al. . |
| 4,607,637 | 8/1986 | Berggren et al. . |
| 4,624,255 | 11/1986 | Schenck et al. . |
| 4,646,745 | 3/1987 | Noiles . |
| 4,657,019 | 4/1987 | Walsh et al. . |
| 4,665,906 | 5/1987 | Jervis . |
| 4,703,887 | 11/1987 | Clanton et al. . |
| 4,747,407 | 5/1988 | Liu et al. . |
| 4,907,591 | 3/1990 | Vasconcellos et al. . |
| 4,917,087 | 4/1990 | Walsh et al. . |
| 4,917,090 | 4/1990 | Berggren et al. . |
| 4,917,091 | 4/1990 | Berggren et al. . |
| 4,957,499 | 9/1990 | Lepstove et al. . |
| 5,119,983 | 6/1992 | Casen et al. . |
| 5,197,649 | 3/1993 | Bessler et al. . |
| 5,234,447 | 8/1993 | Kaster et al. . |
| 5,242,457 | 9/1993 | Akopov et al. . |
| 5,271,543 | 12/1993 | Grant et al. . |
| 5,292,053 | 3/1994 | Bilotti et al. . |
| 5,320,632 * | 6/1994 | Heidmueller ................ 606/144 |
| 5,324,447 | 6/1994 | Lam et al. . |
| 5,333,773 | 8/1994 | Main et al. . |
| 5,336,233 | 8/1994 | Chen . |
| 5,348,259 | 9/1994 | Blanco et al. . |
| 5,366,462 | 11/1994 | Kaster et al. . |
| 5,368,601 * | 11/1994 | Sauer et al. ................ 606/144 |
| 5,478,354 | 12/1995 | Tovey et al. . |
| 5,522,834 | 6/1996 | Fonger et al. . |
| 5,549,619 | 8/1996 | Peters et al. . |
| 5,554,162 | 9/1996 | DeLange . |

OTHER PUBLICATIONS

Narter et al., "An Experimental Method for Nonsuture Anastomosis of the Aorta," *Surg Gyne & Obs*, 1964; 362–364.

Androsov, "The New Method of Surgical Treatment of Blood Vessel Lesions," *Arch. Surg*, 1956;73:262–265.

Inokuchi, "A New Type of Vessel–suturing Apparatus," *AMA Arch Surg*, 1958;77:954–957.

Holt et al., "A New Technique for End–to–end Anastomosis of Small Arteries," Surg Forum, 1960;11:242.

Rohman et al., Chapter IX—Cardiovascular Technique, "Double Coronary Artery–internal Mammary Artery Anastomoses, Tantalum Ring Technique," *Surg Forum*, 1960;11:236–243.

Goetz et al., "Internal Mammary–coronary Artery Anastomosis: A Nonsuture Method Employing Tantalum Rings," *J Thorac Card Surg*, 1961;41(3):378–386.

Gottlob et al., "Anastomoses of Small Arteries and Veins by Means of Bushings and Adhesive," *J Card Surg*, 1968;9:337–341.

Guyton et al., "A Mechanical Device for Sutureless Aorta—Saphenous Vein Anastomosis," *Ann Thorac Surg*, 1979;28:342–345.

Gentili et al., "A Technique for Rapid Non–suture Vascular Anastomosis," *Can J Neuro Sci*, 1987;14(1):92–95.

Olearchyk, "Vasilii I. Kolesov—A Pioneer of Coronary Revascularization by Internal Mammary–coronary Artery Grafting," *J Thorac Surg*, 1988;96(1):13–18.

Ragnarsson et al,. "Arterial End–to–side Anastomosis with the UNILINK System," *Ann Plastic Surg*, 1989;22(3):405–415.

Ragnarsson et al, "Microvenous End–to–side Anastomosis: An experimental Study Comparing the UNILINK System and Sutures," *J Reconstruct Microsurg*, 1989;5(3):217–224.

Li et al., "End–to–side–anastomosis in the Dog Using the 3M Precise Microvascular Anastomotic System: A Comparative Study," *J Reconstruct Microsurg*, 1991;7(4):345–350.

Kirsch et al., "A New Method for Microvascular Anastomosis: Report of Experimental and Clinical Research," *American Surgeon*, 1992;58:722–727.

Lanzetta et al., "Long–term Results of 1 Millimeter Arterial Anastomosis Using the 3M Precise Microvascular Anastomotic System," *Microsurgery*, 1992;13:313–320.

Nakayama et al., "A Simple New Apparatus for Small Vessel Anastomosis (free autograft of the sigmoid included)," *Surgery*, 1962;52(6):918–931.

Berggren et al., "Clinical Experience with UNLINK 3M Precise Microvascular Anastomotic Device," *Scand J Plast Reconstr Hand Surg*, 1993;27:35–39.

* cited by examiner

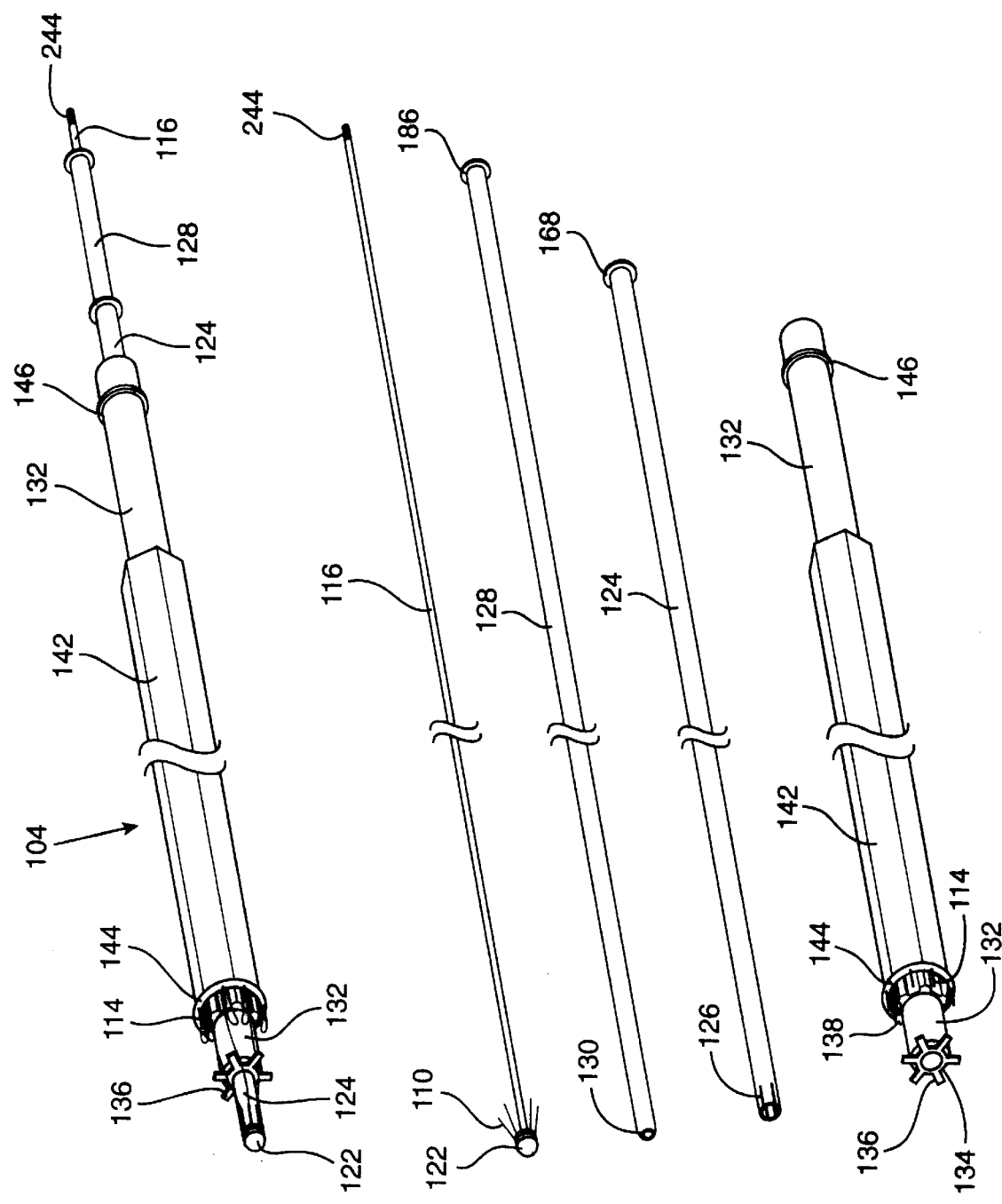

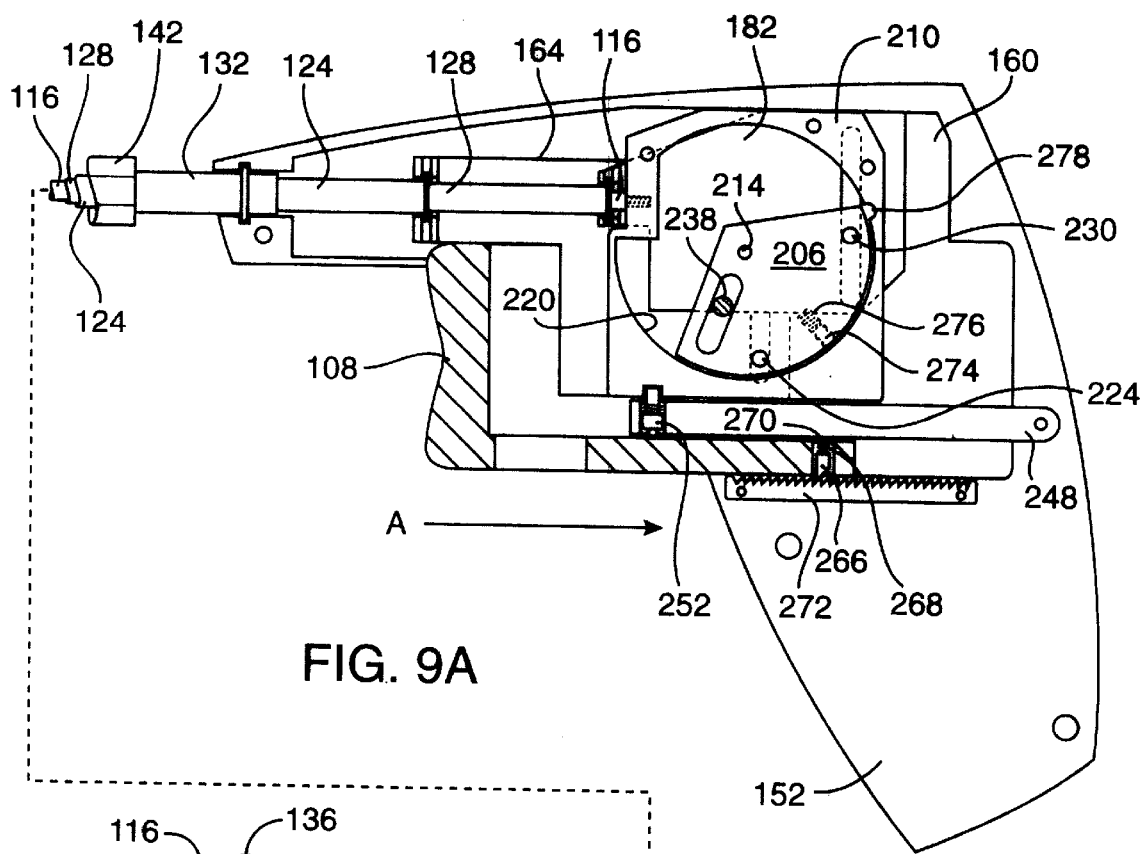
FIG. 9A
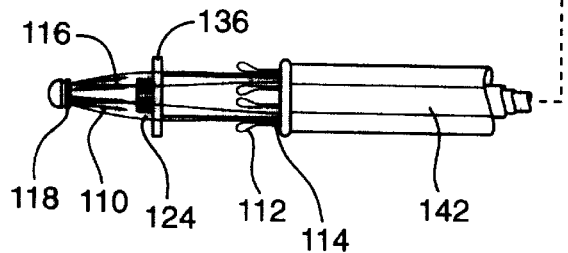
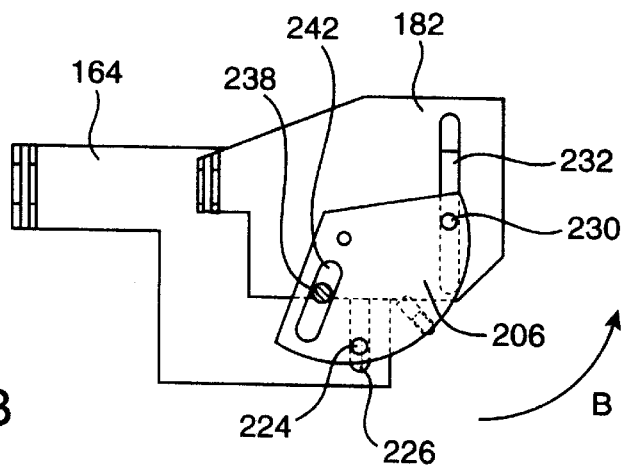
FIG. 9B

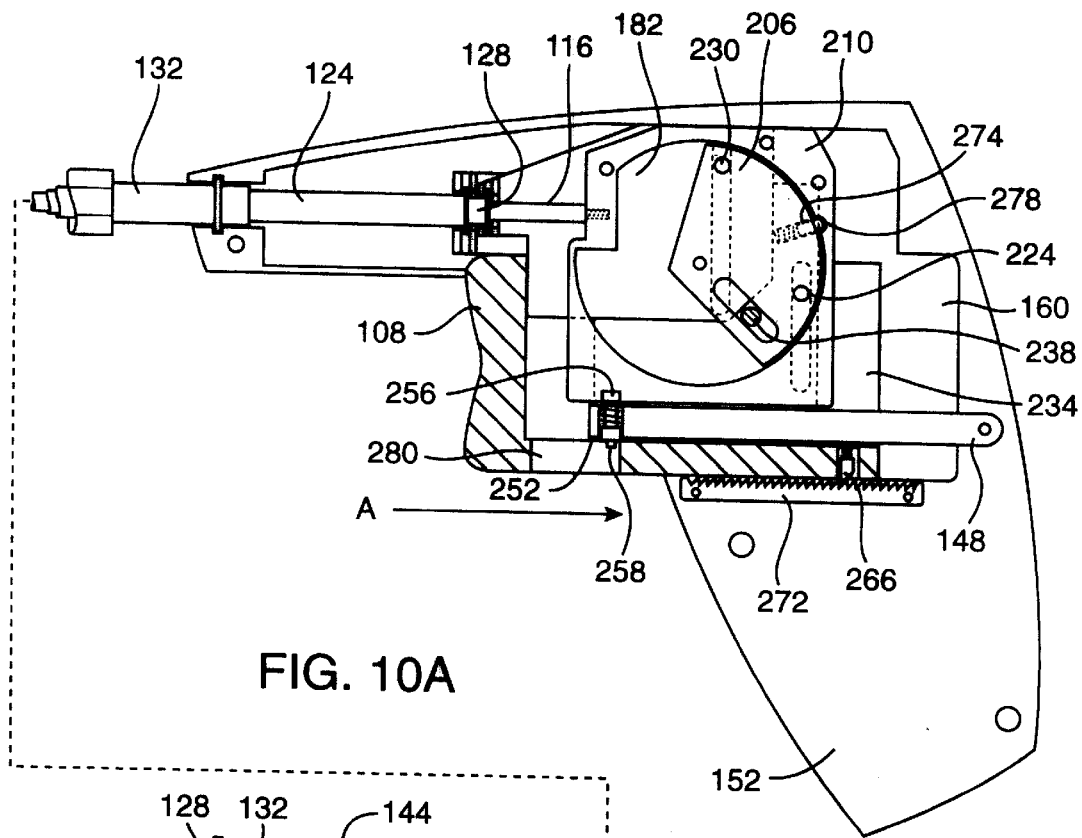
FIG. 10A
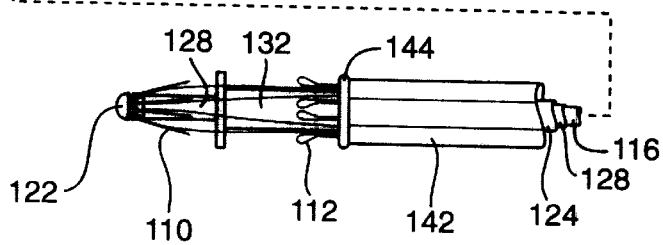
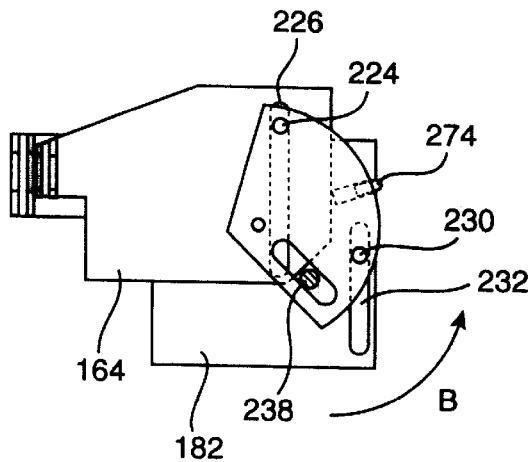
FIG. 10B

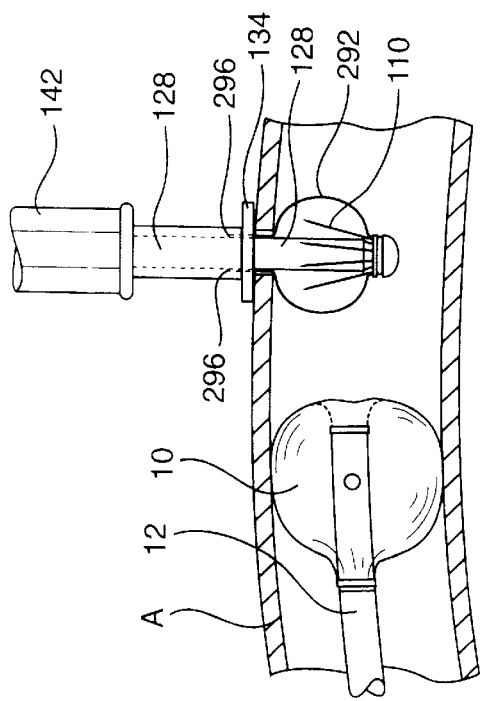
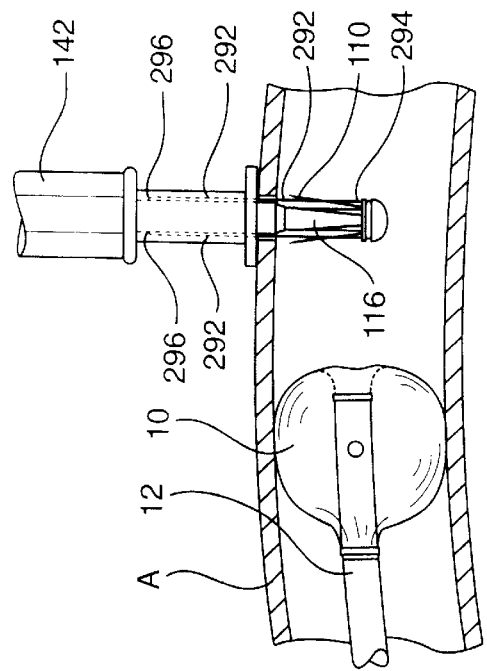
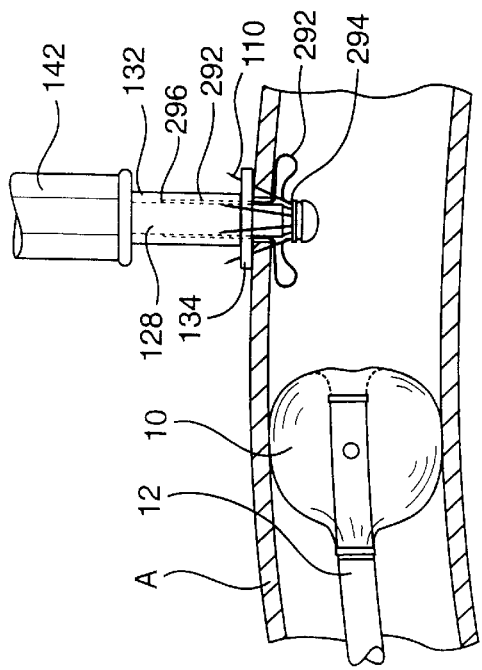
FIG. 21A
FIG. 21B
FIG. 21C

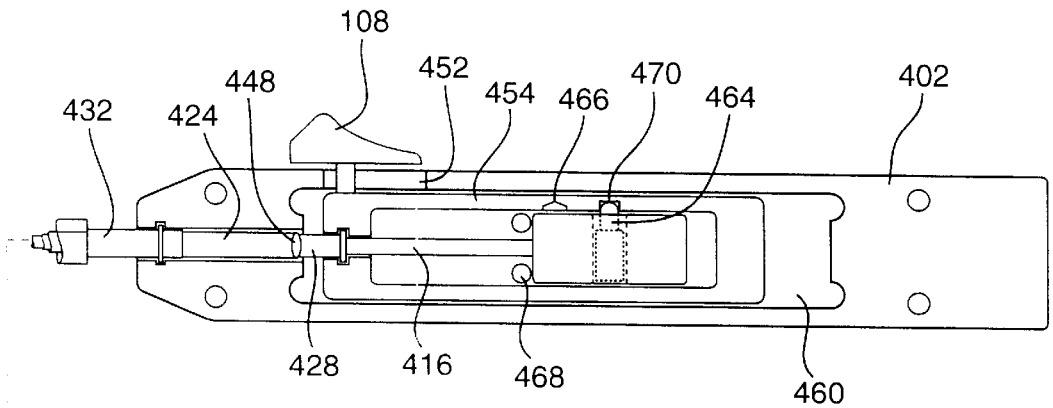
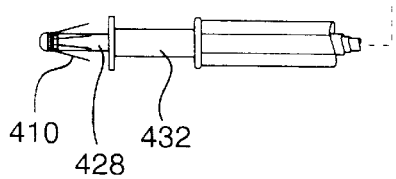
FIG. 37C
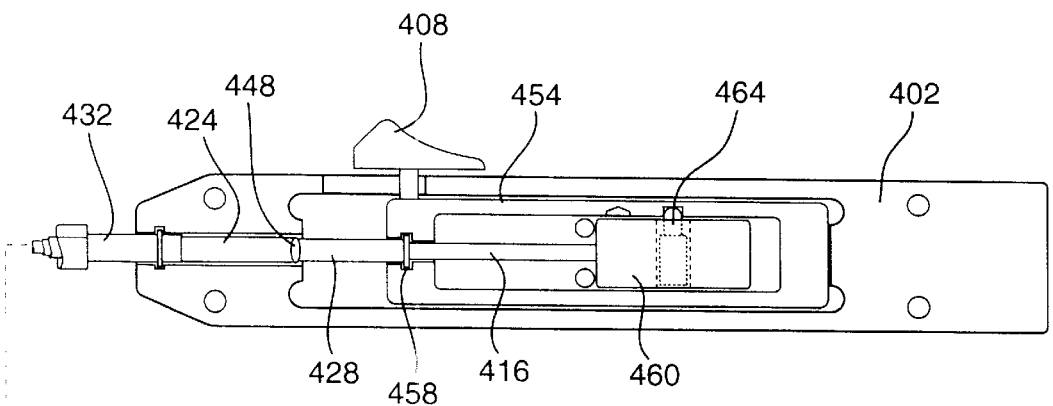
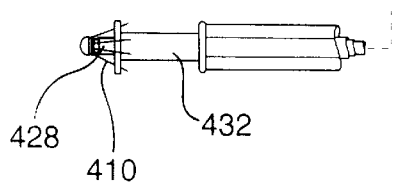
FIG. 37D

DEVICES AND METHODS FOR PERFORMING VASCULAR ANASTOMOSIS

BACKGROUND OF THE INVENTION

1. Field of the Invention

The invention relates primarily to devices and methods for performing an anastomosis between a vascular conduit, such as a vein, artery or artificial blood vessel, and a hollow body structure, such as a patient's aorta. The invention, however, will find use in various other applications, including, for example, repairing atrial or ventricular septal defects, patent ductis arteriosus, or closing vascular punctures, such as those created during catheterization of a patient in order to perform angioplasty, stenting or other endovascular procedures.

2. Description of Related Art

Many devices and methods have been proposed for performing an anastomosis (graft) between blood vessels. One of the most common surgical procedures carried out today which requires performing an anastomosis is coronary artery bypass grafting (CABG), commonly referred to as bypass surgery. This procedure is used to treat patients suffering from coronary disease in the form of one or more coronary arteries that are partially or completely blocked by stenoses. When blood flow through the coronary arteries is restricted or occluded, the cardiac muscle tissue becomes deprived of adequate blood flow, which eventually results in death of the muscle tissue. Interventional procedures other than bypass surgery, for example, angioplasty and atherectomy, are also used to treat occluded coronary arteries. However, bypass surgery is usually desirable or necessary to treat patients suffering from severe or multiple coronary artery blockages, or when other interventional procedures have been or would likely be unsuccessful.

In order to bypass a blockage in a coronary artery, the surgeon must anastomose a vascular conduit which is in communication with a source of arterial blood to the coronary artery at a location downstream of the blockage. The vascular conduit may be a native artery carrying blood from the patient's heart, for example, the right or left internal mammary artery (IMA). In such case, the artery may be transected from the patient's body to provide a free end which is prepared for distal anastomosis to the coronary artery. Alternatively, the IMA may be transected and removed from the body and one end prepared for anastomosis to an arterial blood source and the other to a coronary artery. Further, depending on the number of coronary arteries which are blocked, in addition to using the right and/or left IMA, other vascular conduits may be needed. One end of each conduit is prepared for distal anastomosis to the coronary artery, while the other end is prepared for proximal anastomosis to an arterial blood source, for example, the aorta. The vascular conduits may be harvested from the patient's body, suitable examples of which include the left or right IMA, inferior epigastric artery, splenic artery, subclavian artery, saphenous vein, etc. Also, animal or synthetic vascular conduits may be used instead of or in addition to those mentioned above.

The most common form of bypass surgery involves bypassing blockages in multiple coronary arteries, e.g., quadruple, five or six-way bypass procedures. As a result, most bypass procedures require a number of vascular conduits to form the necessary anastomoses. However, there is a limited number of native arterial conduits available which may be used by simply attaching one end to a blocked coronary artery. As such, it is usually necessary to use free conduits or grafts, which requires forming an anastomosis at both ends of each conduit, one end to an arterial blood source and the other end to the blocked coronary artery. The patient's aorta is a desirable arterial blood source to which the proximal end of one or more conduits may be anastomosed. As is the case with all other anastomoses, the surgeon must securely suture the proximal end of each conduit to the patient's aorta in order to obtain a strong, fluid tight connection, which is a highly technical and time consuming procedure. Nevertheless, when performing bypass surgery via conventional, open-chest procedures in which the patient's sternum is split and retracted, the surgeon has essentially unobstructed access to the heart and aorta, which reduces the difficulty of forming the proximal anastomoses between the vascular conduits and the patient's aorta.

During the last several years, however, there has been a movement away from open-chest surgery toward minimally invasive cardiac surgery. Some of the cardiac procedures presently being performed in a minimally invasive manner include, for example, coronary artery bypass, mitral or aortic valve repair or replacement, and septal defect repair. These procedures are typically carried out through incisions made between the ribs, which requires surgeons to operate with considerably less access to the heart and aorta as compared to open-chest procedures. This reduced access to the heart has increased the difficulty and time associated with forming the anastomoses between the vascular conduits and the patient's arteries, and in particular, the proximal anastomoses between the vascular conduits and the patient's aorta. More specifically, the already highly technical procedure of suturing the vascular conduits to the aorta or other arterial blood source (as well as to the coronary arteries) is even more difficult when the surgeon is operating through a small port, e.g., an incision 3 or 4 inches in length. As a secure, fluid tight anastomosis is highly desirable in order to provide long term patency of the conduit bypassing the blockage, minimally invasive cardiac surgery presents significant challenges for the surgeon.

The devices and methods used in conventional open-chest cardiac surgery, however, are not always usable or readily adaptable to carry out minimally invasive cardiac surgery. In addition, known devices that use staples to form an anastomosis have had limited acceptance, perhaps due to the fact that suture is the standard in cardiac surgery. Suture is biocompatible, flexible, long-lasting, and well-accepted by cardiac surgeons. As a result, there is a need in the art for improved devices and methods for performing minimally invasive cardiac procedures, and in particular forming anastomoses between vascular conduits and hollow body structures by applying suture through ports or other openings providing limited access to the body structure, and in which the suture is applied in a relatively fast and automated manner to produce a secure anastomosis which provides long term patency.

SUMMARY OF THE INVENTION

According to one aspect of the invention, a device is provided for passing one or more needles through tissue. In one preferred embodiment, the device includes a handle, a shaft assembly supporting at least one needle, and an actuator assembly. The needle is supported by the shaft assembly so as to be movable between radially extended and non-extended positions. A protective cover overlies the needle in the radially non-extended position and is movable with respect to the shaft to permit the needle to assume the radially non-extended position. An actuator assembly is operable using one hand to move the cover to allow the needle to assume the extended position and to pass the needle through tissue.

In another preferred embodiment, the device includes a handle and a shaft assembly supporting at least one needle so as to be movable between radially extended and non-extended positions. An actuator moves a ram from a first position to a second position to move the needle to the radially extended position, and also passes the needle through tissue.

In another preferred embodiment, the device includes a handle and a shaft assembly supporting a plurality of needles and a plurality of separate lengths of sutures, the needles being movable between extended and non-extended positions. One end of each length of suture is secured to one of the needles and the other end of each length of suture is located away from the needles.

In more specific preferred embodiments, the handle assembly of the device is preferably generally pistol shaped while the actuator assembly comprises a trigger. This preferred construction permits the device to be operated using one hand by grasping the handle assembly in one hand and moving the trigger with one finger.

In other specific preferred embodiments, the shaft assembly removably supports first and second sets of needles secured to separate lengths of sutures. Each length of suture has a needle from the first set at one end and a needle from the second set at an opposite end. A suture supporting tube is provided on the shaft assembly to organize the lengths of suture and support the second set of needles.

In other specific preferred embodiments, the device is provided with a needle guard in the form of a shield surrounding the needles and movable between expanded and collapsed orientations. The shield expands as the needles assume their radially extended orientation such that the shield is always positioned exterior to the needle. This feature enables the device to be used to pass the needles through tissue adjacent a medical device that includes a portion capable of being punctured, with the shield ensuring that the needles do not engage the portion or component.

According to another aspect of the invention, a method is provided for passing one or more needles through tissue adjacent an opening in the tissue. In one preferred embodiment, the method includes steps of providing at least first and second needles secured to first and second lengths of suture, respectively. The needles are positioned through an opening passing through a tissue wall in a patient's body, and then are passed through the tissue wall adjacent the opening so that each suture length has a portion extending through the opening and a portion extending through the tissue wall.

In another preferred embodiment, each of the first and second lengths of suture have an end disposed away from the needles to which the length of suture is secured. The first and second needles are positioned inside a patient's body adjacent an opening in tissue such that the ends of the first and second lengths of suture are located outside an outer surface of the tissue. The ends of the first and second lengths of suture are maintained outside the outer surface of the tissue while the first and second needles are passed into the tissue adjacent the opening, and then out of the tissue to pull the first and second lengths of suture through the tissue.

According to another aspect of the invention, a device is provided for delivering a member adapted to be secured to a patient's body tissue. The device includes a first component and a second component mounted to the first component, the first and second components being relatively movable. The first component is configured to removably support a member adapted to be secured to a patient's body tissue, while the second component is configured to hold at least one needle carrying suture for securing the member to the body tissue. The first component is relatively movable with respect to the second component to move the member along the suture into contact with the body tissue.

In one preferred embodiment, the first component is a shaft and the second component is a collar movably mounted on the shaft. A member adapted to be secured to body tissue is supported by the shaft while the collar has an area configured to hold one or more needles each carrying suture extending from the body tissue. After the needles have been placed in the collar so as to pass through the member supported on the shaft, a user imparts relative movement to the shaft and collar to move the shaft and the member along the suture into engagement with the body tissue.

In more specific preferred embodiments, the shaft is in the form of a tube with a hollow interior configured to receive a vascular conduit adapted to be anastomosed to the body tissue. The vascular conduit is guided along the suture into contact with the body tissue by imparting relative movement to the shaft and collar.

According to yet another aspect of the invention, a method is provided for delivering a member adapted to be secured to body tissue. In one preferred embodiment, the method includes steps of placing at least one length of suture through body tissue so that the suture extends away from the body tissue, the suture having an end which carries a needle, and providing a delivery device including first and second components mounted so as to be relatively movable. The member adapted to be secured to the body tissue is positioned on the first component, and the needle carried by the end of the suture is placed through the member into the second component. Relative movement is imparted to the first and second components to move the first component and the member along the suture to a location adjacent the body tissue.

In more specific preferred embodiments, the member is adapted to be secured to the body tissue adjacent an opening in the body tissue, and separate lengths of suture are passed through the body tissue adjacent the opening. The member may be adapted to be secured over the opening in the body tissue, with the lengths of suture passing through the tissue at locations spaced around the opening. For example, the member may be a patch adapted to be attached within a patient's heart to repair an atrial or ventricular septal defect, or a valve adapted to be attached to a patient's mitral or aortic valve annulus.

In other specific preferred embodiments, the member is a vascular conduit adapted to be anastomosed to an arterial conduit in the patient's body, for example, the aorta. Separate lengths of suture are circumferentially disposed around an opening in the wall of the aorta, with the two ends of each length of suture disposed outside the patient's body and the portion connecting the ends extending through the opening and then though the wall of the aorta. One end of each of suture length is passed through the end of the vascular conduit and the conduit is guided along the suture until it contacts the wall of the aorta over the opening. The ends of each suture length are knotted and the knots pushed against the wall of the aorta to secure the end of the conduit thereto. Alternatively, the sutures may be secured by clips or other fasteners located adjacent the wall of the aorta.

In still another aspect of the invention, an anastomosis system is provided for securing a vascular conduit to a hollow body structure. In the preferred embodiment, the system includes a needle passer comprising a shaft assembly supporting first and second needles and at least one length of suture. An actuator moves at least one of the needles and the length of suture through the tissue of a hollow body. A sealing element configured to be positioned against the end of the vascular conduit is also provided, the sealing element being formed of a material that is able to receive one of the first and second needles. In a specific preferred embodiment, the sealing element is ring-shaped and is formed of a resilient material.

In still another aspect of the invention, a device for use in anastomosing a vascular conduit to a hollow body structure is provided. In the preferred embodiment, the device comprises a sealing element having an opening configured to be aligned with a vascular conduit. The sealing element is formed of a biocompatible material which permits at least one needle to be inserted and passed through the sealing element, thereby permitting suture used to anastomose the vascular conduit to the hollow body structure to be passed through the sealing element.

In still another aspect of the invention, a method for anastomosing a vascular conduit to a hollow body structure so that the vascular conduit is in fluid communication with the interior of the hollow body structure is provided. In the preferred embodiment, the method comprises steps of forming an opening in the tissue of a hollow body structure so that the opening passes into an interior of the body structure, positioning an end of a vascular conduit against the tissue, and attaching the vascular conduit to the tissue so that the vascular conduit is in fluid communication with the interior of the body structure. According to the invention, a sealing element is used to enhance the attachment between the end of the vascular conduit and the tissue.

According to yet another aspect of the invention, a cutting instrument is provided for forming an access opening into a body lumen or cavity, such as a blood vessel. The opening provides access into the lumen or cavity while minimizing damage to the lumen wall, which may occur, for example, during formation of the opening or subsequent introduction of an instrument through the opening. In one preferred embodiment, the cutting instrument comprises a knife having a plurality of cutting surfaces arranged to cut an opening in tissue having a plurality of flaps. The flaps distribute the force exerted on the tissue over several locations so that introducing an instrument through the opening is less likely to propagate a tear along the cut lines.

According to yet another aspect of the invention, a measuring device is provided for gauging the size of a hollow member, such as a vascular conduit. The device includes a pair of jaws provided with tips that contact the opposite inner surfaces of the conduit. The jaws are relatively movable and are biased apart to contact the inner surfaces of the conduit. A scale coupled to the jaws provides a visual indication of the size of the internal dimension of the conduit. In one preferred embodiment, a spring biases first and second jaws apart, and an arm extends from the second jaw and pivotally mounts a rotating scale provided with a series of lumen sizes. The scale is coupled to the first jaw and rotates about the pivot when the first jaw moves into contact with the lumen of the conduit. A mark carried by the second arm indicates the lumen size upon the tips of both jaws contacting the inner lumen surfaces.

According to still another aspect of the invention, a device and method for carrying out a surgical procedure on a hollow body structure through which fluid is flowing is provided. In a preferred embodiment, the method includes steps of foiming an opening passing through the hollow body structure which extendsfrom an exterior surface to an interior surface of the hollow body structure, providing a tissue contacting member movable between collapsed and expanded orientations, the tissue contacting member being attached to an elongate support member, and positioning the tissue contacting member in the collapsed orientation through the opening and adjacent the interior surface of the hollow body structure. The tissue contacting member is moved into the expanded orientation and into contact with the interior surface of the hollow body structure, and an instrument is inserted through the opening and into the hollow body structure to carry out a surgical procedure on the hollow body structure, with the tissue contacting member substantially preventing fluid flowing through the hollow body structure from escaping through the opening. In a specific prefenred embodiment, the hollow body structure is a patient's aorta, and the surgical procedure is carried out to anastomose a vascular conduit to the aorta.

BRIEF DESCRIPTION OF THE DRAWING FIGURES

Other features, benefits and advantages of the invention will be apparent from the detailed description of preferred embodiments which follows, taken in conjunction with the accompanying drawing Figures, wherein:

FIG. 3 is a perspective view of the shaft assembly forming part of the needle passer shown in FIG. 1;

FIG. 4 is an exploded perspective view of the shaft assembly shown in FIG. 3;

FIG. 9A is a side elevation view of the needle passer shown in FIG. 8A, with the device shown in a first stage of actuation;

FIG. 9B is a side elevation view isolating a portion of the actuator assembly in the position shown in FIG. 9A;

FIG. 10A is a side elevation view of the needle passer shown in FIG. 9A, with the device shown in a second stage of actuation;

FIG. 10B is a side elevation view isolating a portion of the actuator assembly in the position shown in FIG. 10A;

FIGS. 21A–21C are side elevation views, partly in section, showing the needle passer illustrated in FIG. 20A being used to pass a first set of needles through the wall of the aorta according to another embodiment of the invention;

FIG. 37C is a side elevation view of the needle passer shown in FIG. 37B, with the device shown in a second stage of actuation;

FIG. 37D is a side elevation view of the needle passer shown in FIG. 37C, with the device shown in a third stage of actuation;

DETAILED DESCRIPTION OF PREFERRED EMBODIMENTS

The present invention comprises various devices and associated methods of using the devices to perform medical procedures, and in particular minimally invasive surgical procedures. One device is referred to as a needle passer and is used to pass one or more needles through tissue. Another device is referred to as a delivery device and is used to deliver a member adapted to be secured to body tissue to a location adjacent the tissue. Additional devices and methods are disclosed which may be used with or without the needle passer or delivery device.

Figure 1:
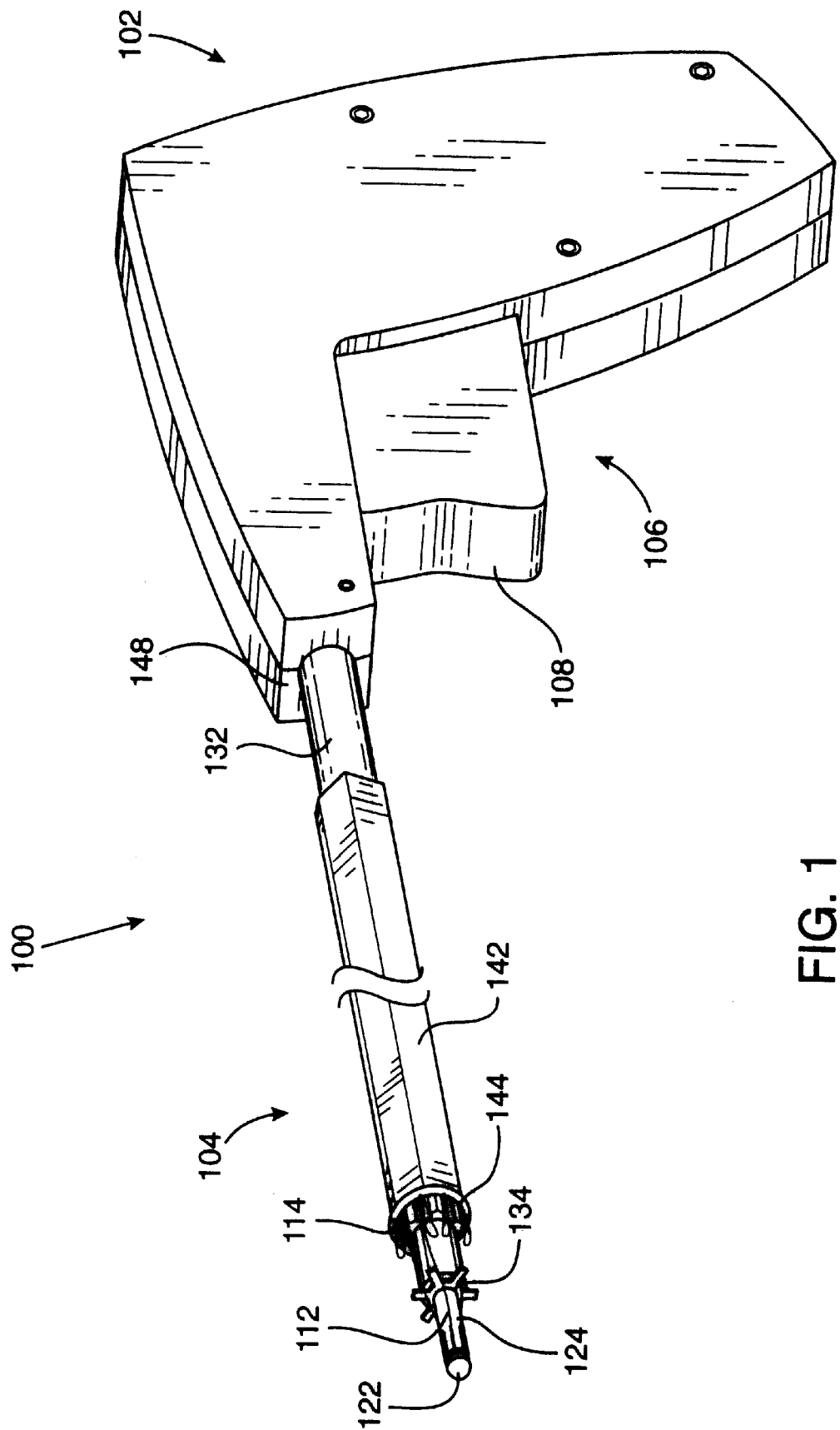
FIG. 1 is a perspective view of a needle passer constructed according to one preferred embodiment of the invention.

Referring to FIG. 1, a needle passer constructed according to a first embodiment of the invention is designated generally by the reference numeral 100 and comprises a handle 102 and a shaft assembly 104 which is operated by an actuator assembly 106. The needle passer 100 is preferably configured so that a user can grasp and operate it using one hand. In the preferred embodiment, the handle 102 is pistol-shaped and the actuator assembly 106 includes a movable component that can be manipulated using one finger. The preferred movable component comprises a trigger 108 which is depressed in order to actuate the actuator assembly 106 and pass one or more needles through tissue.

As shown best in FIGS. 2A–2D, the shaft assembly 104 supports one or more needles configured to be passed through tissue. In the illustrated and preferred embodiment, the shaft assembly 104 removably supports a first set of needles 110 each of which is secured to a first end of a length of suture 112. A second end of each suture length 112 is secured to one of a second set of needles 114 which are removably supported by the shaft assembly 104. While the second ends of the suture lengths 112 are shown secured to the second set of needles 114, they could alternatively by secured to the shaft assembly 104, another portion of the needle passer 100, a vascular conduit adapted to be secured to the tissue, or an element used to enhance the seal between the conduit and body tissue.

As used herein, the term suture means any flexible or substantially flexible filament or filament-like material suitable for use in anastomosing tissue. The suture 112, in the preferred embodiment, is 5-0 or 6-0 type suture, while the needles 110, 114 are preferably CC or CC-1 style straight cardiovascular needles. The needles 110, 114, however, could instead have a bent, curved or other nonlinear profile. In addition, while the illustrated embodiment includes six needles in each set, any number of needles may be used. The first and second sets of needles preferably contain the same number of needles arranged in pairs disposed at the opposite ends of each length of suture, although other arrangements could be used. For example, a single needle could be carried at one end of a suture length and passed through tissue and grasped in order to traction the tissue. In this application, which may be used to place one or more traction sutures in the pericardium to allow its retraction to expose the heart, the opposite end of each length of suture need not be secured to a needle.

Figure 2A:
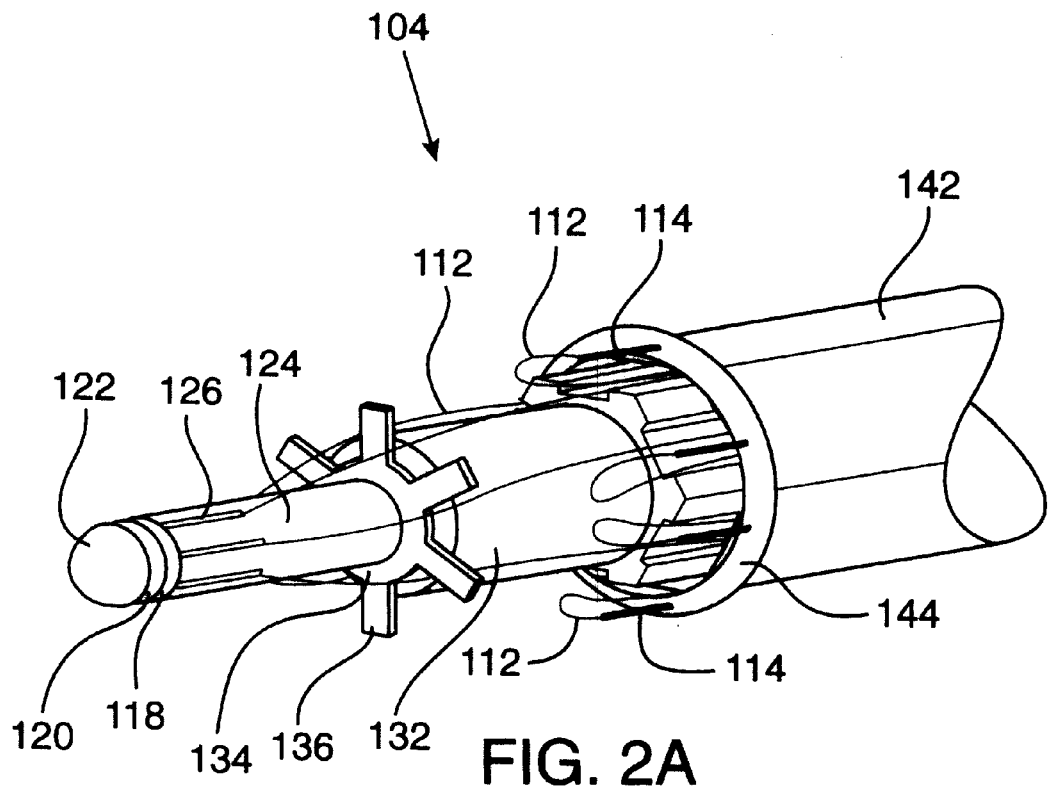
FIGS. 2A–2D are enlarged perspective views of a portion of a shaft assembly forming part of the needle passer shown in FIG. 1, wherein the needle passer is shown, respectively, in an initial position prior to actuation, a first stage of actuation, a second stage of actuation, and a third stage of actuation.

FIG. 2A shows the distal end of the shaft assembly 104 in an orientation corresponding to an initial position of the needle passer 100, wherein the needles 110 have not yet been oriented to be passed through tissue. The needles 110 are supported on a shaft 116 the distal end of which is provided with a collar 118 having openings that receive and retain the needles 110. Each needle 110 extends through an opening in the collar 118 and is removably held by an O-ring 120 located in an annular groove defined in the collar. The O-ring 120 engages the exterior of each needle 110 to frictionally retain it in the collar 118. The blunt end of each needle 110 abuts the inner side of an atraumatically-shaped distal end 122 of the collar, while the sharpened end of each needle is disposed away from the distal end 122.

Each needle 110 is held in the collar 118 by the O-ring 120 so that it can be removed from the collar by pulling the needle away from the distal end 122. Other structures, of course, may be used to removably hold the needles 110. In the preferred embodiment, the needles 110 are movable between radially extended and non-extended positions. Thus, each of the openings in the collar 118 extends radially a sufficient amount to permit the needles 110 to move from the radially non-extended position shown in FIG. 2A to a radially extended position shown in FIGS. 2C and 2D. The slots in the collar 118 preferably are configured to limit or control the extent to which the needles 110 can move radially.

The shaft assembly 104 is preferably provided with a mechanism that protects the needles 110 when they are in their radially non-extended position. In the illustrated and preferred embodiment, the mechanism comprises a protective cover 124 in the form of a sleeve slidably disposed over the shaft 116 so as to overlie the needles 110; alternative structures, however, may be used to protect the needles. As shown in FIGS. 1 and 2A, the cover 124 has a plurality of slots 126 through which the suture lengths 112 pass from the first set of needles 110 to the second set of needles 114. In use, the trigger 108 of the actuator 106 is depressed to move the cover 124 away from the distal end of the shaft 116 and expose the needles 110, this position being shown in FIG. 2B. Once exposed, the needles 110 are free to move into their radially extended position for being passed through tissue. In the preferred embodiment, the needles 110 are forced into their radially extended position by a mechanism activated by the actuator assembly 106. It will be recognized, however, that an alternative manner of moving the needles 110 to their radially extended position could be used. For example, the needles 110 could be formed of a superelastic material and formed so that in an unbiased state they are disposed away from the shaft 116, which results in the needles moving radially away from the shaft 116 upon being exposed by the cover 124. Alternatively, one or more spring members (not shown) could be disposed on the shaft 116 to bias the needles 110 radially outward into a splayed configuration upon being exposed by the cover 124.

Figure 2B:
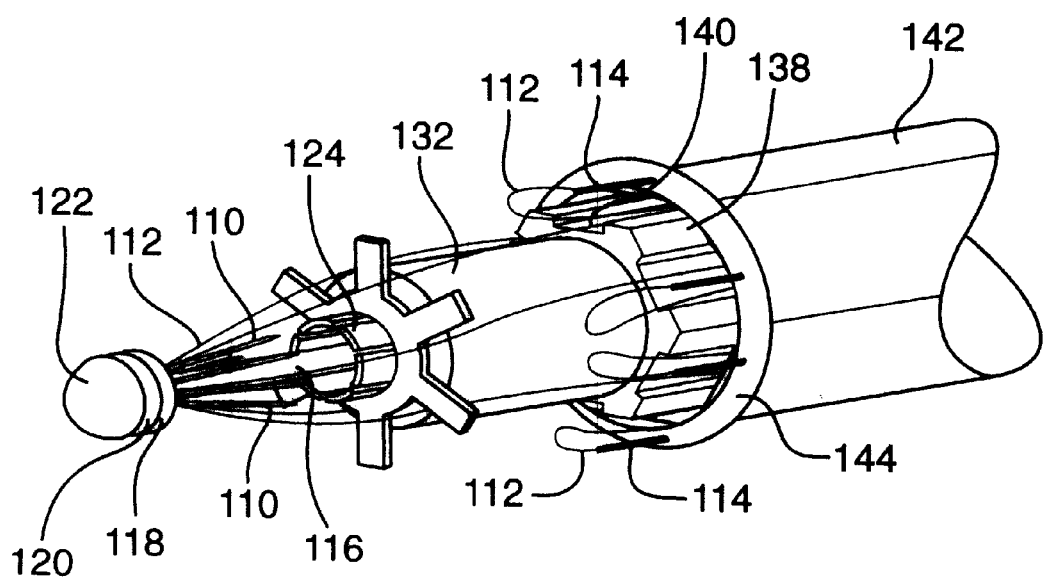
Figure 2C:
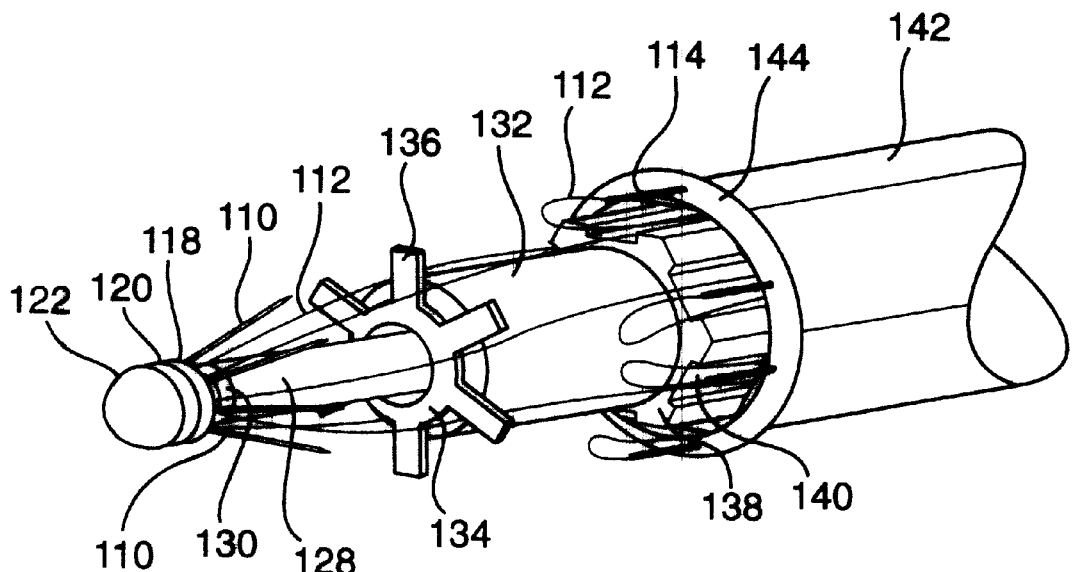

In the preferred construction, the needles 110 are moved to their radially extended position by a ram member slidably disposed over the shaft 116. In the illustrated embodiment, the ram is in the form of a sleeve 128 having a forward end 130 which contacts and moves the needles 110 to their radially extended position. The forward end 130 is preferably formed with a slight taper to smoothly contact and move the needles 110. As explained above, depressing the trigger 108 (from the position of FIG. 2A) causes the actuator assembly 106 to retract the cover 124 which exposes the needles 110, as shown in FIG. 2B. Further depressing the trigger 108 (from the position of FIG. 2B) causes the actuator assembly 106 to move the ram sleeve 128 toward the distal end of the shaft 116 which moves the needles 110 to their radially extended position, as shown in FIG. 2C. The actuator assembly 106 is preferably constructed so that the ram sleeve 128 does not move forward into contact with the needles 110 until the cover 124 has been fully retracted. If desired, the actuator assembly 106 may be provided with a safety mechanism (not shown) to prevent inadvertent actuation of the trigger 108.

Figure 2D:
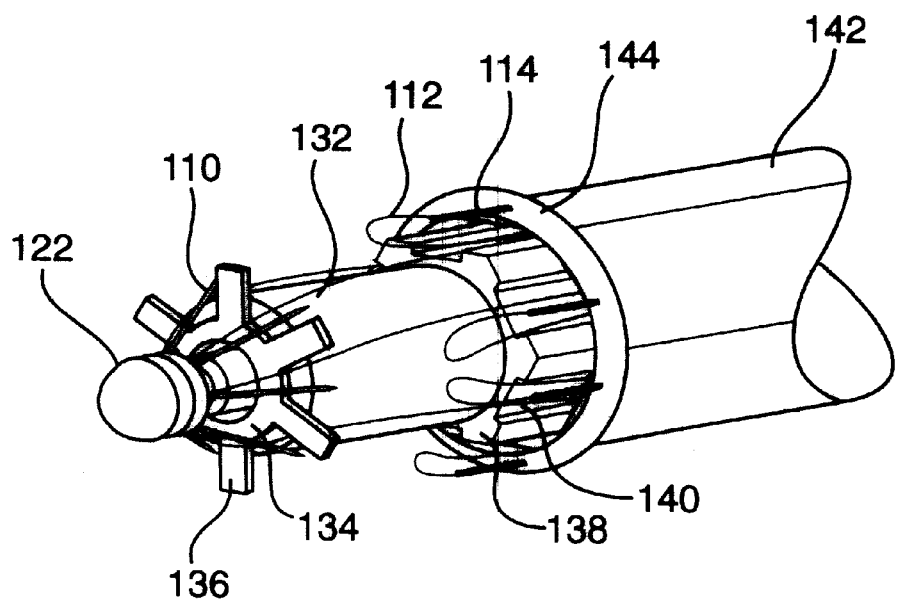

Once in the position shown in FIG. 2C, with the cover 124 retracted and the ram sleeve 128 moved forward to force the needles 110 into their radially extended position, the needle passer 100 is ready to pass the needles 110 through tissue. Further depressing the trigger 108 (from the position of FIG. 2C) causes the actuator to move the needles 110 in a proximal direction (toward the handle 102), as shown in FIG. 2D. The actuator 106 accomplishes this by moving the shaft 116, the ram sleeve 128, and the cover 124 together in a proximal direction with respect to the handle 102, and with respect to a suture tube 132 which forms the outermost member of the shaft assembly 104 and is fixed to the handle 102. The suture tube 132 is provided with a foot 134 at its distal end which rests on tissue opposite the surface of the tissue through which the needles 110 pass as they move to the position of FIG. 2D. The foot 134 includes a plurality of radially extending fingers 136 separated by gaps that receive the needles 110 after they have passed through the tissue. The gaps between the fingers 136 of the foot 134 also receive the suture lengths 112 which extend to the second set of needles 114.

In the preferred construction, the suture tube 132 secures the shaft assembly 104 to the handle 102, and also supports the second set of needles 114 and organizes the suture lengths 112 extending between the first and second sets of needles. The suture tube 132 comprises a suture organizer portion 138 defining a plurality of channels 140 each of which receives a suture length 112, the suture preferably being coiled in the channel. An outer sleeve 142 is secured to the tube 132 so as to enclose the channels 140 along the length thereof to retain the suture lengths 112. An alternative construction of the suture tube 132 could include separate tubes respectively disposed in each channel 140, each tube receiving a length of suture. In this embodiment the outer sleeve 142 could be used to secure the tubes in the channels 140, or it could be omitted if the tubes are otherwise secured in the channels.

The suture tube 132 preferably has an O-ring 144 which the ends of needles 114 may be placed into (or under) so as to be removably held by the tube 132. As shown in FIG. 2A, each suture length 112 passes through a slot 126 in the cover 124 and around a finger 136 of the foot 134, extends along the length of a channel 140 toward the handle 102, and then loops around and extends back to where it is attached to one of the second set of needles 114. Thus, when a needle 110 that has been passed through tissue is pulled completely through the tissue and away from the collar 118, the suture length 112 attached to the needle uncoils in the channel 140 and is threaded through the tissue.

Figure 5:
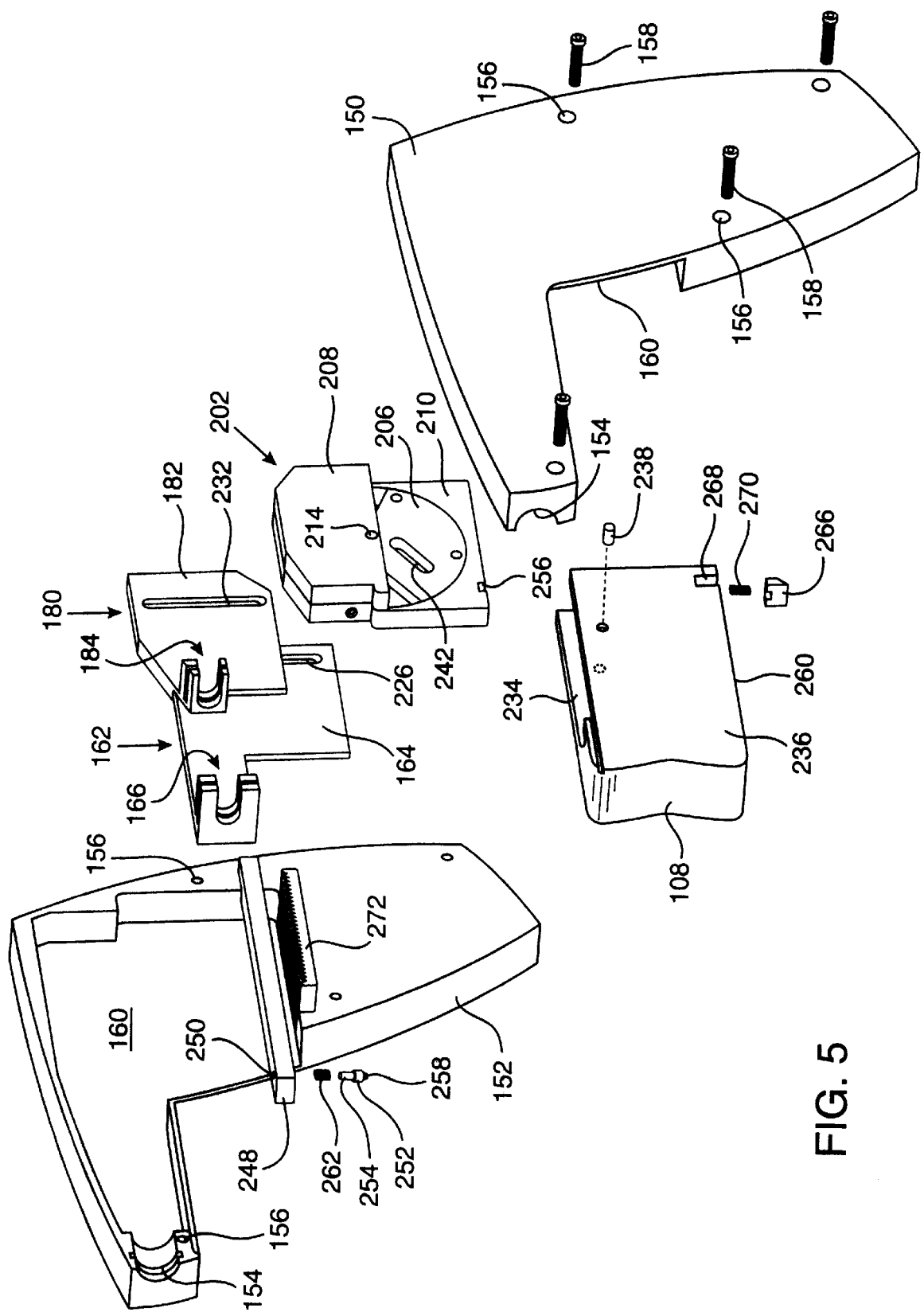
FIG. 5 is an exploded perspective view of a handle and actuator assembly forming part of the needle passer shown in FIG. 1.

FIGS. 3 and 4 show the shaft assembly 104 and illustrate the relationship between the relatively movable components thereof. As shown in FIG. 3, the shaft 116, ram sleeve 128 and cover 124 are slidably nested one within the other. These three nested components are slidably disposed within the suture tube 132. The suture tube 132 has a flange 146 adjacent its proximal end which is fixed within a barrel portion 148 of the handle 102 (FIG. 1). As shown in FIG. 5, the preferred handle 102 comprises first and second portions 150, 152 secured in a side-by-side manner. The handle portions 150, 152 have grooves 154 which cooperate to form an annular groove in which the flange 146 of the suture tube 132 is fixed by any suitable means.

The handle portions 150, 152 may be secured together in any known manner, for example, the portions may be provided with mating apertures 156 that receive threaded fasteners 158. The handle portions 150, 152 are preferably formed of injection molded plastic with the apertures 156 threaded to receive fasteners 158. Although the illustrated handle 102 is formed by separate pieces secured together, it could instead be formed of a single piece. The handle portions 150, 152 are preferably shaped so that the needle passer 100 has a generally pistol-shaped configuration which may be grasped in one hand, as shown in FIG. 1. However, while a pistol-shaped handle is preferred and illustrated, it will be recognized that other configurations may be used, such configurations preferably permitting the needle passer to be grasped and operated using one hand.

Each handle portion 150, 152 has a recess 160 configured to receive part of the shaft assembly 104, as well as the actuator assembly 106 which actuates the shaft assembly to the different illustrated positions. FIGS. 5 and 6A–6D show a preferred embodiment of the actuator assembly 106. It should be recognized, however, that alternative assemblies or mechanisms for moving the shaft assembly 104 between its various positions may be utilized without departing from the basic concepts and principles behind the invention.

Figure 7:
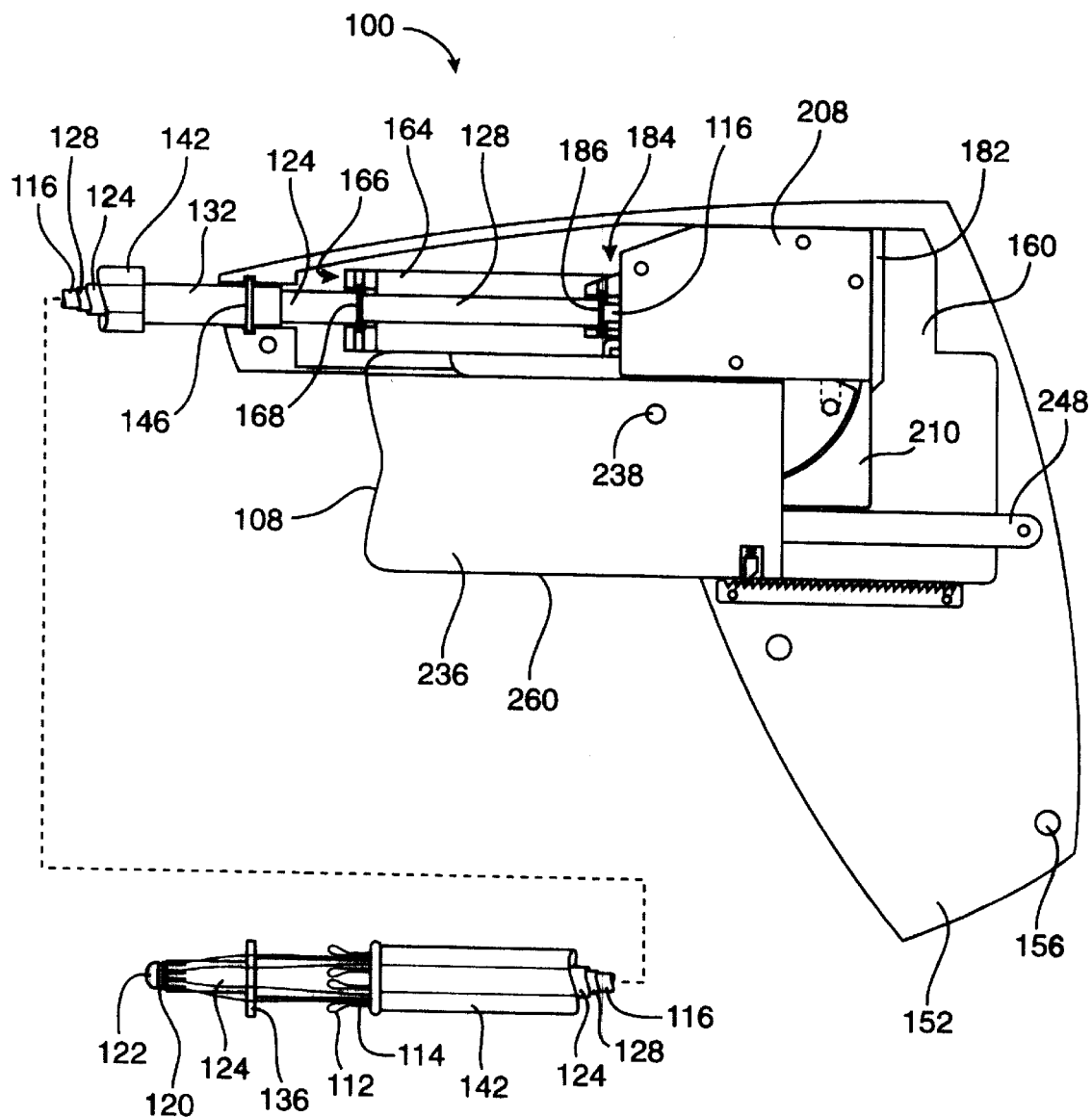
FIG. 7 is a side elevation view of the needle passer shown in FIG. 1, with part of the handle broken away and the device shown in an initial position prior to actuation.

The preferred actuator assembly 106 comprises a cover driver 162 which engages and moves the cover 124 to expose the needles 110. The preferred cover driver 162 comprises a body portion 164 and a bracket 166 which engages a flange 168 formed on the cover 124 (FIGS. 4 and 7). The bracket 166 includes first and second spaced plates 170, 172 defining a gap 174 which receives the flange 168 of the cover 124 in a secure manner, for example, by a friction fit, adhesive, etc. The plates 170, 172, respectively, have cut-outs 176, 178 through which the tubular body of cover 124 passes (FIG. 7).

Referring to FIGS. 5 and 6A–6E, the actuator assembly 106 also comprises a ram driver 180 which engages and moves the ram sleeve 128 to move the needles into their radially extended position. In the preferred embodiment, the ram driver 180 comprises a body portion 182 and a bracket 184 which engages a flange 186 formed on the ram sleeve 128 (FIGS. 4 and 7). The bracket 184 is similar to bracket 166 and includes first and second spaced plates 188, 190 defining a gap 192 which receives the flange 186 of the cover 124 in a secure manner, preferably in the same manner that the bracket 166 of cover driver 162 is secured to the flange 168 of the cover 124. The plates 188, 190, respectively, have cut-outs 194, 196 through which the tubular body of ram sleeve 128 passes. The cover 124 and the ram sleeve 128 are fixed, respectively, to the cover driver 162 and the ram driver 180, and thus are moved when the cover and ram drivers are moved by the actuator assembly 106 upon depressing the trigger 108.

Figure 6A:
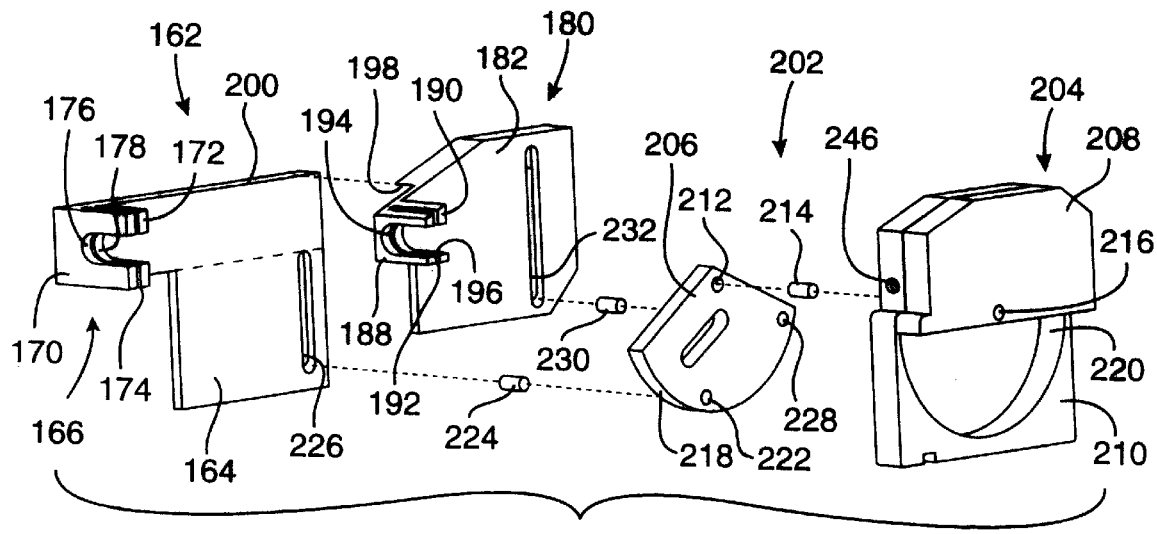
FIG. 6A is an exploded perspective view of a portion of the actuator assembly shown in FIG. 5.
Figure 6B:
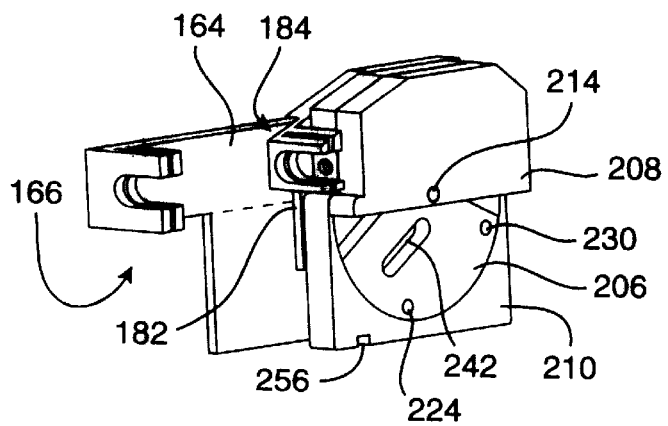
FIG. 6B is a perspective view of the portion of the actuator assembly shown in FIG. 6A with the components assembled.
Figure 6C:
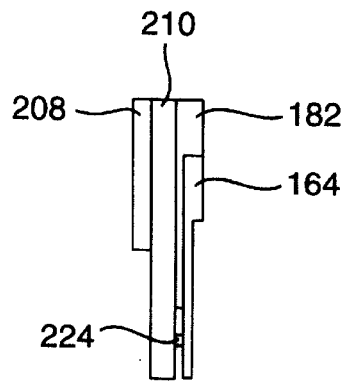
FIG. 6C is an end elevation view of the portion of the actuator assembly shown in FIG. 6B, looking at the rear of the assembly.

The ram driver 180 has a ledge 198 which sits on an upper edge 200 of the cover driver 162 so that the two components slide with respect to one another during actuation of the needle passer 100 (FIG. 6A). In order to transmit motion from the trigger 108 to the cover driver 162 and the ram driver 180, the actuator assembly 106 includes a transmission 202 which comprises a linkage housing 204 and a rotary linkage 206. In the illustrated embodiment, the linkage housing 204 comprises a first housing member 208 and a second housing member 210 secured together by any suitable means; however, for manufacturing reasons it may be desirable to form the housing 204 of a single piece. The rotary linkage 206 has a bore 212 which receives a pin 214 rotatably secured in a bore 216 in the first housing member 208. The rotary linkage 206 and pin 214 rotate with respect to the linkage housing 204. The rotary linkage 206 is preferably formed as a portion of a cylinder having an outer surface 218 which slides along a complementarily shaped surface 220 provided on the second housing member 210 of the linkage housing 204.

The rotary linkage 206 is coupled to the cover driver 162 and the ram driver 180 so that rotating the linkage 206 within the linkage housing results in linear movement of the cover 124 (fixed to the bracket 166 of cover driver 162) and the ram sleeve 128 (fixed to the bracket 184 of ram driver 180). In the preferred embodiment, as shown in FIGS. 6A–6E, the rotary linkage 206 has a first bore 222 containing a pin 224 engaged with a slot 226 in the body portion 164 of the cover driver 162. Rotating the linkage 206 thus drives the pin 224 against the slot 226 to move the cover driver 162. Similarly, the rotary linkage 206 has a second bore 228 containing a pin 230 engaged with a slot 232 in the body portion 182 of the ram driver 180. Thus, rotating the linkage 206 also drives the pin 230 against the slot 232 to move the ram driver 180.

Figure 6D:
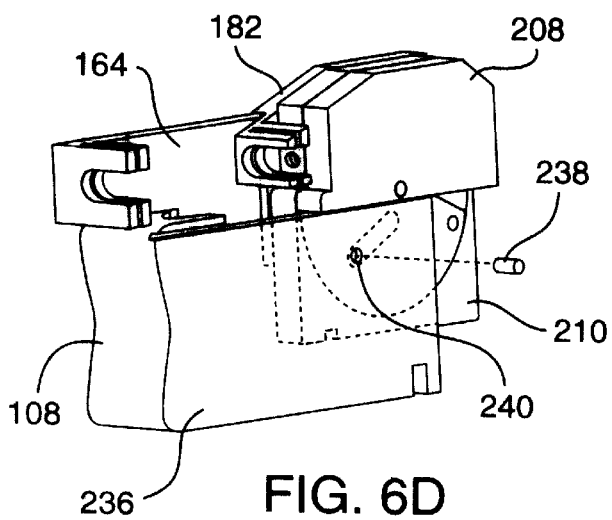
FIG. 6D is a perspective view of the portion of the actuator assembly shown in FIG. 6B, including a trigger.
Figure 6E:
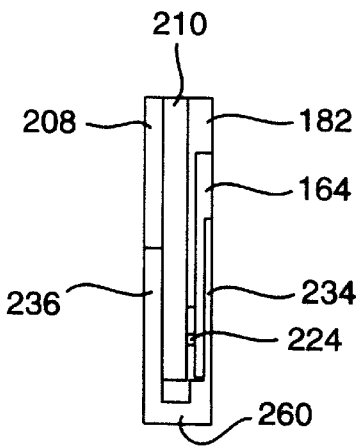
FIG. 6E is an end elevation view of the actuator assembly shown in FIG. 6D, looking at the rear of the assembly.

The rotary linkage 206 is rotated by depressing the trigger 108 which sequentially moves the shaft assembly 104 from the position shown in FIG. 2A to the position shown in FIG. 2D. In particular, with reference to FIGS. 5, 6D and 6E, the trigger 108 comprises opposite side walls 234, 236 which define a hollow interior that receives the cover driver 162, the ram driver 180, and the transmission 202 (i.e., the linkage housing 204 and the rotary linkage 206). A pin 238 is mounted in a bore 240 formed in one of the trigger side walls 234, 236 and passes through a slot 242 formed in the rotary linkage 206 (FIG. 6D). As such, depressing the trigger 108 drives the pin 238 against the slot 242 to rotate the rotary linkage 206 within the linkage housing 204.

The preferred actuator assembly 106 is constructed so that depressing the trigger 108 rotates the rotary linkage 206 when moving the shaft assembly 104 from the position shown in FIG. 2A to the position shown in FIG. 2B and from the position shown in FIG. 2B to the position shown in FIG. 2C, but not from the position shown in FIG. 2C to the position shown in FIG. 2D. That is, the rotary linkage 206 rotates within the linkage housing 204 only when the actuator assembly 106 moves the cover 124 to expose the needles 110 and moves the ram sleeve 128 to force the needles 110 into their radially extended position. In order to move the needles 110 with respect to the handle 102 and suture tube 132, depressing the trigger 108 does not rotate the linkage 206, but instead moves the entire actuator assembly (cover driver 162, ram driver 180, linkage housing 204 and rotary linkage 206) within the handle 102.

Moving the entire actuator assembly 106 within the handle 102 also moves the needles 110 because the shaft 116 which carries the needles is secured to the linkage housing 204. In the preferred embodiment, the proximal end of the shaft 116 is provided with threads 244 (FIG. 4) which engage a threaded bore 246 provided in the linkage housing 204 (FIG. 6A). The shaft 116, of course, may be secured to the linkage housing 204 by other means, for example, the end of the shaft 116 may be otherwise configured to be secured in a bore in the linkage housing. One benefit of the threaded end 244 is that it permits fine adjustment of the position of the shaft 116 in the linkage housing 204 (and thus the relative position of the needles 110 and foot 134) upon assembling the components of the needle passer, thereby compensating for manufacturing tolerances of the components.

Referring now to FIGS. 5 and 7–11, the actuator assembly 106 is provided with a mechanism for controlling whether depressing the trigger 108 rotates the rotary linkage 206 within the linkage housing 204 (to expose and then move the needles 110 into their radially extended position), or moves the linkage housing 204 and the shaft 116 with respect to the handle 102 (to pass the needles 110 through tissue). The preferred mechanism comprises a rail 248 having a bore 250 in which a lock pin 252 is positioned. The rail 248 is secured to the handle 102 (or, alternatively, formed integrally with the handle) so as to be immovable with respect to the handle. While the lock pin 252 can move vertically within the bore 250 of rail 248, it is prevented from moving along the direction indicated by arrow A. The lock pin 252 has an end 254 which extends into a notch 256 formed in the underside of the linkage housing 204 (FIG. 8A). Thus, when the end 254 of lock pin 252 engages the linkage housing 204, as shown in FIG. 8A, the linkage housing is prevented from moving with respect to the handle 102 along the direction of arrow A. The lock pin 252 has an opposite end 258 which is biased into engagement with a bottom wall 260 of the trigger 108 by a spring 262, when the actuator assembly 106 is in the position of FIG. 8A.

Figure 8A:
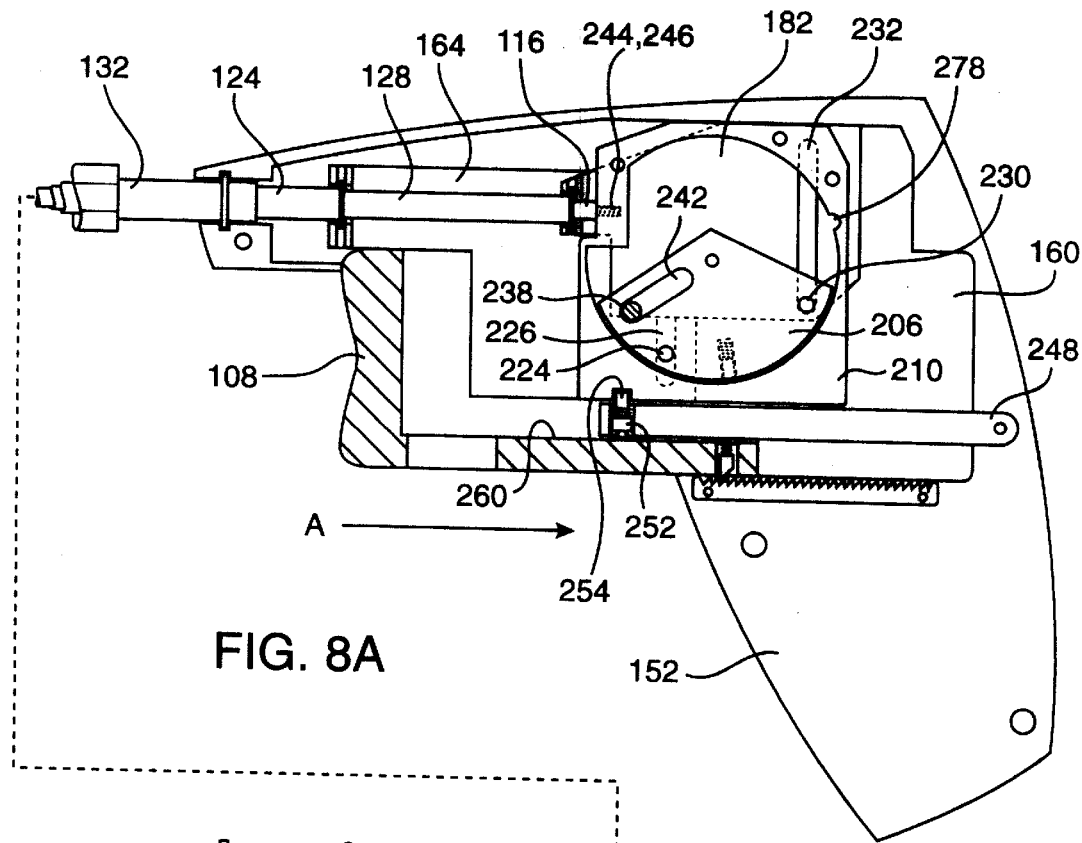
FIG. 8A is a side elevation view of the needle passer in the position shown in FIG. 7, with the trigger shown in section and part of the actuator assembly broken away.
Figure 8B:
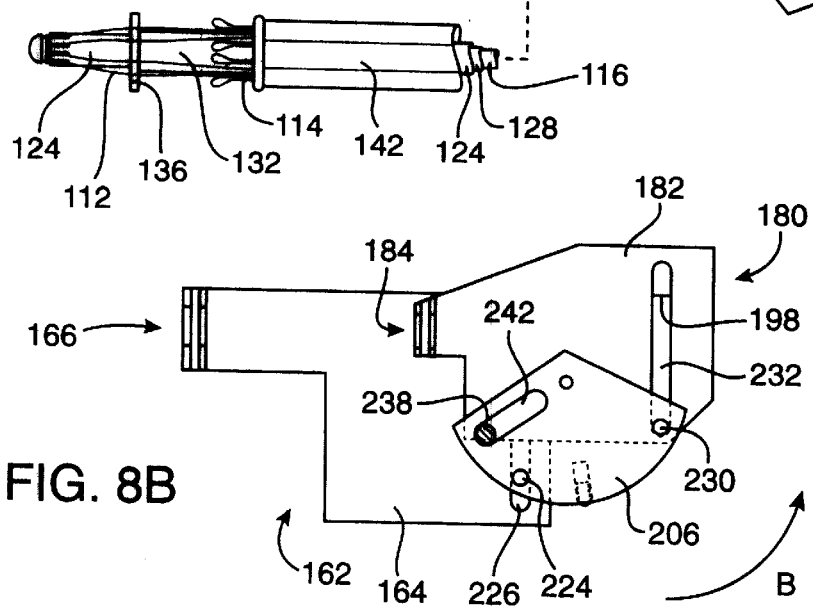
FIG. 8B is a side elevation view isolating a portion of the actuator assembly in the position shown in FIG. 8A.

FIGS. 8A and 8B illustrate the needle passer 100 (with handle portion 150 omitted for clarity) in a position where the cover 124 overlies the needles 110 and the ram 128 is retracted. The cover driver 162 is positioned within the handle recess 160 so that the cover 124 extends to the collar 118 and overlies the needles 110. The ram driver 180 is positioned so that the ram sleeve 128 is retracted out of engagement with the needles 110. FIG. 8B is an isolation view showing the rotary linkage 206 in engagement with the cover and ram drivers 162, 180, as they are positioned in FIG. 8A. The rotary linkage 206 is in its initial position, i.e., prior to being rotated along the direction indicated by arrow B by depressing the trigger 108 in the direction of arrow A. For purposes of explanation, movement of the trigger 108 and the actuator assembly 106 is broken into three stages. In operation though, the trigger 108 is depressed continuously so that the actuator assembly 106 retracts the cover 124, moves the ram sleeve 128 forward, and retracts the needles 110 in a smooth, uninterrupted manner. However, if desired, the actuator assembly 106 may be provided with detents or other structure (not shown) which provides an audible or tactile indication when the trigger 108 reaches one or more of the aforementioned stages.

FIGS. 9A and 9B illustrate the needle passer 100 in a first stage of actuation wherein the cover 124 has been retracted by depressing the trigger 108 a first extent in the direction of arrow A. It should be noted that the actuator assembly 106 is preferably provided with a mechanism for preventing movement of the shaft assembly 104 in an opposite direction once actuation has started. The preferred mechanism comprises a pawl 266 carried in a notch 268 formed in the trigger 108. The pawl 266 is biased by a spring 270 into engagement with a ratchet 272 secured to (or formed integrally with) the handle 102. The pawl 266 and ratchet 272 prevent the trigger 108 from moving opposite the direction of arrow A (FIG. 7).

To reach the position of FIG. 9A, the trigger 108 is depressed from the position of FIG. 8A which forces the drive pin 238 against the slot 242 in the rotary linkage 206 to rotate the linkage in the direction of arrow B (keeping in mind that the linkage housing 204 is prevented from moving because it is fixed to the rail 248 by the lock pin 252). Rotation of the rotary linkage 206 drives the pin 224 against the slot 236 in the cover driver 162, which moves the cover driver in the direction of arrow A. This retracts the cover 124 from the position of FIG. 8A to the position of FIG. 9A due to the flange 168 of the cover 124 being fixed to the bracket 166 of the cover driver 162.

As the rotary linkage 206 rotates from the position of FIG. 8A to the position of FIG. 9A, the pin 224 moves the cover driver 162 (and cover 124) in the direction of arrow A. This is because during such rotation the location of the pin 224 on the rotary linkage 206 remains below the horizontal axis of the pivot pin 214 (as viewed in the Figures). In addition, the primary component of the motion of pin 224 is horizontal due to the initial location of the pin 224 on the rotary linkage 206 (approximately seven o'clock, as seen best in FIG. 8B). As an example, in the preferred and illustrated embodiment, the rotary linkage 206 rotates in a counter-clockwise direction approximately 25° in moving from the position of FIG. 8B to the position of FIG. 9B (with the slot 242 moving from an initial position of approximately 35° below horizontal to approximately 60° below horizontal).

Rotating the rotary linkage 206 from the position of FIG. 8A to the position of FIG. 9A also moves the pin 230 in the slot 232 of the ram driver 180. The pin 230 moves in the direction of arrow A because during such rotation it too remains below the horizontal axis of the pivot pin 214, as seen best in FIG. 9B. This results in the ram driver 180 (and ram sleeve 128) moving in the direction of arrow A, as can be seen by comparing the positions of the ram driver bracket 186 in FIGS. 8A and 9A. However, the distance that the ram sleeve 128 is retracted is small due to the initial location of the pin 230 on the rotary linkage 206 (approximately four o'clock in FIG. 8B). The primary component of the motion of pin 230 thus is vertical as the pin 230 travels within the slot 232 of the ram driver 182. Nonetheless, the ram sleeve 128 is moved away from the needles 110 before it is moved toward the needles. At the conclusion of this rotation of the rotary linkage 206, the pin 230 is located substantially at the horizontal axis of the pivot pin 214 (FIG. 9B).

FIGS. 10A and 10B illustrate the needle passer 100 in a second stage of actuation achieved by depressing the trigger 108 a second extent in the direction of arrow A. Further rotation of the rotary linkage 206 from the position of FIG. 9A to the position of FIG. 10A drives the pin 224 against the slot 226 in the cover driver 162, resulting in the cover driver continuing to move in the direction of arrow A. Thus, the cover 124 continues to be retracted as the rotary linkage 206 is moved from the position of FIG. 9A to the position of FIG. 10A. This is due to the pin 224 remaining below the horizontal axis of the pivot pin 214 during additional rotation of the rotary linkage 206.

Further rotation of the rotary linkage 206 from the position of FIG. 9A to the position of FIG. 10A also moves the pin 230 in the slot 232 of the ram driver 180. However, because at the start of this additional rotation the pin 230 is located substantially at the horizontal axis of the pivot pin 214 (FIG. 9B), the pin 230 and the ram driver 180 are moved in a direction opposite to that indicated by arrow A. As a result, the ram sleeve 128 is moved forward toward the needles 110. The first part of the movement of the ram sleeve 128 makes up for the distance it was retracted when the ram driver 180 was moved from the position of FIG. 8A to the position of FIG. 9A. After making up this distance, the ram sleeve 128 starts to achieve a positive gain, i.e., the distance between the needles 110 and the initial position (FIG. 8A) of the ram sleeve begins to decrease. When the trigger 108 and ram driver 180 reach the position shown in FIG. 10A, the ram sleeve 128 is fully engaged with the needles 110 to force them into their radially extended position.

In moving from the position shown in FIG. 9A to the position shown in FIG. 10A, the primary component of the motion of the ram driver 180 and ram sleeve 128 is horizontal, as can be seen by comparing the positions of the pin 230 in FIGS. 9B and 10B. Consequently, in a relatively short period of time the ram sleeve 128 makes up the distance that it was previously retracted and starts to achieve a positive gain. However, the cover 124 is being retracted during the time the ram sleeve 128 is moving but not achieving a positive gain, which further ensures that the needles 110 will not be forced into their radially extended position until the cover has been sufficiently retracted. As an example, in the preferred and illustrated embodiment, the rotary linkage 206 rotates in a counter-clockwise direction approximately 25° from the position shown in FIG. 9B before the ram sleeve 128 begins achieving a positive gain toward the needles 110, and then approximately an additional 50° in moving to the position shown in FIG. 10B (with the slot 242 moving from approximately 60° below horizontal to a final position of approximately 135° below horizontal).

While a rotary linkage is the mechanism used to transmit motion from the trigger 108 to the components of the shaft assembly 106 in the illustrated and preferred embodiment, it should be appreciated that other actuator mechanisms may be used, for example, a bar linkage coupling the trigger and the ram and cover drivers.

The actuator assembly 106 is next operated to pass the needles 110 through tissue. At this point it is desirable to lock the cover 124 in its retracted position and the ram sleeve 128 in its forward position, thereby ensuring that the needles 110 remain in their radially extended position as they are passed through tissue. Thus, the needle passer 100 preferably includes a mechanism for fixing the relative position of the cover 124, ram sleeve 128 and shaft 116. In the illustrated embodiment, the mechanism comprises a bullet 274 disposed in a blind bore 276 formed in the outer surface 218 of the rotary linkage 206 (FIGS. 8A–11A). The bullet 274 is biased radially outward against the surface 220 of the linkage housing member 210 by a spring disposed in the bore 276.

As the rotary linkage 206 moves from the position of FIG. 8A to the position of FIG. 9A, the bullet 274 slides along the lower portion of the surface 220 of the linkage housing member 210. When the rotary linkage 206 moves into the position of FIG. 10A, however, a portion of the bullet 274 moves into a notch 278 formed in the surface 220 of linkage housing member 210. The notch 278 is located so that it is aligned with the bullet 274 at the moment the ram 128 fully moves the needles 110 to their radially extended position. Once a portion of the bullet 274 enters the notch 278, the rotary linkage 206 is locked against rotation with respect to the linkage housing 204.

Locking the rotary linkage 206 to the linkage housing 204 also locks both the cover driver 162 (and cover 124) and the ram driver 180 (and ram sleeve 128) to the linkage housing 204. The shaft 116 carrying the needles 110 is fixed to the linkage housing 204 via the threads 244 received in the bore 246 in housing member 210. As a result, the relative position of the cover 124, ram sleeve 128, shaft 116 and needles 110 is fixed as soon as the bullet 274 engages the notch 278, i.e., when the needle passer 100 has reached its second stage of actuation (FIGS. 10A and 10B). It will be appreciated by persons skilled in the art that mechanisms other than that illustrated may be used to fix the relative position of the cover 124, ram sleeve 128 and shaft 116 prior to passing the needles 110 through tissue.

Once the needles 110 are ready to be passed through tissue, as shown in FIG. 10A, the mechanism described above for controlling whether depressing the trigger 108 rotates the rotary linkage 206 within the linkage housing 204, or moves the linkage housing 204 and the shaft 116 with respect to the handle 102, is actuated. Depressing the trigger 108 to the extent shown in FIG. 10A seats the bullet 274 in the notch 278 of the linkage housing 204, as described above, and simultaneously moves the lock pin 252 out of engagement with the notch 256 in the linkage housing. This occurs because a slot 280 in the lower wall 260 of the trigger 108 becomes aligned with the lock pin 252 carried by the rail 248. The lock pin 252 is now free to move vertically within the bore 250 of rail 248. The spring 262 biasing the lock pin 252 toward the trigger 108 now moves the end 258 of the lock pin into the trigger slot 280, which moves the other end 254 of the lock pin out of the notch 256 in the linkage housing 204. This frees the linkage housing 204 for movement with respect to the rail 248 and the handle 102.

Figure 11:
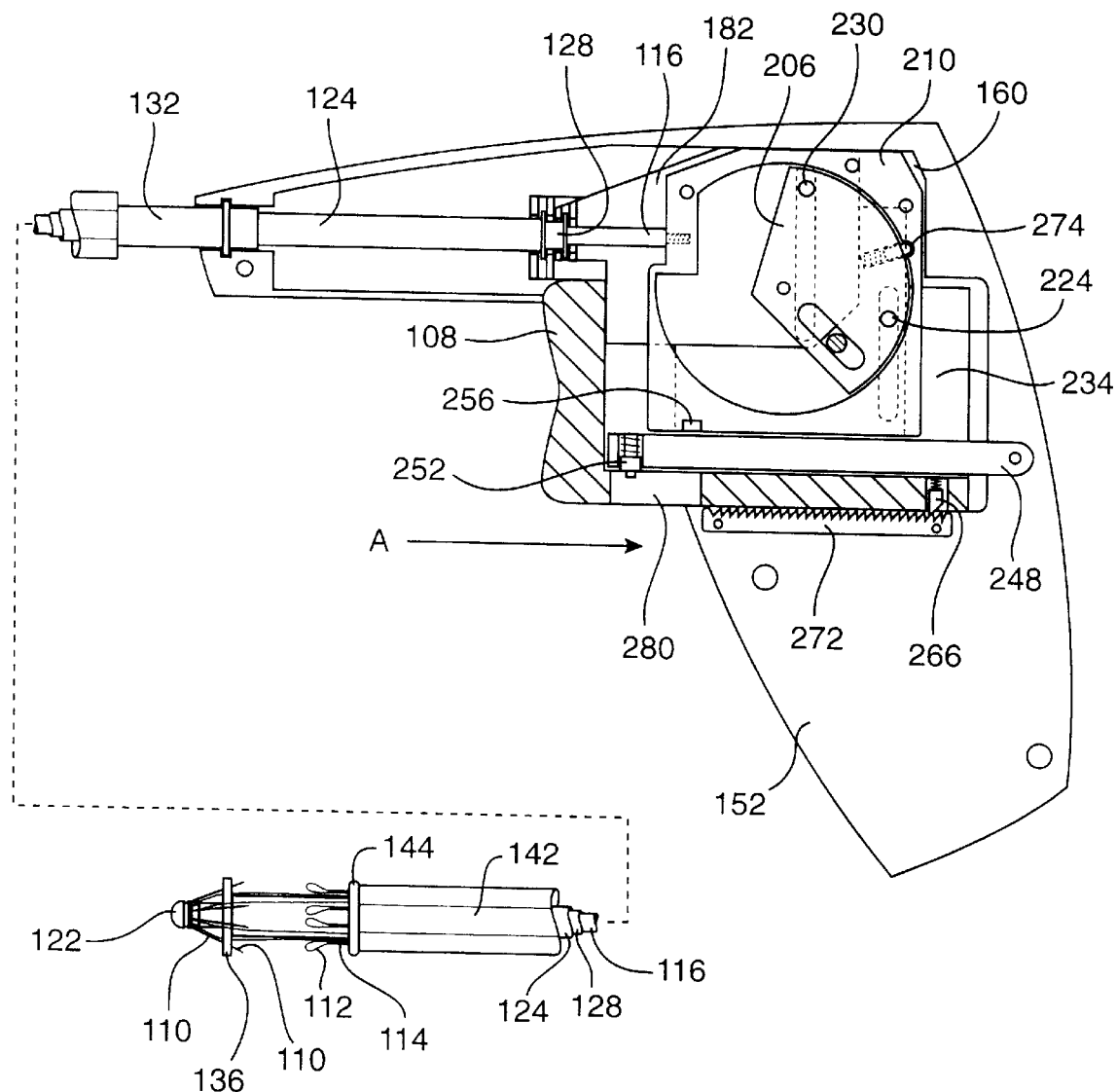
FIG. 11 is a side elevation view of the needle passer shown in FIG. 10A, with the device shown in a third stage of actuation.

Thus, when the trigger 108 is depressed from the position shown in FIG. 10A to the position shown in FIG. 11, the lock pin 252 moves freely within the trigger slot 280. As before, this drives the pin 214 against the slot 242 in the rotary linkage 206, which is now locked against rotation within the linkage housing 204 by the bullet 274 and the notch 278. However, as the linkage housing 204 is no longer locked to the rail 248, depressing the trigger 108 moves the rotary linkage 206 linearly, which in turn moves the linkage housing 204 in the direction of arrow A. This moves the shaft 116 and the needles 110 in the direction of arrow A to pass the needles through tissue. When the needles 110 have reached their fully retracted position shown in FIG. 11, the trigger 108 cannot be further depressed due to the linkage housing 204 abutting the rear wall of the recess 160 in the handle 102. The trigger 108 cannot be moved in the opposite direction due to the pawl 266 engaging ratchet 272. Therefore, the needles 110 are locked in their retracted position upon passing through the tissue.

The various components of the needle passer 100 may be formed of any suitable materials. For example, in a preferred embodiment, the shaft 116 which carries the needles 110, and the ram sleeve 128 are metal, e.g., machined or extruded stainless steel, while the remaining components are plastic, e.g., injection molded polycarbonate or ABS. It should be appreciated that alternative materials may be used if desired. In addition, the needle passer is preferably manufactured as a disposable instrument, although it may comprise one or more reusable portions. For example, the handle and actuator assembly could be reusable and removably coupled to a disposable shaft assembly.

Further, the size and specific configuration of the needle passer 100 may also be varied depending on the application and the user's preferences. In the illustrated and preferred embodiment, the needle passer 100 is designed for use in minimally invasive procedures and is sized and configured to be grasped in one hand and manipulated to pass at least the shaft assembly 104 into a patient through a relatively small (e.g., 3 or 4 inches) port or other access opening. As an example, the height, length and thickness of the handle 102 may be, respectively, 4.195, 4.818 and 0.310 inches. The length and outside diameter of the shaft 116 may be, respectively, 11 and 0.125 inches, while the length, outside diameter and inside diameter of the ram 128 may be, respectively, 9.241, 0.148, and 0.135 inches. The length, outside diameter and inside diameter of the cover 124 may be, respectively, 9.040, 0.168 and 0.156 inches, while the length and outside diameter of the suture tube 132 may be, respectively, 10.25 and 0.396 inches.

In addition, the preferred actuator assembly 106 is constructed so that depressing the trigger 108 from its initial position (FIG. 8A) to its final position (FIG. 11A) results in the shaft 116 moving approximately 0.620", the ram 128 moving approximately 0.375" (i.e., net movement toward the distal end of the needle passer), and the cover 124 moving approximately 0.510". It should be recognized that the preferred size and configuration of the various components are exemplary only and may be varied by persons skilled in the art without departing from the principles of the invention.

The needle passer of the present invention will now be described in connection with one preferred application, namely, carrying out an anastomosis procedure to secure a vascular conduit, such as a blood vessel harvested from a patient's body, to a hollow body structure, such as a patient's aorta. It will be appreciated by persons skilled in the art, however, that this is only one of many possible applications for the needle passer of the invention. Accordingly, the description which follows should not be construed as limiting the environment or procedures in which the needle passer may be utilized.

Further, while in the exemplary, illustrated application the needle passer is utilized with additional devices constructed according to other aspects of the invention, it will be recognized that the devices may be utilized separately to carry out various medical procedures. Similarly, it will be appreciated that the needle passer may be used with additional devices and methods, for example, the devices and methods for performing anastomosis disclosed in co-pending application Ser. No. 08/759,110, filed Dec. 2, 1996 and entitled SURGICAL STAPLING INSTRUMENT AND METHOD, the subject matter of which is incorporated by reference.

Figure 12:
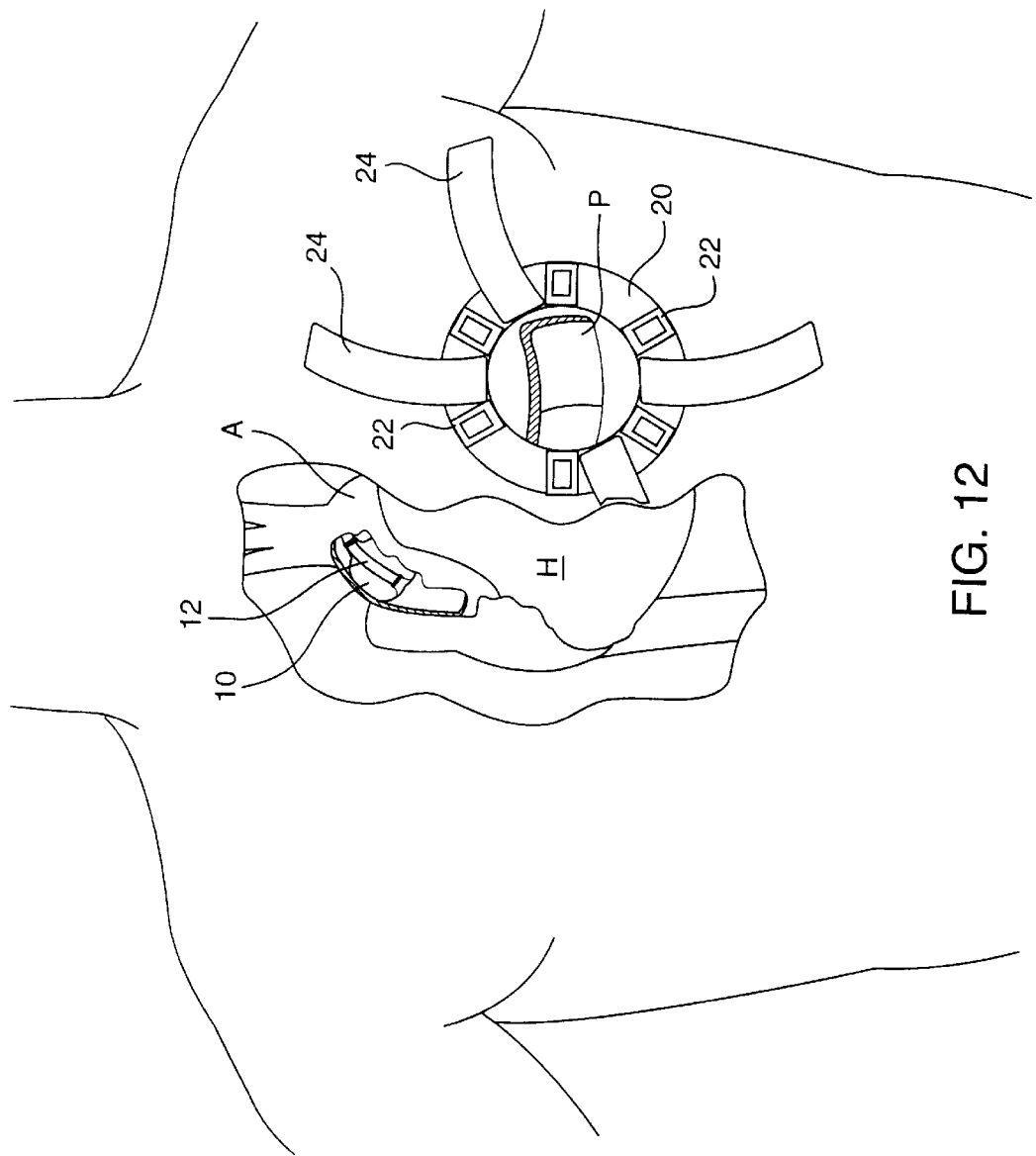
FIG. 12 is a perspective, schematic view of a patient's chest with a port formed therein for carrying out a coronary artery bypass procedure in a minimally invasive manner according to one possible embodiment of the invention, with a portion of the chest wall and a portion of the wall of the aorta broken away for clarity.

Referring now to FIG. 12, a patient's chest is shown with a port P formed in the chest wall, the port preferably passing through an intercostal space defined between adjacent ribs (not shown). The size and location of the port P, however, may be varied from that shown in the Figures. A portion of the patient's chest wall is broken away for clarity to expose the heart H and aorta A, both of which may be accessed through the port P in order to carry out a coronary artery bypass grafting procedure. The aorta A, a portion of which is broken away for clarity, is occluded by an aortic occlusion device comprising an expandable member in the form of a balloon 10 supported by a catheter shaft 12. The aortic occlusion device may be constructed as disclosed in co-pending application Ser. No. 08/782,113, the subject matter of which is hereby incorporated by reference. The aortic occlusion device is used to block the flow of blood through the aorta in order to place the patient on cardiopulmonary bypass (CPB), which may be established, for example, as disclosed in the aforementioned co-pending application, or as disclosed in U.S. Pat. No. 5,584,803, the subject matter of which is hereby incorporated by reference.

In order to provide easier access to the heart H and the aorta A, a retractor (not shown) may be used to spread the opposite sides of the incision forming the port P. A retractor may be used which spreads the patient's ribs and the sides of the incision a sufficient amount to permit the surgeon to visualize the heart and aorta. For example, the retractor disclosed in co-pending, commonly owned application Ser. No. 08/911,877, filed Aug. 15, 1997 and entitled SURGICAL RETRACTOR, the subject matter of which is hereby incorporated by reference, may be positioned in the port P to spread the ribs and lift one side of the incision with respect to the other side of the incision, thereby providing the surgeon ample access to the aorta in order to perform the anastomosis. Alternatively, the needle passer may be used without a retractor by being positioned through the port.

A suture organizer is preferably provided for organizing the suture used to anastomose a vascular conduit to the aorta A. The illustrated organizer is in the form of a ring 20 with a plurality of suture holding areas 22 configured to removably retain suture by any suitable means, e.g., friction, clamps, adhesive, etc. A plurality of tabs 24 extend from the ring 20 and are secured to the patient's chest. The tabs 24 preferably are flexible strips of fabric or other material and carry adhesive for removable attachment to the patient's skin (or a surgical film or drape disposed over the skin). The ring 20 defines a central opening that overlies the port P such that instruments positioned through the port P pass through the ring. This permits easy attachment of suture extending from inside the patient's body and through the port P to the holding areas 22 on the ring 20.

Figure 13:
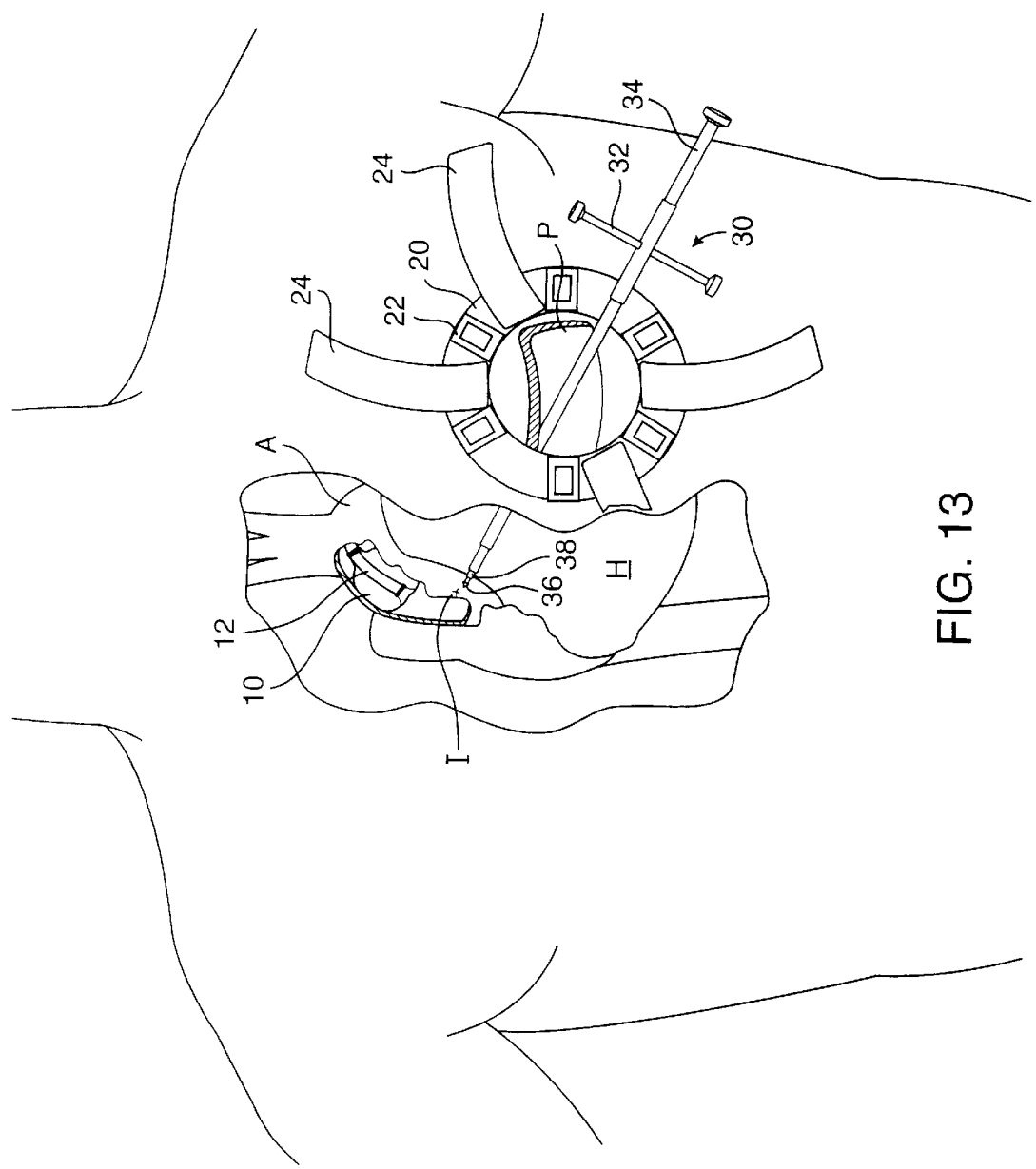
FIG. 13 is a view corresponding to FIG. 12 showing an incision formed in the patient's aorta according to the invention and an aortic punch for forming the incision into an aortotomy.
Figure 14:
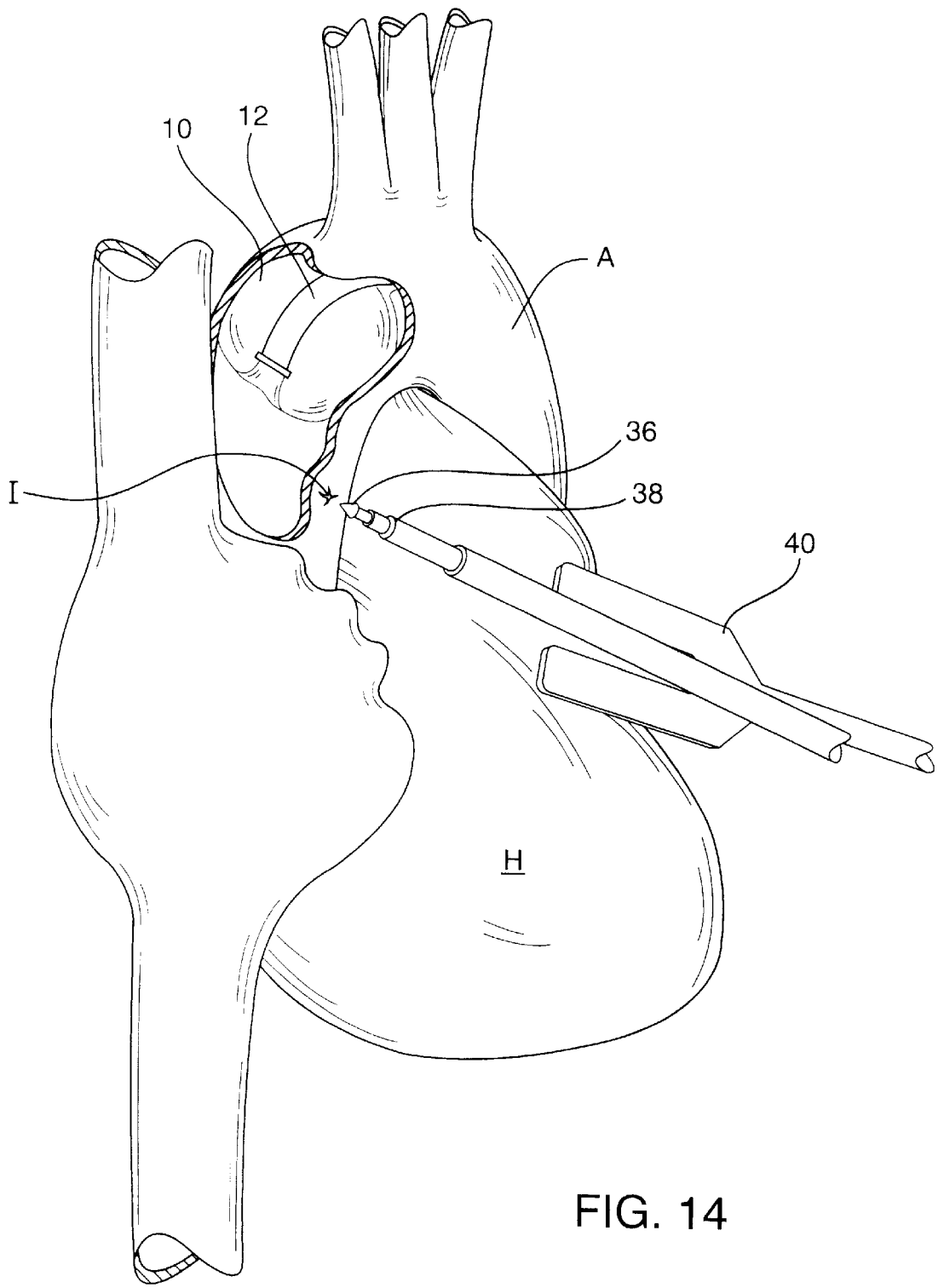
FIG. 14 is an enlarged view of the incision shown in FIG. 13 and an instrument supporting the aortic punch adjacent the incision.
Figure 15B:
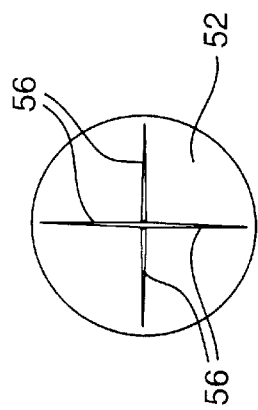
FIGS. 15A and 15B are, respectively, front and end elevation views of a tissue cutting instrument constructed according to a preferred embodiment of the invention.
Figure 15A:
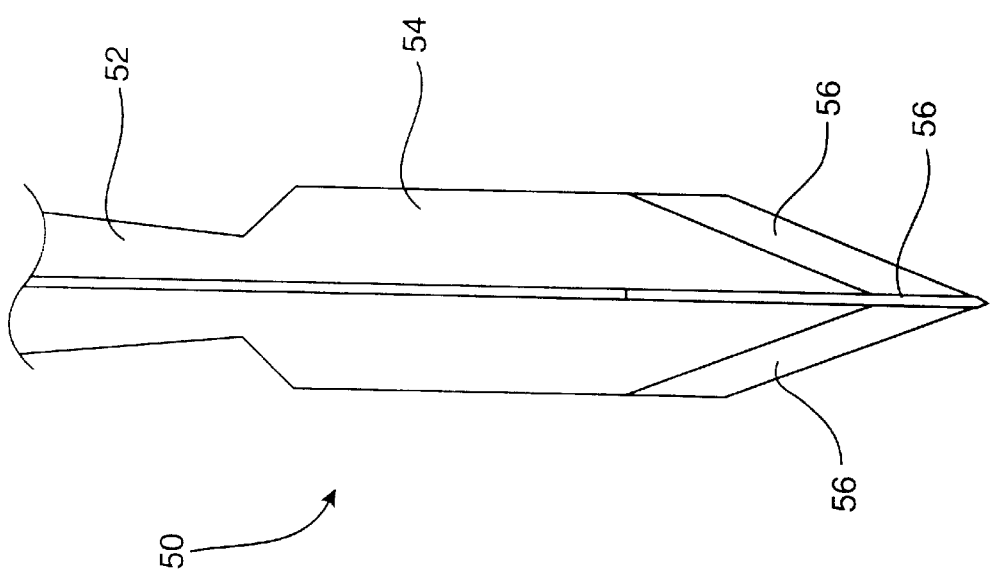

Referring to FIG. 13, an aortic punch 30 is positioned through the port P and includes a handle 32 and an actuator 34. The actuator 34 is depressed to move a punch head 36 with respect to an anvil 38 to cut tissue surrounding the head 36. FIGS. 13 and 14 show the punch head 36 located adjacent an incision I in the wall of the aorta A. The incision is preferably formed by a cutting instrument 50 comprising a plurality of blades 52 supported by a shaft 54, as shown in FIGS. 15A and 15B. The instrument 50 is designed to cut an incision in tissue to provide an opening into a lumen or cavity while minimizing damage to the lumen wall which may be caused, for example, by forming the incision or inserting an instrument through the formed incision.

The blades 52 of the instrument 50 each have a cutting surface 56 which is tapered to a point for cutting through tissue to form an incision I having flaps connected to the tissue at several points. The incision I has increased surface area and additional points of attachment between the flaps and surrounding tissue, as compared to an incision made by a single blade, and thus is less likely to tear along the incision lines. That is, the force exerted on the tissue by inserting an instrument through the incision is distributed over a wider area in an incision formed by the instrument 50 than an incision formed by a single blade. In the illustrated embodiment, the instrument 50 has four blades which form a cut having four flaps; however, it will be appreciated that an alternative number or configuration of blades may be used, for example, three blades.

Figure 16A:
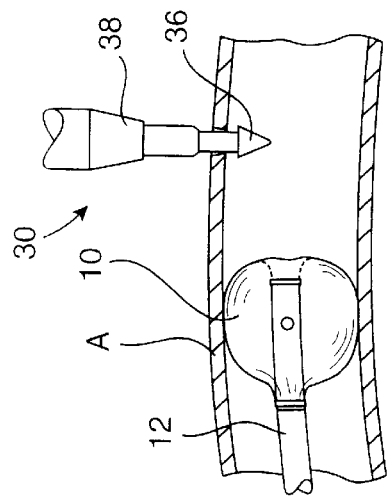
FIGS. 16A–16D are elevation views, partly in section, illustrating forming an incision in the aorta and then forming the incision into an aortotomy.

The cutting instrument 50 is used to form the incision I in the wall of the aorta as shown in FIG. 16A, with the position of the balloon 10 of the endoaortic clamp preferably being monitored by any suitable technique, for example, fluoroscopy or transesophageal echocardiogram (TEE), to ensure that the cutting instrument 50 does not contact the balloon 10. An alternative way to prevent such contact is to secure the position of the balloon in the aorta A. This can be accomplished in various ways, for example, by placing an instrument around the aorta A which engages and holds the balloon 10 in place, or by using an instrument which constricts the aorta between the balloon and the location of the anastomosis to a size that does not permit the balloon to pass. In each case the balloon 10 is prevented from migrating within the aorta A toward the anastomosis area.

Figure 16B:
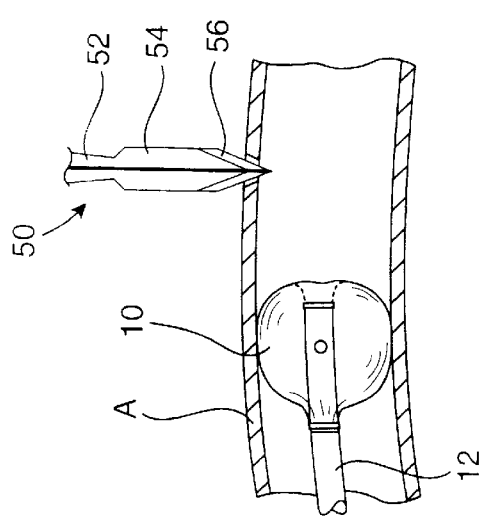
Figure 16C:
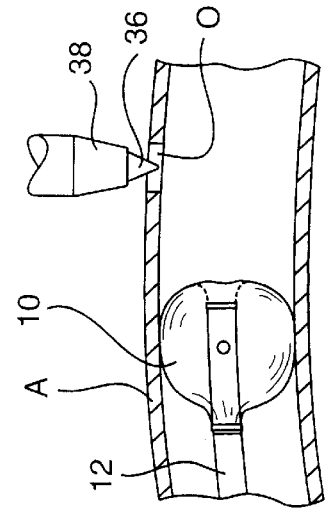
Figure 16D:
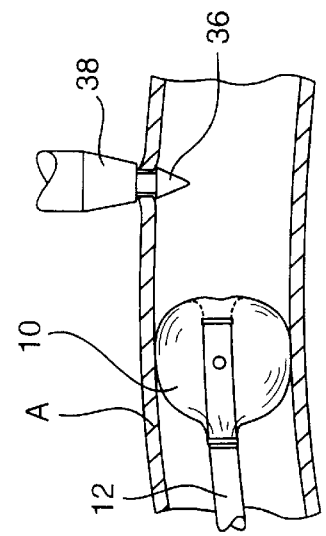

The instrument 50 is used to form the incision I in the wall of the aorta and removed through the port P. The aortic punch 30 is then inserted through the port P and the punch head 36 is positioned next to the incision I. As shown in FIG. 14, the aortic punch 30 may be supported by an instrument 40 resting on the outer wall of the heart H. With reference to FIGS. 16B–16D, the punch head 36 is placed through the incision into the interior of the aorta A with the anvil 38 located just outside the wall of the aorta. The actuator 34 is then depressed with respect to the handle 32 so that the punch head 36 moves into the anvil 38 and cuts through the wall of the aorta. This results in the punch head 36 and anvil 38 cooperating to cut an opening in the wall of the aorta, preferably in the form of a circular aortotomy O configured to be anastomosed to an end of a vascular conduit (not shown in FIGS. 16A–16D).

Figure 17:
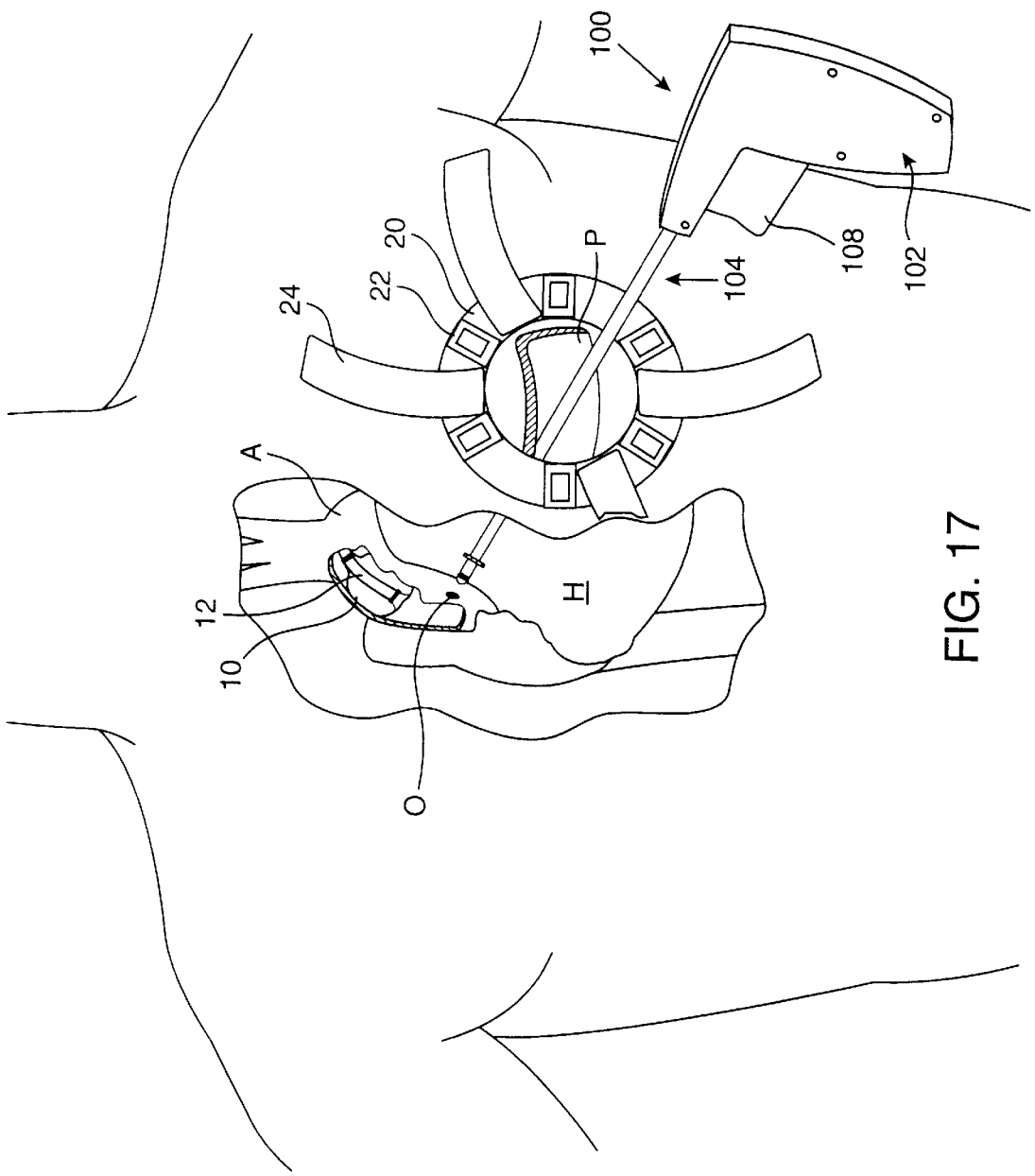
FIG. 17 is a view corresponding to FIG. 12, showing the needle passer illustrated in FIG. 1 prior to its insertion into an aortotomy for carrying out an anastomosis procedure according to one embodiment of the invention.
Figure 18:
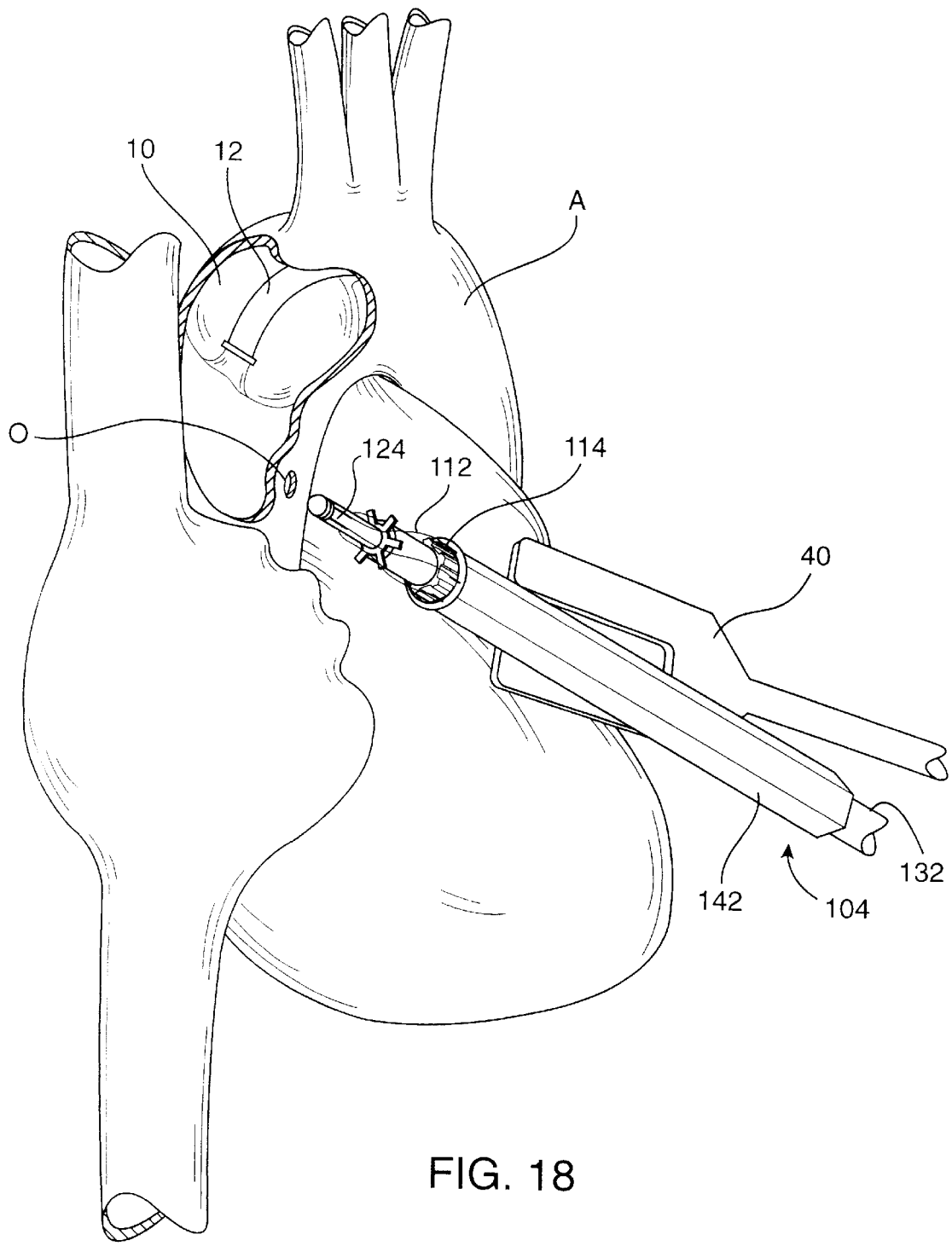
FIG. 18 is an enlarged view of the needle passer shown in FIG. 17 and an instrument supporting the needle passer adjacent the aortotomy.
Figure 19A:
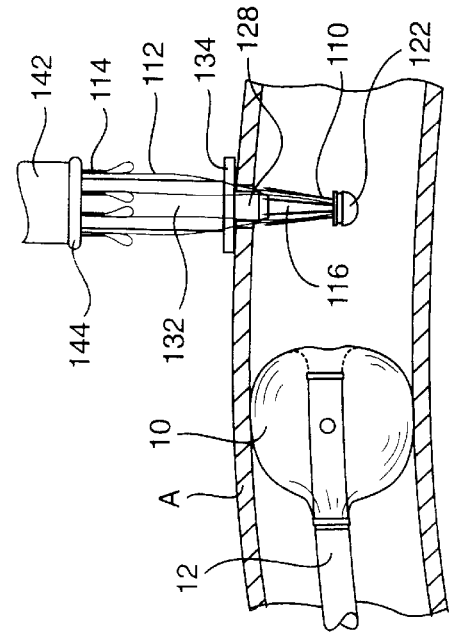
FIGS. 19A–19D are elevation views, partly in section, showing the needle passer illustrated in FIG. 18 being used to pass a first set of needles through the wall of the aorta according to one embodiment of the invention.

In the illustrated application, the needle passer 100 is positioned as shown in FIGS. 17 and 18 so that the shaft assembly 104 extends through the port P to a location adjacent the aortotomy O. The needle passer 100, and in particular the distal end of the shaft assembly 104, may be supported by an instrument 40 resting on the outer wall of the heart H. From this position the needle passer 100 is manipulated to place the distal end of the shaft assembly 104 into the aorta A through the aortotomy O, the foot 134 resting on the outer surface of the aorta as shown in FIG. 19A. In order to ensure that the needle passer 100 does not contact the balloon 10, the position of the balloon within the aorta A is preferably monitored or controlled as described above with respect to the cutting instrument 50.

Figure 19B:
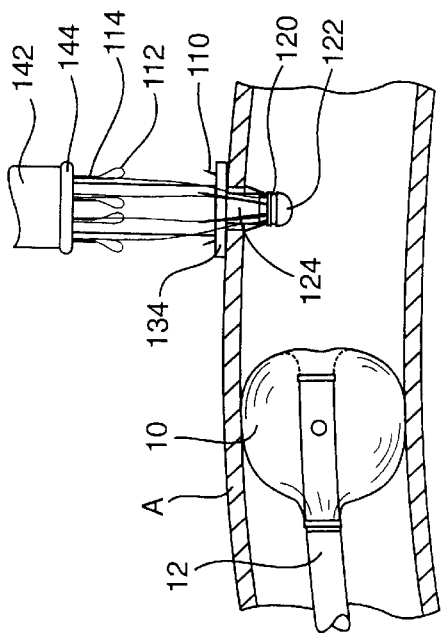
Figure 19C:
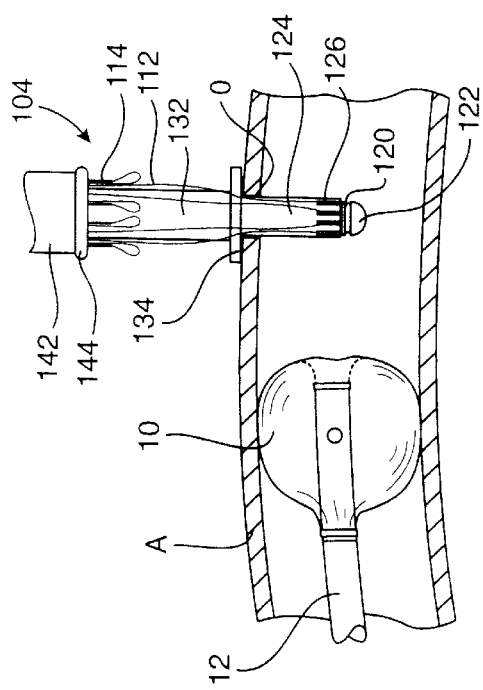
Figure 19D:
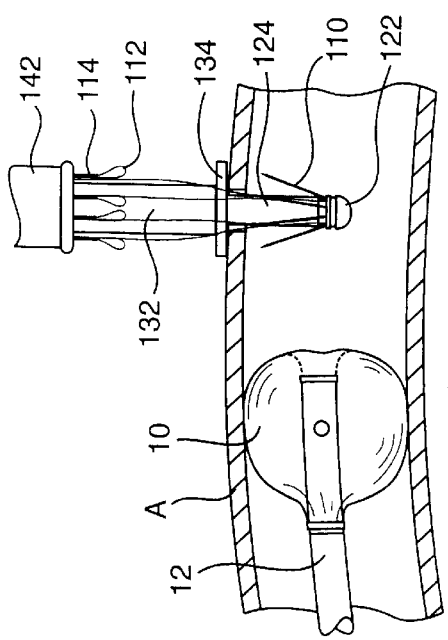

Next, the surgeon actuates the actuator assembly 106 by depressing the trigger 108 which retracts the cover 124 to expose the needles 110, as shown in FIG. 19B. At this point the needles 110 are in their radially non-extended position. As the surgeon continues to depress the trigger 108, the actuator assembly 106 moves the ram sleeve 128 forward to force the needles 110 into their radially extended position, as shown in FIG. 19C. As the surgeon depresses the trigger 108 further, the actuator assembly 106 moves the shaft 116, needles 110 and ram sleeve 128 toward the handle 102, which passes the radially extended needles 110 through the wall of the aorta A, as shown in FIG. 19D. The needles 110 pass through the aorta and between the fingers 136 of the foot 134, with the lengths of suture 112 extending from the second set of needles 114 and through the aortotomy O to needles 110 held in the collar 118 by O-ring 120. The actuator assembly 106 is preferably constructed so that the trigger 108 may be depressed in a continuous, uninterrupted manner to move the shaft assembly from the position shown in FIG. 19A to the position shown in FIG. 19D.

As mentioned above, in order to prevent contact between the needle passer 100 (and in particular the needles 110) and the balloon 10, the position of the balloon within the aorta A may be monitored or controlled. Alternatively, the needle passer 100 may be provided with a mechanism for shielding the needles 110 to prevent contact with the balloon 10. A preferred embodiment of such a mechanism is shown in FIGS. 20A–21C and is indicated by the reference numeral 290.

Figure 20A:
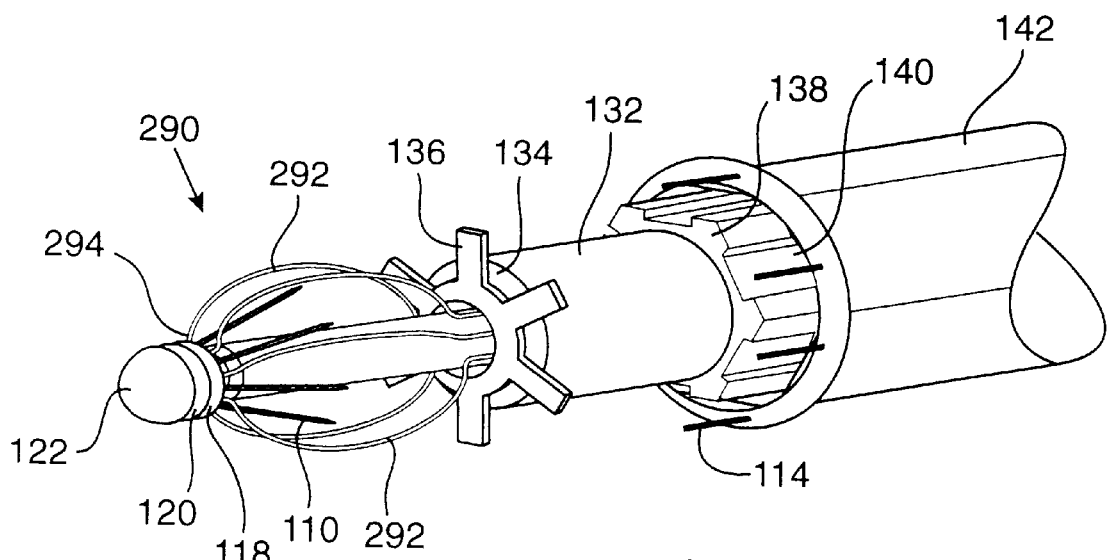
FIGS. 20A and 20B are perspective and end views, respectively, of a portion of the shaft assembly of a needle passer constructed according to another embodiment of the invention which includes a mechanism for shielding the needles.
Figure 20B:
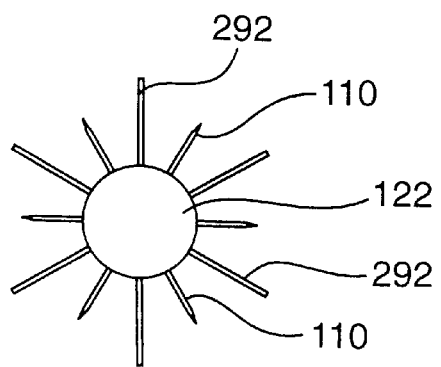

Referring to FIG. 20A, in which the sutures 112 have been omitted for clarity, the needle shielding mechanism 290 comprises a plurality of flexible struts 292 positioned around the needles 110 in a spaced manner. Each strut 292 has one end 294 fixed to the collar 118 and an opposite end 296 fixed to the ram sleeve 128. The cover 124, shown retracted in FIG. 20A, is disposed over the struts 292. When the ram sleeve 128 is in its retracted position, the struts 292 are generally straight and, in the illustrated embodiment, extend in a radial direction so as to be generally coextensive with the needles. If desired, however, the mechanism 290 may be constructed so that the struts 292 extend beyond the needles 110 when the needles are in their radially non-extended position. As the ram sleeve 128 is moved forward to force the needles 110 into their radially extended position, as shown in FIGS. 20A and 20B, the ends 294, 296 of each strut 290 are brought toward each other, which results in the struts 292 flexing outward beyond the needles 110. The struts 292 are preferably formed of a superelastic material, such as nitinol, however, other resilient and flexible metals or polymers may be used. Similarly, while the preferred embodiment includes six struts spaced evenly around the needles 110, any number or configuration of struts may be used.

FIG. 21A shows the shaft assembly of the needle passer of FIG. 20A located in a patient's aorta A adjacent the balloon 10 of an occlusion catheter, with the cover 124 retracted and the needles 110 in their radially non-extended position. FIG. 21B shows the shaft assembly after the ram sleeve 128 has been moved forward to force the needles 110 into their radially extended position. Such movement of the ram sleeve 128 causes the struts 292 to flex outwardly so that they substantially surround the needles 110. Thus, if the balloon 10 should move toward the needle passer (or vice-versa), the balloon would contact the struts 292 of the shielding mechanism 290, and not the needles 110. Further, as shown in FIG. 21C, as the needles 110 are retracted and passed through the wall of the aorta the struts 292 continue to flex so that the balloon 10 cannot contact the needles 110. Accordingly, the balloon 10 is prevented from contacting the needles 110 from the time the needles are moved to their radially extended position until the tips of the needles have passed through the tissue.

The illustrated mechanism 290 for shielding the needles from the balloon is only one possible means for preventing contact between the balloon and needles. For example, rather than utilizing the ram sleeve 128 to expand the struts 292, the struts could be attached to the cover 124 so that they expand upon retracting the cover. Alternatively, the struts 292 could be formed of a superelastic material so that the struts expand around the needles as soon as the cover 124 is retracted. Another possible construction includes springs (not shown) that force the struts 292 into their expanded configuration as soon as the cover 124 is retracted. It will be recognized by persons skilled in the art that other needle shielding mechanisms could also be used.

Figures 22A, 22B:
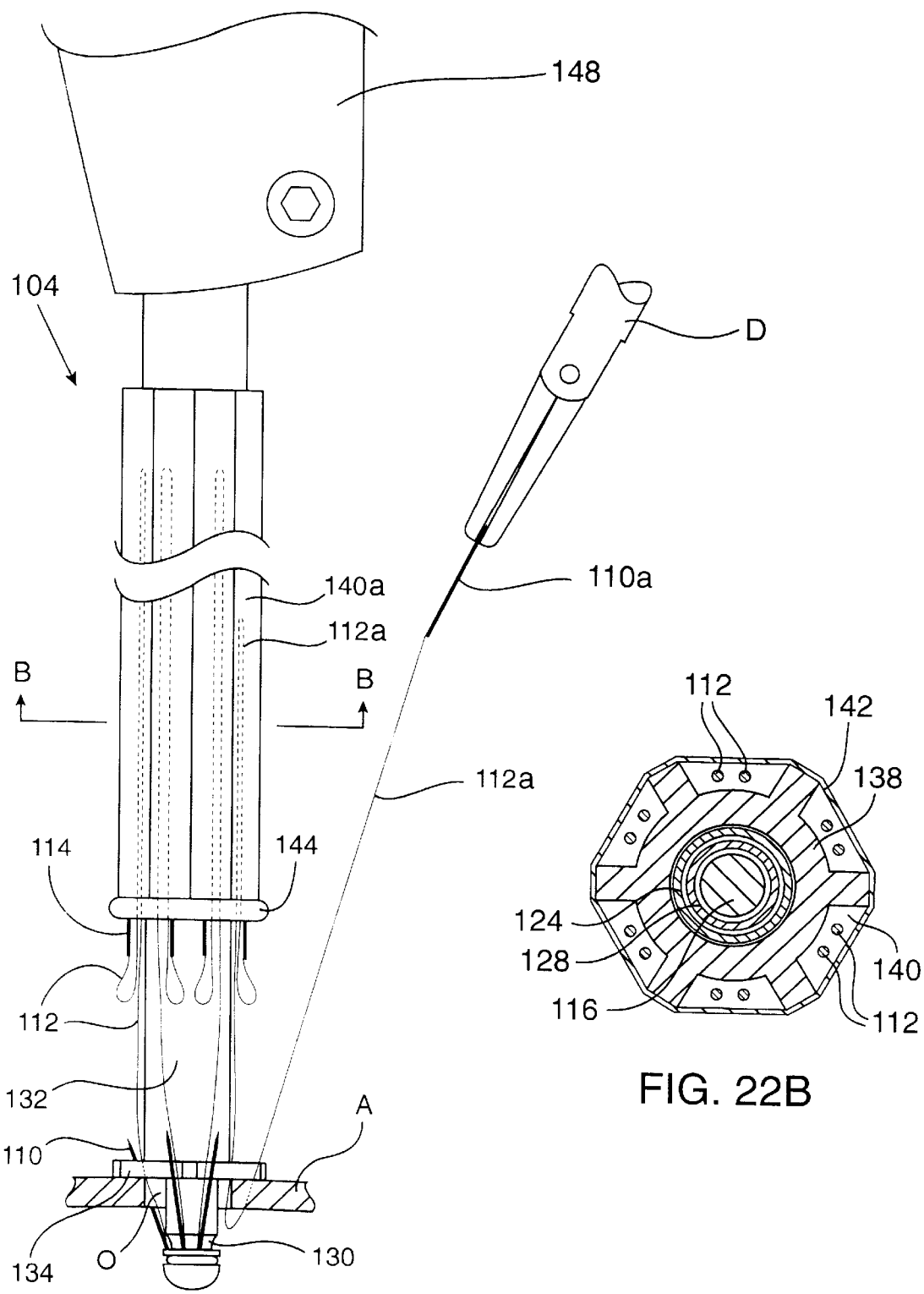
FIG. 22A is an enlarged view of the needle passer shown in FIG. 19D, illustrating a needle being removed from the needle passer to thread a length of suture through the aortotomy and tissue surrounding the aortotomy.
FIG. 22B is a sectional view of the needle passer shown in FIG. 22A, taken along lines B—B in FIG. 22A.

Referring again to FIG. 19D, the needle passer 100 is shown after the needles 110 have been passed through the wall of the aorta. FIG. 22A illustrates the next step wherein one of the needles, 110a, has been pulled completely through the aorta, for example, by a needle driver D. The needle 110a is pulled through the tissue and away from the aorta which threads one of the lengths of suture, 112a, through the aorta at an area spaced from the aortotomy. As the needle 110a is pulled away from the aorta, the length of suture 112a uncoils within one of the suture retaining channels, 140a, as can be seen from FIG. 22A. While each suture length 112 is disposed in a single loop in a channel 140 (FIG. 22B), it will be recognized that the suture may be any size and coiled in any desired manner.

Figure 23:
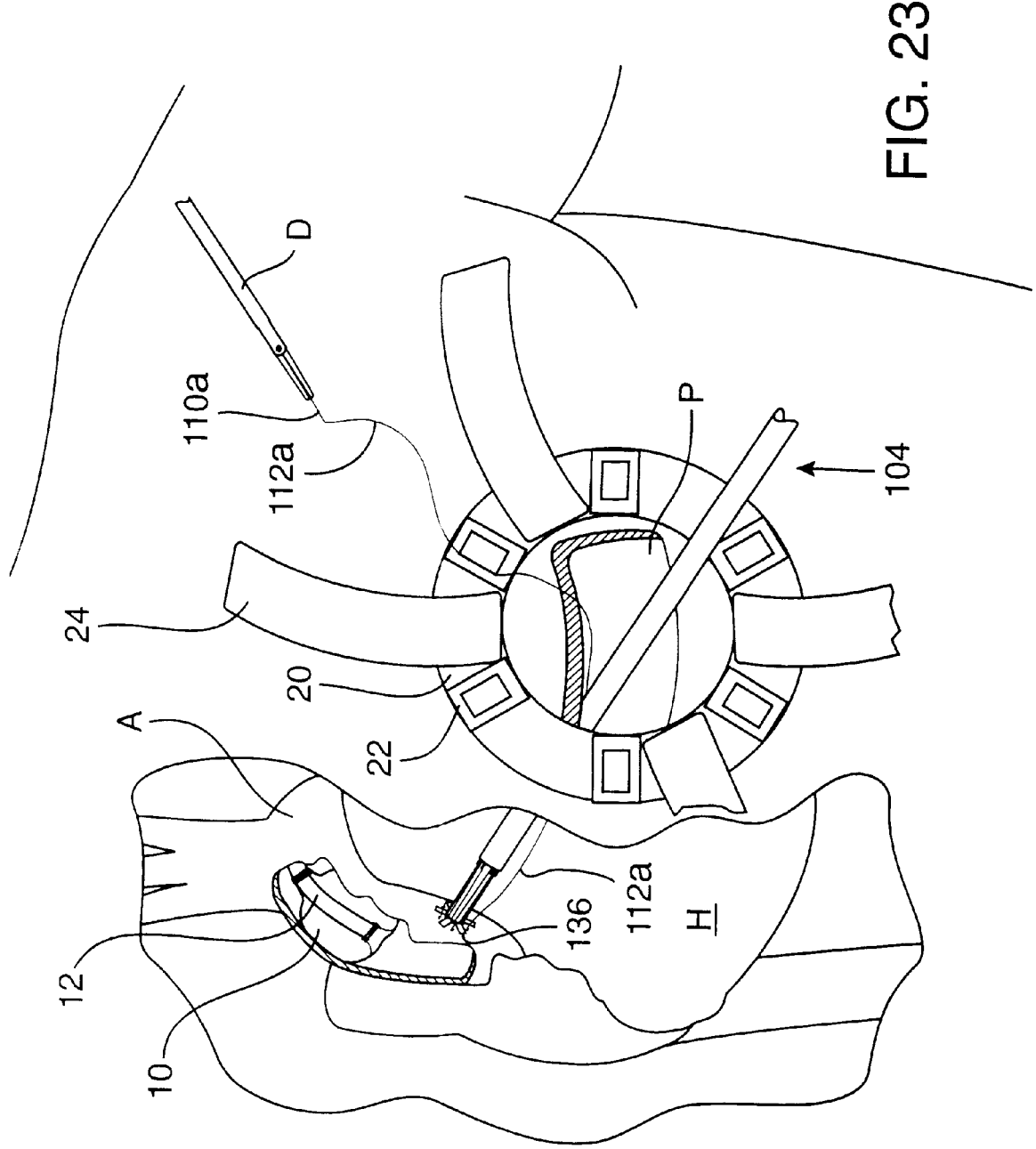
FIG. 23 is a perspective view of the needle passer shown in FIG. 22A, illustrating the length of suture carried by the removed needle being secured to a suture organizer.
Figure 24:
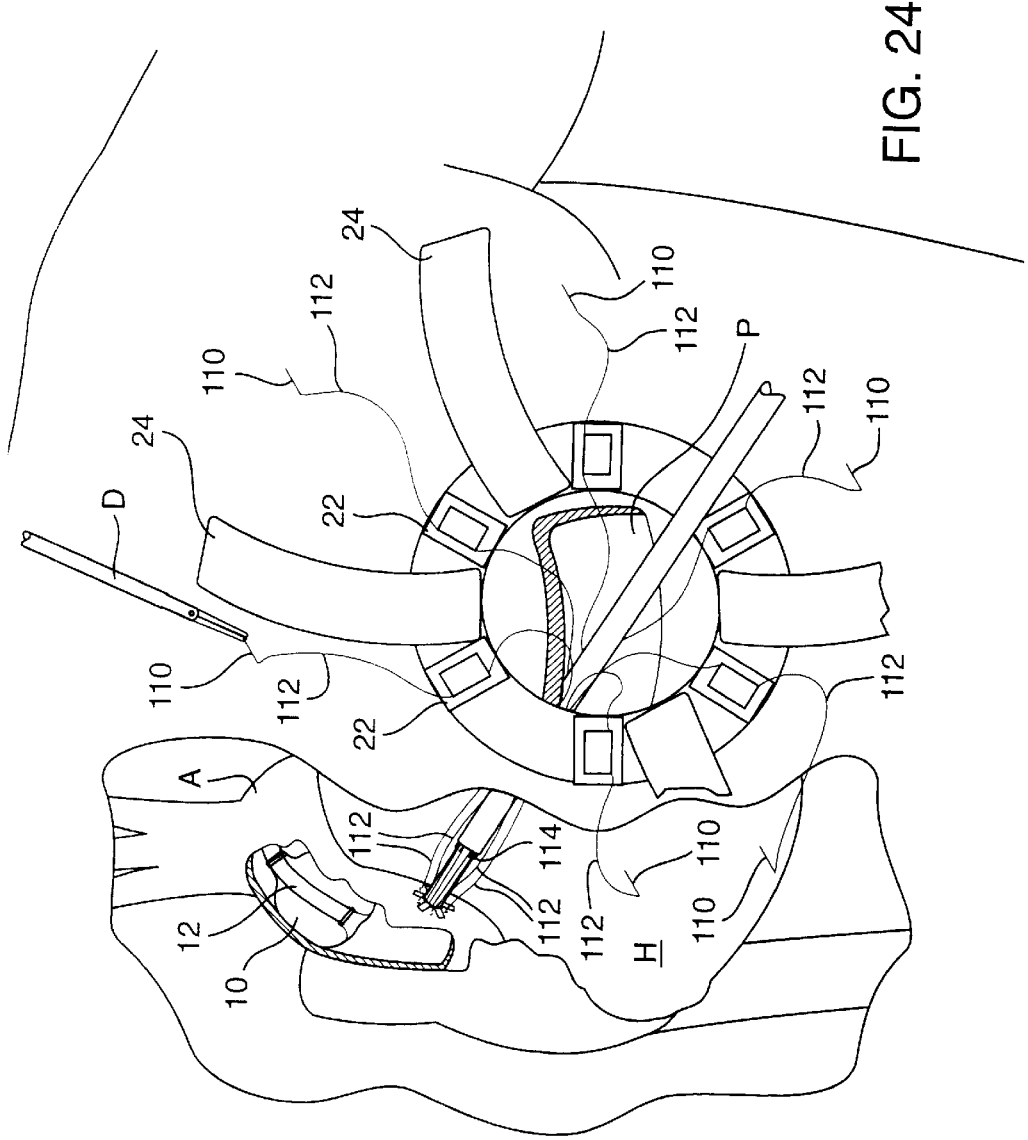
FIG. 24 is a perspective view of the needle passer shown in FIG. 23 after all the needles have been removed and the lengths of suture placed in the suture organizer.

FIG. 23 shows the configuration after the needle 110a has been removed from the patient's body through port P and the length of suture 112a arried by the needle has been secured to one of the suture holding areas 22 of the suture organizer 20. The remaining needles 110 are held by the shaft assembly 104 with their tips projecting out of the tissue adjacent the aortotomy. In the preferred embodiment, the needles 110 are circumferentially disposed around the aortotomy; however, the needles could be anranged in a different configuration. The steps of pulling each needle 110 through the aorta A and removing it from the patient's body through the port P, and then securing the length of suture 112 carried by the needle to a holding area 22 of suture organizer 20, are repeated for each needle 110. Upon completion of these steps, the suture lengths 112 are configured as shown in FIG. 24. Each suture length 112 has one end secured to one of the needles 114 and one end secured to a needle 110. The portion of each suture length 112 between the needles 110 and 114 passes between the fingers 136 of foot 134 and through the wall of the aorta, and then out of the aorta through the aortotomy.

Figure 25:
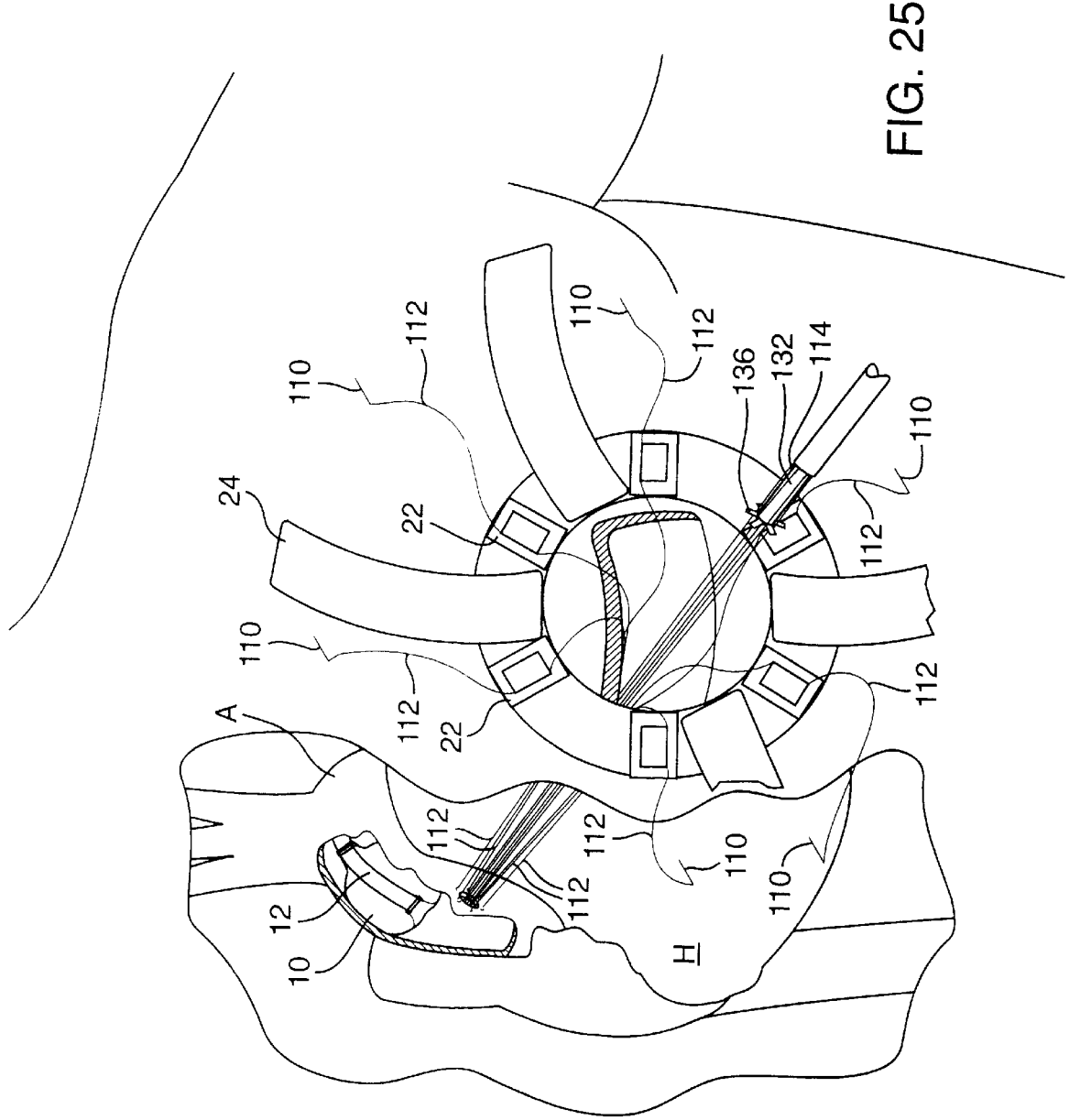
FIG. 25 is a perspective view of the needle passer shown in FIG. 24, illustrating withdrawing the needle passer through the port in the patient's chest wall with the lengths of suture extending from the needle passer, through the aortotomy, and through the wall of the aorta back to the needle passer.

FIG. 25 shows the needle passer 100 being pulled away from the aorta until it has passed through the port P and is located outside the patient's body. As each suture length 112 has one end held in the suture organizer 20 and the other end held by the shaft assembly 104, moving the needle passer 100 away from the patient's body causes each suture length 112 to uncoil within a channel 140 of the suture tube 132 (FIGS. 22A, 22B). In the resulting configuration, the suture lengths 112 extend from the needle passer 100 down to the aorta A, and then from the aorta up to the suture organizer 20, as shown in FIG. 25.

Figure 26:
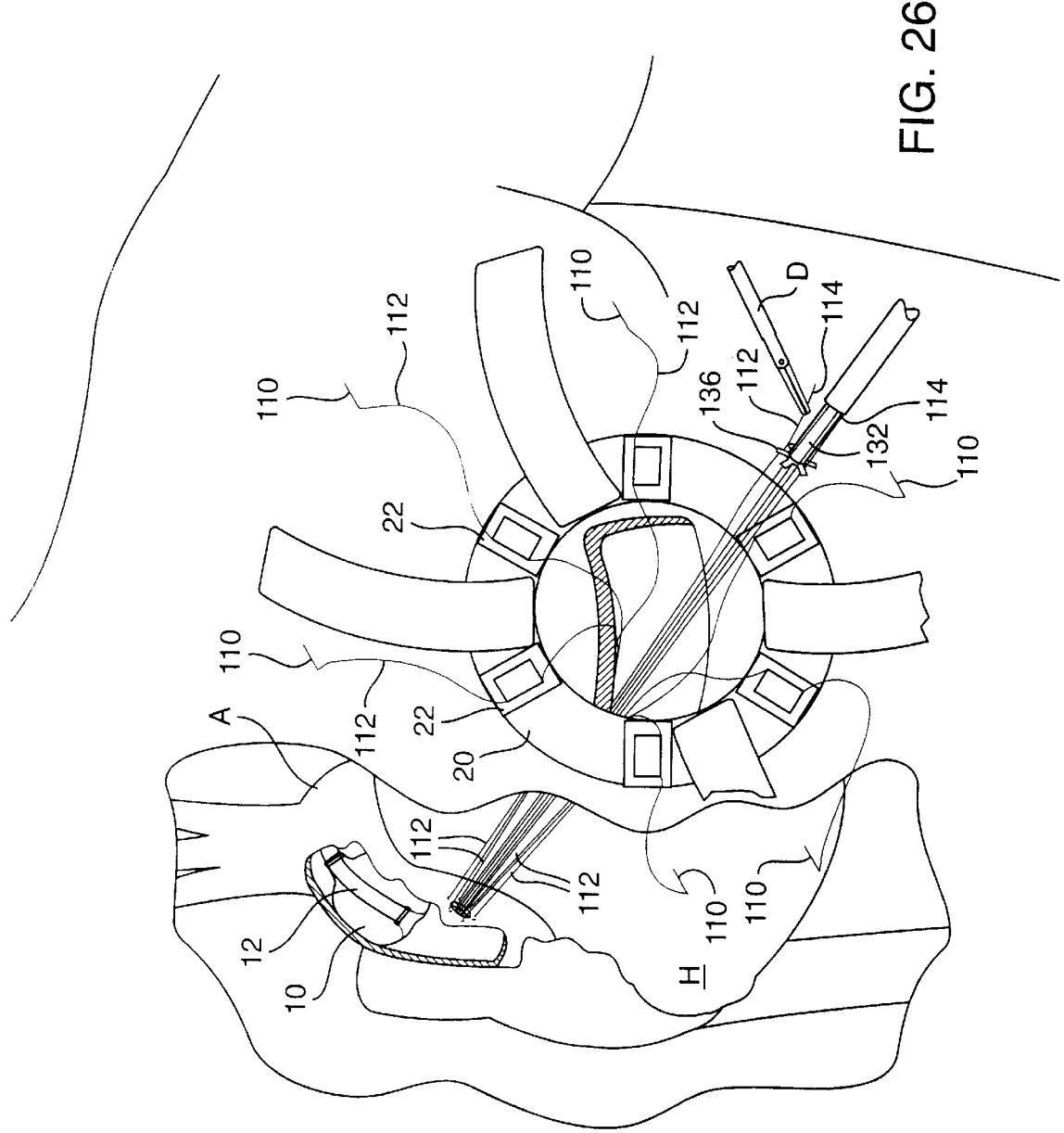
FIG. 26 is a perspective view of the needle passer shown in FIG. 25, illustrating removing a needle from a second set of needles carried by the needle passer, the second set of needles being secured to the ends of the lengths of suture opposite the ends held by the suture organizer.

Upon reaching the position shown in FIG. 25, each needle 114 is removed from the needle passer 100, for example, by using a needle driver D, as shown in FIG. 26. After the needles 114 have been removed from the needle passer 100, both ends of each suture length 112 are disposed outside the patient's body, which permits easier manipulation of the suture in carrying out the anastomosis of a vascular conduit to the aorta A.

A delivery device constructed according to the present invention is preferably used at this point in the procedure to deliver the vascular conduit to the aorta. The delivery device comprises first and second components mounted to each other so as to be relatively movable. One of the first and second components of the device removably carries the vascular conduit, while the other component holds the needles 114 so that each needle passes through an end of the conduit. The first and second components are then moved relative to each other to slide the conduit along the lengths of suture.

Figure 27:
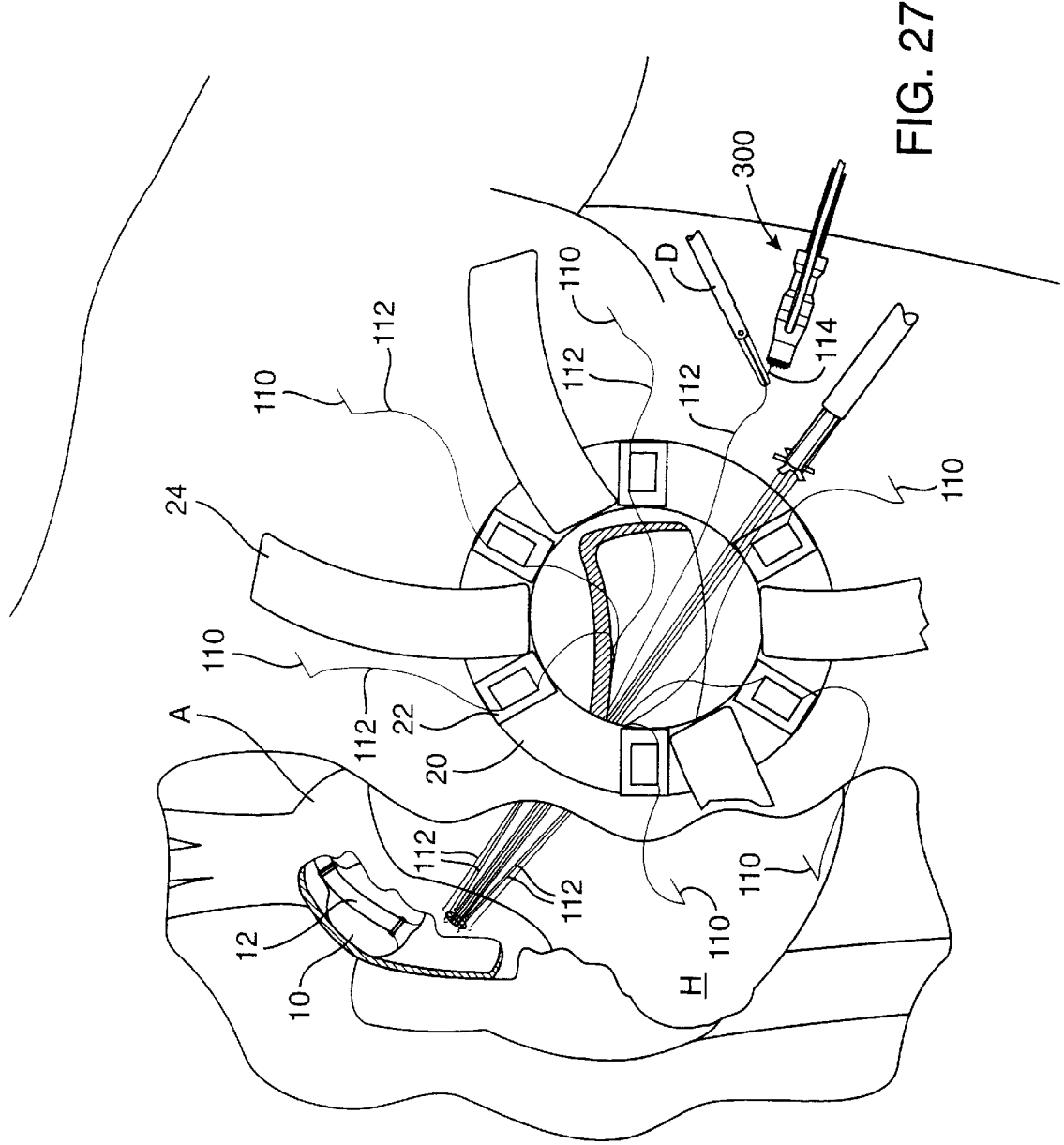
FIG. 27 is a perspective view of the needle passer shown in FIG. 26, illustrating placing the removed needle in a delivery device for delivering a member adapted to be secured to body tissue of a patient.
Figure 28A:
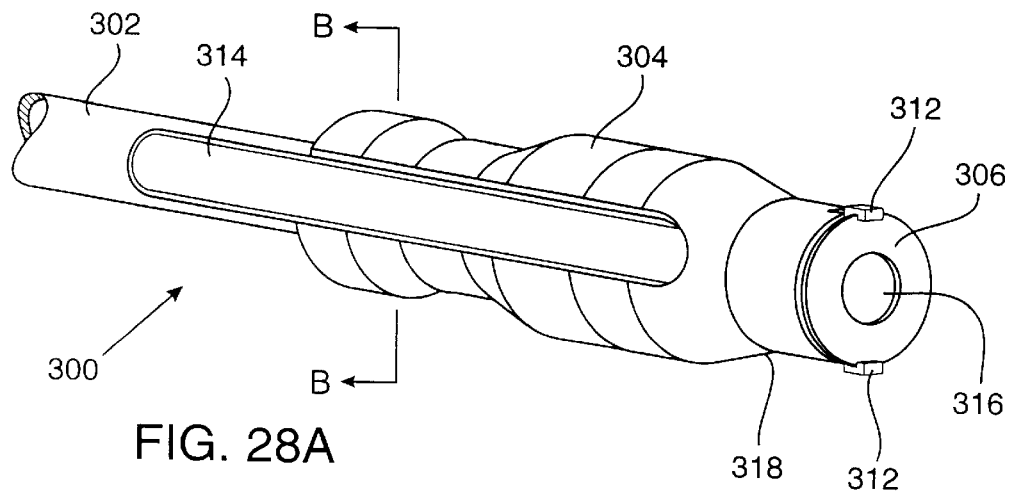
FIG. 28A is a perspective view of the delivery device shown in FIG. 27.
Figure 28B:
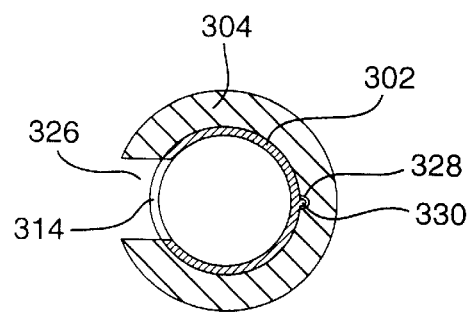
FIG. 28B is a sectional view of the delivery device shown in FIG. 28A, taken along lines B—B in FIG. 28A.
Figure 29:
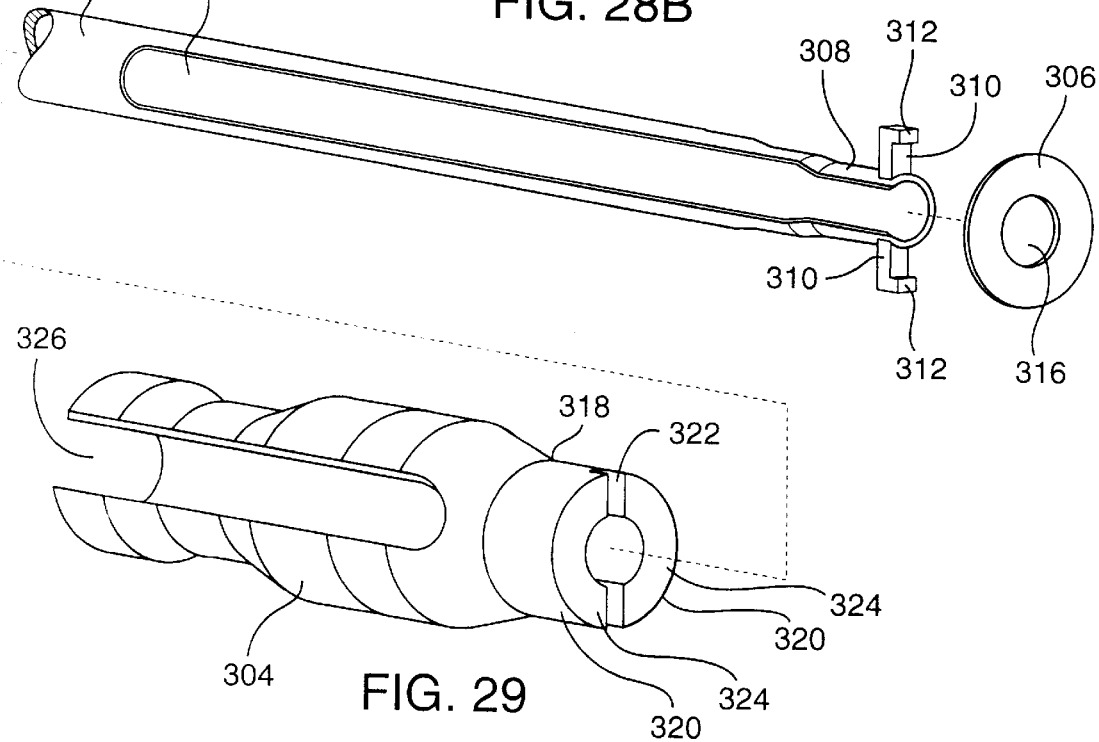
FIG. 29 is an exploded perspective view of the delivery device shown in FIG. 28A.

FIG. 27 illustrates one of the needles 114 being placed into one preferred embodiment of the delivery device of the invention, indicated by reference numeral 300 in the Figures. As shown in FIGS. 28A, 28B and 29, the delivery device 300 comprises a first component in the form of an elongated shaft 302 for supporting a vascular conduit, and a second component in the form of a collar 304 for holding the needles passing through the conduit. The collar 304 is mounted to the shaft 302 so that the components are relatively slidable. The shaft 302 is formed of any suitable material, e.g., stainless steel, and is configured to hold a vascular conduit so that an end of the conduit is located against the collar 304. The needles 114 are removed from the needle passer 100 and placed through the conduit and into the collar 304. The shaft 302 is then moved relative to the collar to deliver the conduit to the aorta.

According to the invention, a sealing element is provided for use in enhancing the seal formed at the anastomosis between the vascular conduit C and the aorta A. In the preferred embodiment, a sealing element 306 is used with the delivery device 300. As shown in FIGS. 28A and 29, the shaft 302 has a proximal end (which may be in the form of a handle, not shown) and a distal end 308 adapted to support the sealing element 306. The distal end 308 is provided with a flange or similar structure which supports the sealing element 306, for example, two arms 310 which extend from the distal end 308 and have upstanding ends 312 to retain the sealing element 306 on the shaft 302. The illustrated delivery device 300 is designed to deliver a vascular conduit to the aorta and, to that end, the shaft 302 has a hollow interior for receiving the conduit. The shaft 302 also has a cut-out portion 314 through which the vascular conduit may be inserted into the shaft, and then moved through an opening 316 passing through the sealing element 306.

The preferred collar 304 is a tubular member formed of any suitable material, e.g., injection molded plastic, having an internal bore that engages the outer surface of the shaft 302 in a slight friction fit for controlled relative movement of the two components. The collar 304 has a distal end 318 which defines two portions 320 separated by a slot 322 configured to receive the arms 310 at the distal end 308 of the shaft 302. The portions 320 define areas 324 for receiving needles that are passed through the end of a vascular conduit and, in the preferred embodiment, the sealing element 306 carried by the shaft 302. The collar 304 also has a cut-out portion 326 which aligns with the cut-out portion 314 of the shaft 302. The needle receiving areas 324, or alternatively the entire distal end 318 or the entire collar 304, is preferably formed of a material which can be penetrated by the ends of the needles. For example, the two portions 320 may be formed of urethane, silicone, cork, rubber or another elastomer capable of releasably retaining the needles that carry suture for securing the conduit to the aorta. Alternatively or in addition to using a material that is penetrable by and capable of holding the needles, positive locking structures for holding the needles may be used. For example, the collar 304 may be provided with spring coils, wedge-shaped openings, clamps, magnetic elements, etc.

The delivery device 300 preferably is provided with means for preventing or limiting relative rotation of the shaft 302 and collar 304. In the preferred embodiment, the shaft 302 has a guide element 328 received in a slot 330 formed in the collar 304 (FIG. 28B). Other suitable means for preventing relative rotation of the shaft 302 and collar 304 include forming the components with mating noncircular cross-sections, a cooperating key and keyway, etc. While in the preferred construction relative rotation of the shaft 302 and collar 304 is prevented, it will be appreciated that the components could be formed to allow limited or complete relative rotation.

Figure 30A:
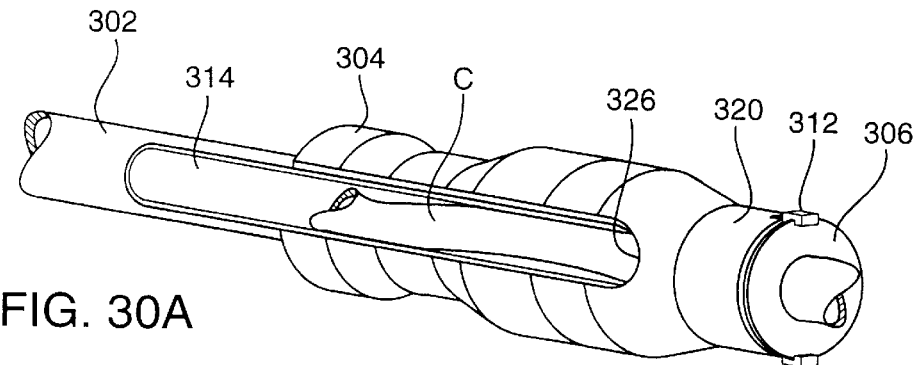
FIG. 30A is a perspective view of a vascular conduit positioned in the delivery device shown in FIG. 28A.
Figure 30B:
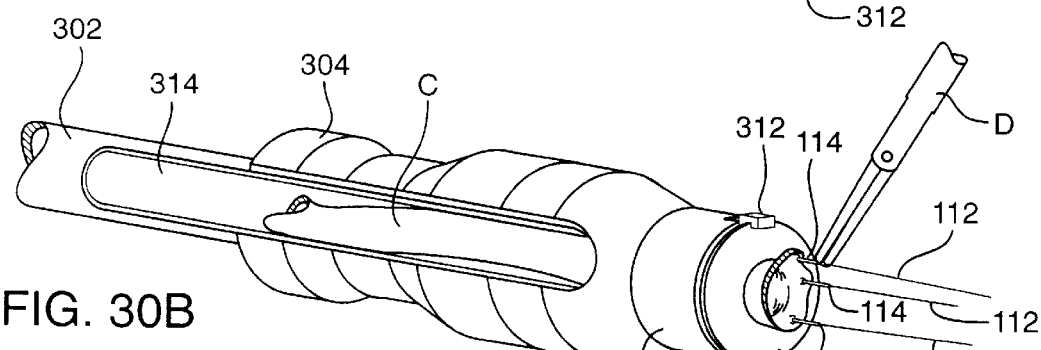
FIGS. 30B and 30C are perspective views showing, respectively, placing needles from the second set through the end of the vascular conduit and into the delivery device shown in FIG. 30A, and the configuration when all of the needles have been placed through the end of the vascular conduit.
Figure 30C:
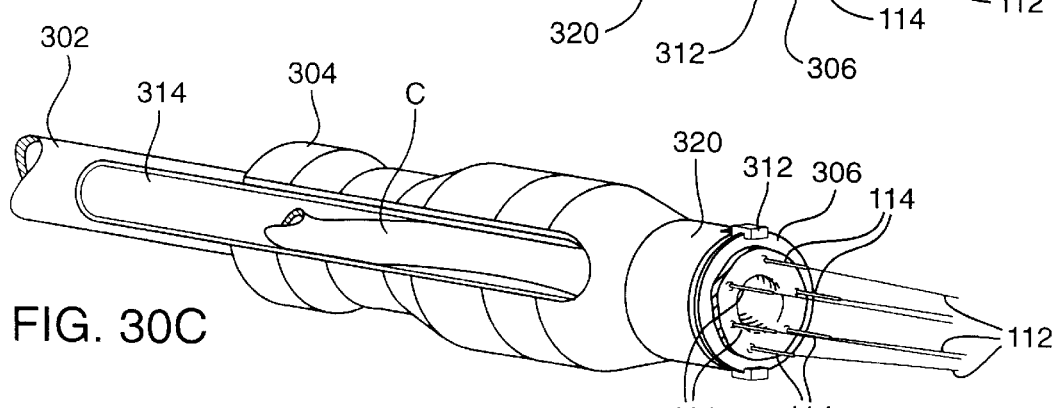
Figure 30D:
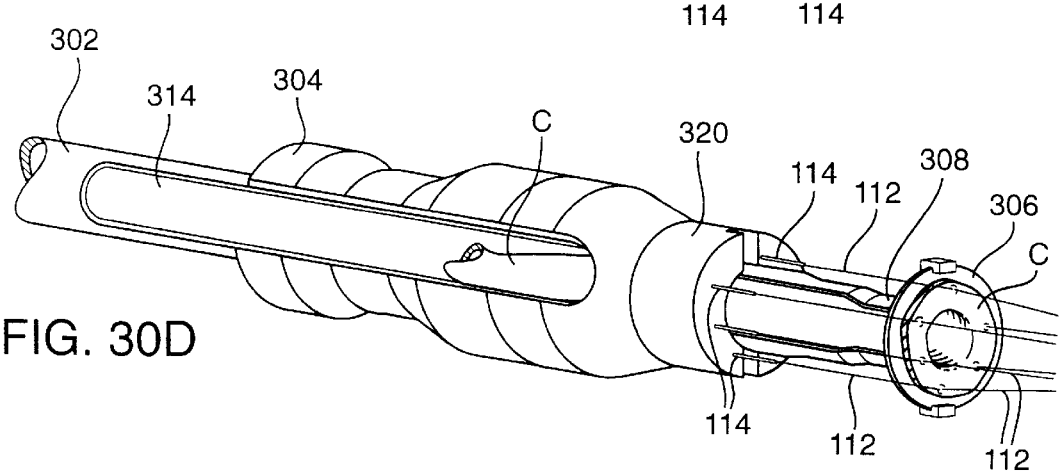
FIG. 30D is a perspective view illustrating the delivery device shown in FIG. 30C being used to move the vascular conduit along the lengths of suture.

FIGS. 30A–30D illustrate a preferred sequence of steps that are performed in using the delivery device 300 to deliver a vascular conduit C along the lengths of suture 112. As shown in FIG. 30A, the vascular conduit C is positioned within the shaft 302 such that the end of the conduit projects out of the shaft distal end 308 and out of the bore 316 of sealing element 306. As shown in FIG. 30B, the needles 114 are placed one by one through the interior of the conduit C and the sealing element 306 so as to extend into the areas 324 of the collar 304. By placing the needles 114 first through the interior of the end of the conduit C, the end of the conduit is everted against the sealing element 306, as shown in FIG. 30C. In an alternative construction, the sealing element 306 has upstanding prongs or barbs (not shown) which penetrate the end of the conduit to hold it in an everted position. After all of the needles 114 have been inserted through the conduit and into the collar 304, relative movement is imparted to the shaft 302 and collar 304. As shown in FIG. 30D, the collar may be maintained stationary while the shaft 302 is moved forward to slide the conduit C and sealing element 306 along the suture lengths 112, the needles 114 remaining in the collar 304 as shown.

Figure 31:
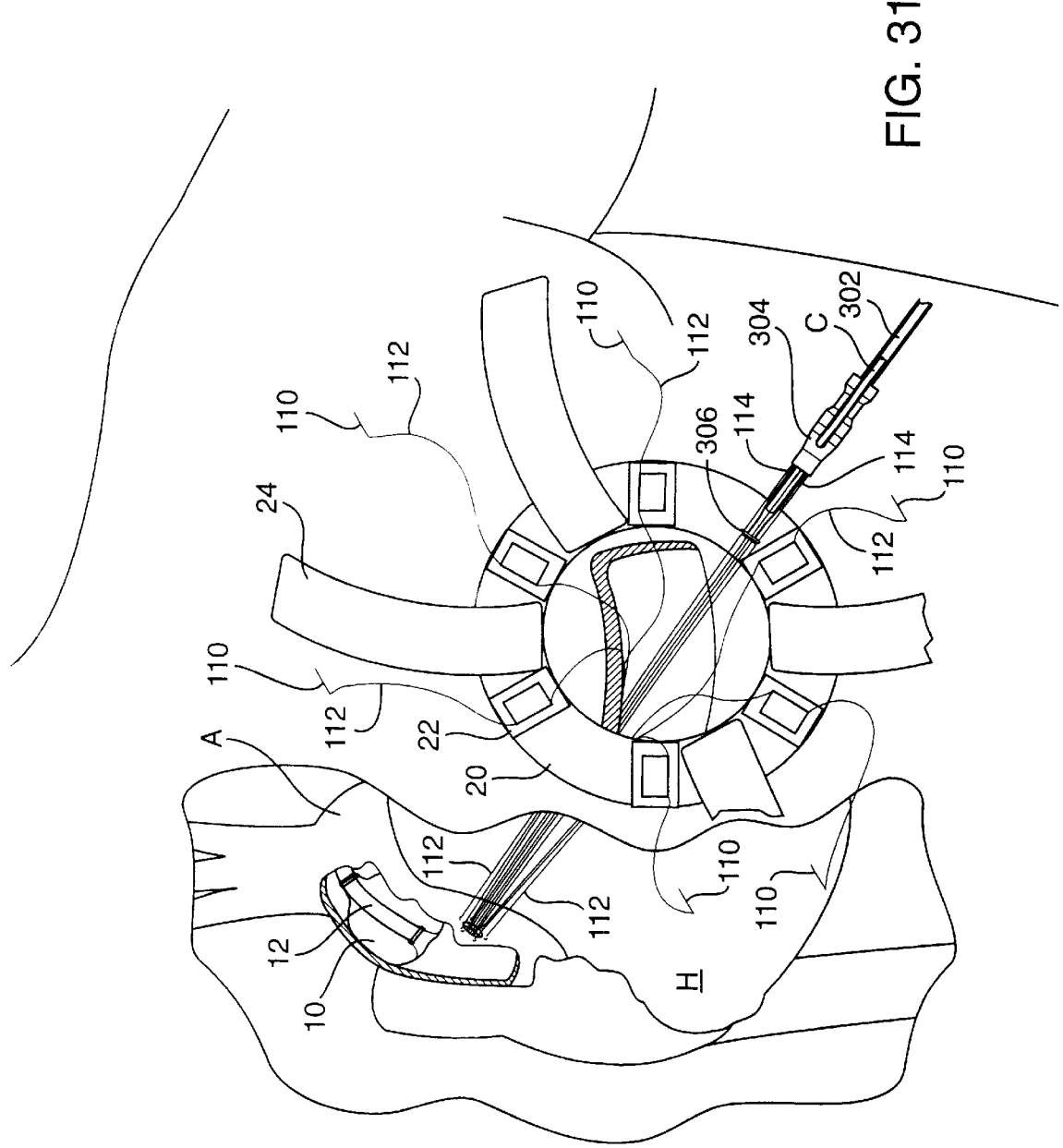
FIG. 31 is a perspective view illustrating the delivery device shown in FIG. 30D being used to move the vascular conduit toward the aorta along the lengths of suture.
Figure 32:
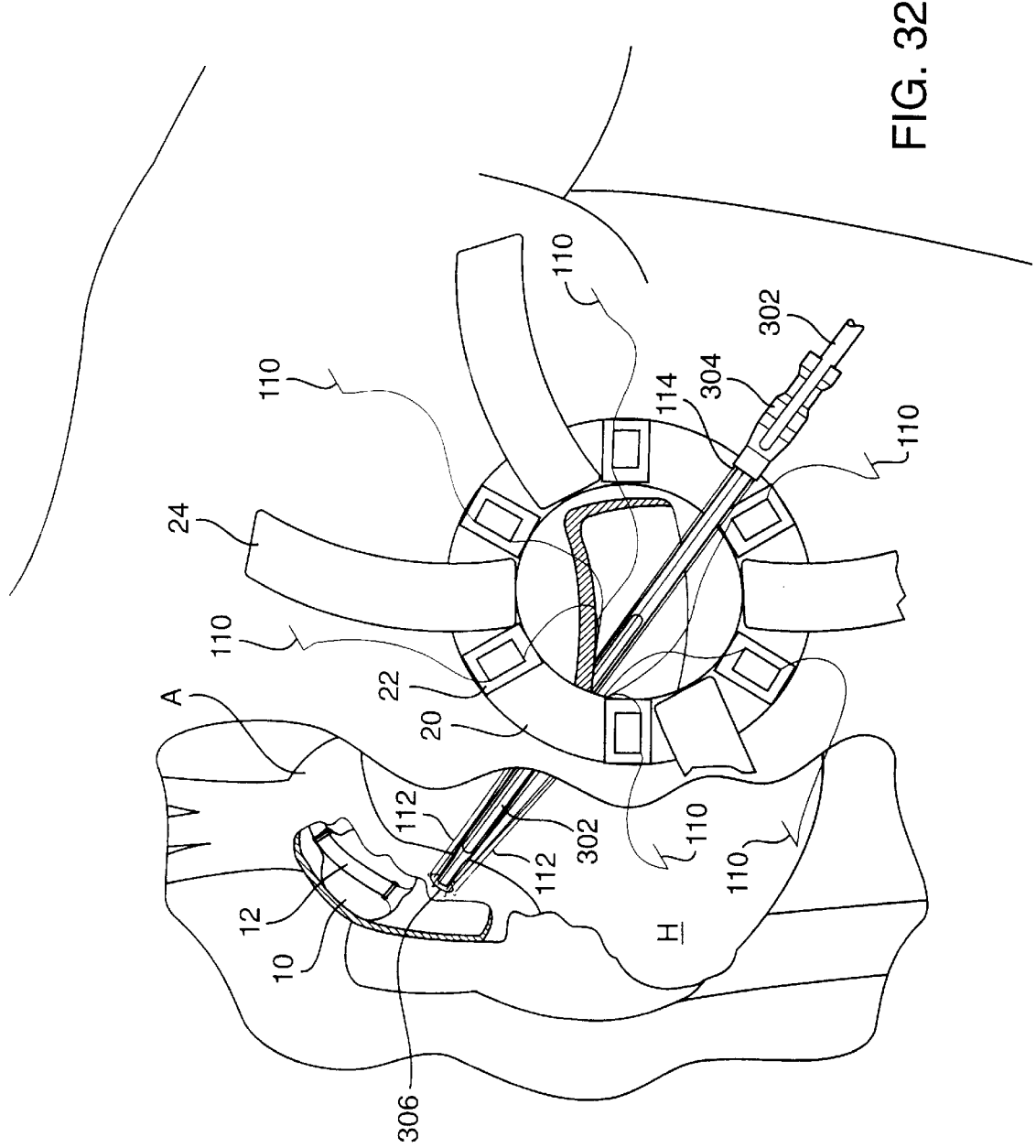
FIG. 32 is a perspective view of the delivery device shown in FIG. 31, after the vascular conduit has been moved into contact with the aorta.
Figure 33:
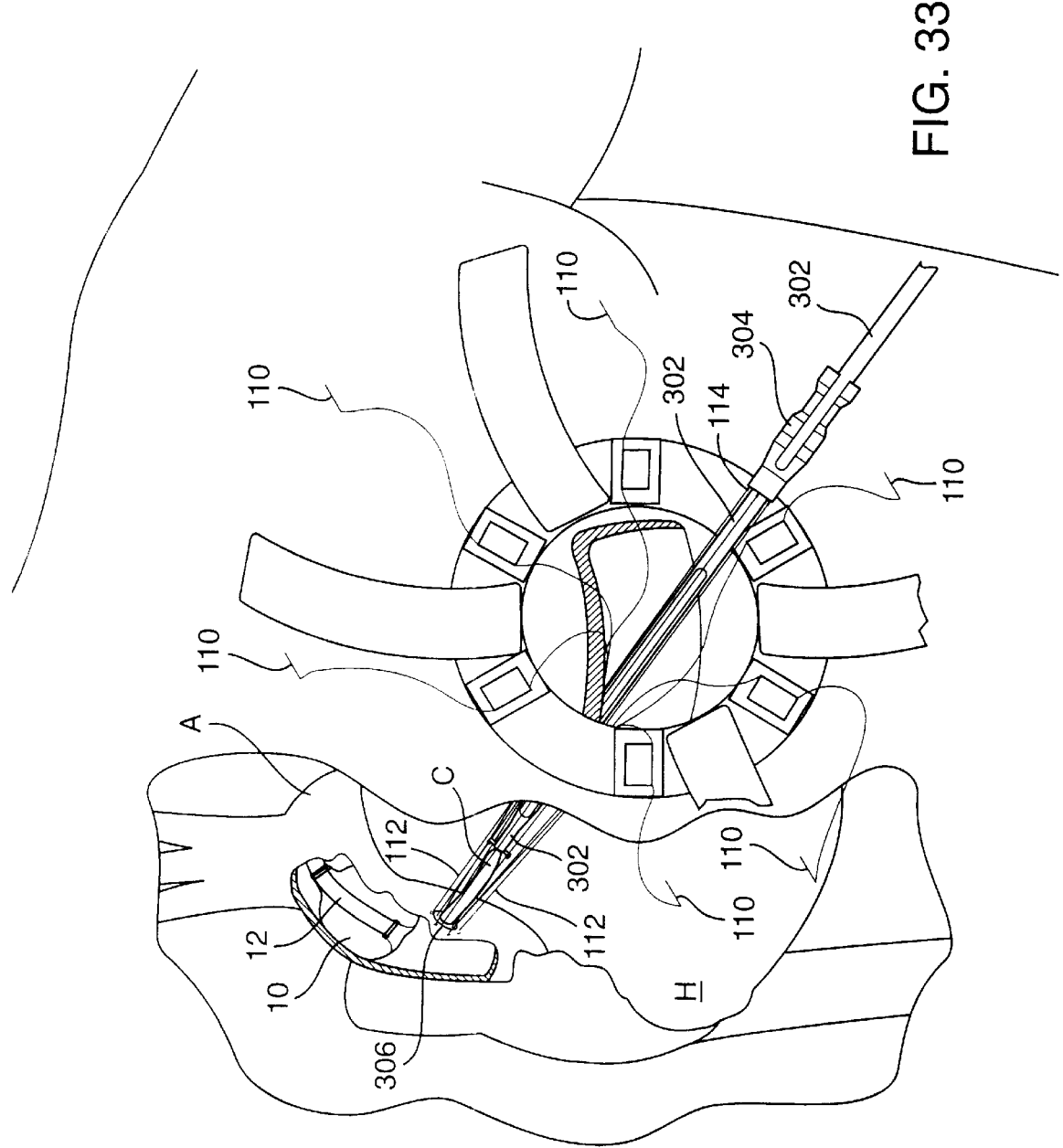
FIG. 33 is a perspective view illustrating the delivery device shown in FIG. 32 being withdrawn from the vascular conduit with the suture lengths maintaining the conduit against the aorta.

FIG. 31 shows the conduit C being moved along the suture lengths toward the aorta A, while FIG. 32 shows the delivery device 300 after the shaft 302 has been moved with respect to the collar 304 so as to place the everted end of the conduit C against the aorta in communication with the aortotomy O. Each length of suture 112 has its end carried by a needle 110 secured to the suture organizer 20, and its end carried by a needle 114 supported by the collar 304 of the delivery device 300. From the position shown in FIG. 32, the shaft is moved away from the aorta A such that the conduit C remains against the outer wall of the aorta, as illustrated in FIG. 33. While the suture lengths 112 preferably engage the end of the conduit and the sealing element 306 with sufficient friction so that upon retracting the shaft 302 the conduit and sealing element are released from the arms 310, it may be necessary to manipulate the shaft 302 to aid in releasing the conduit and sealing element.

Figure 34:
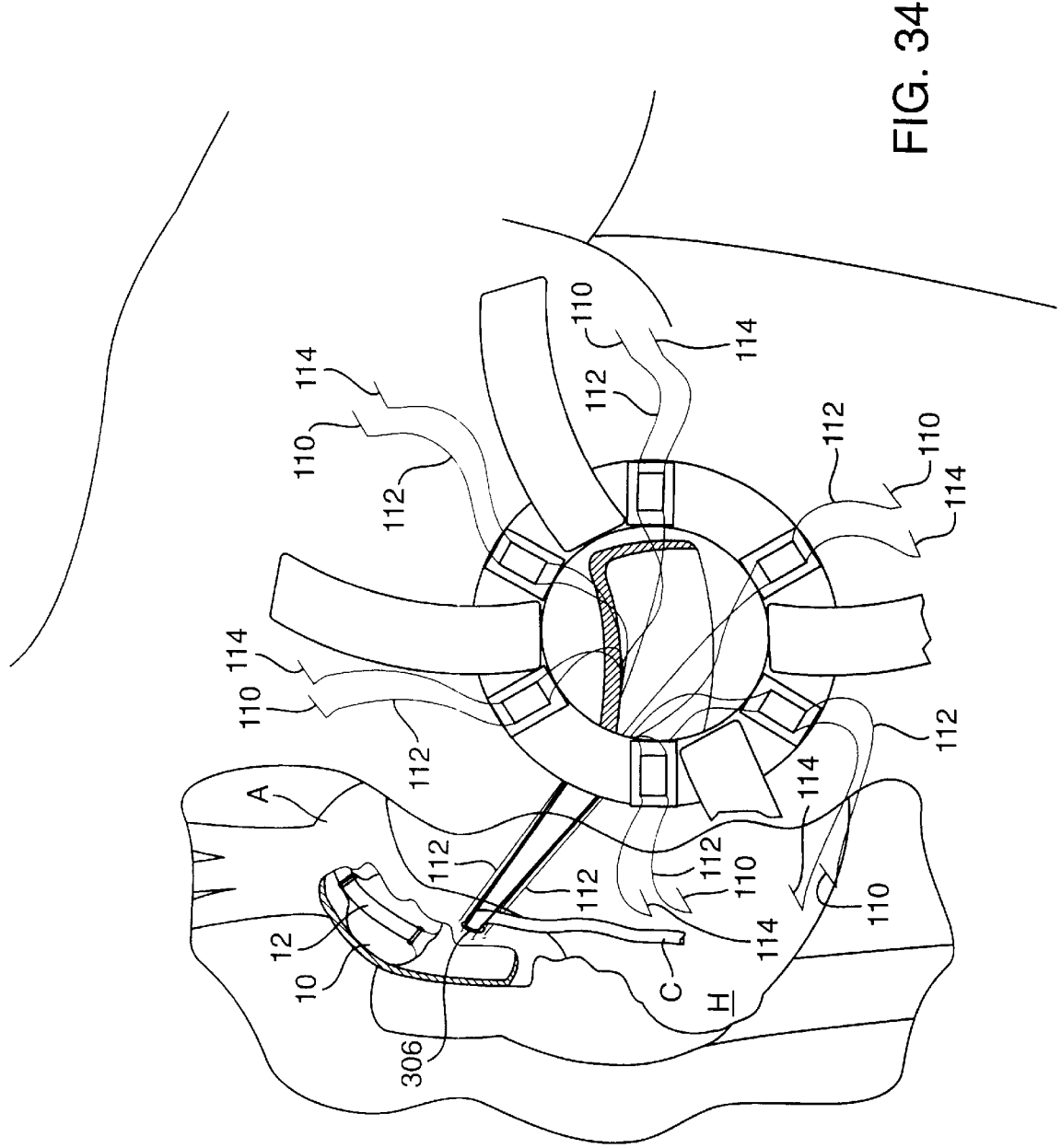
FIG. 34 is a perspective view corresponding to FIG. 33 after the delivery device has been removed from the vascular conduit, and after the lengths of suture and needles in the second set have been removed from the delivery device and secured to the suture organizer.
Figure 35A:
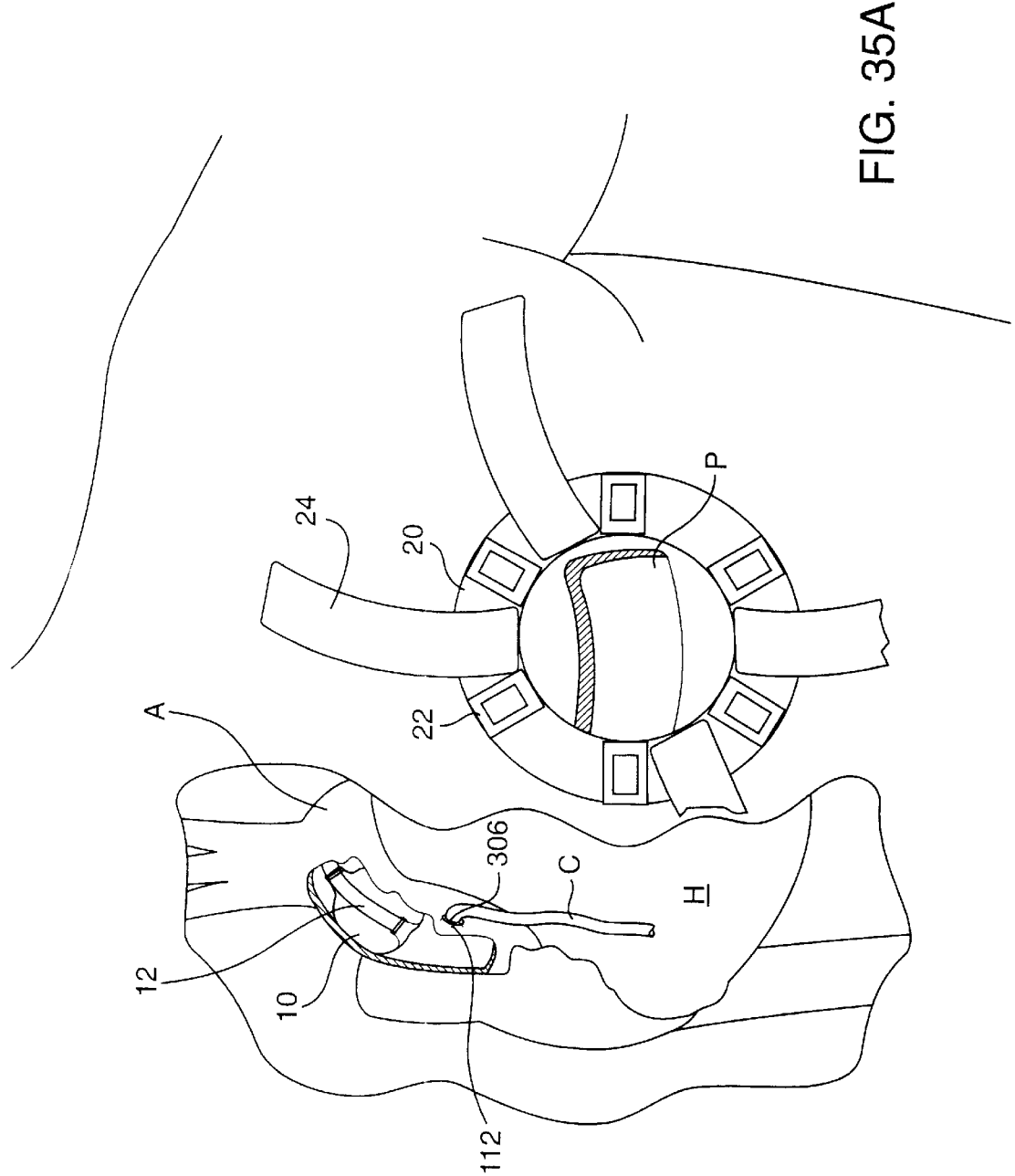
FIG. 35A is a perspective view corresponding to FIG. 34 after the opposite ends of each suture length have been secured to form an anastomosis between the vascular conduit and the aorta.
Figure 35B:
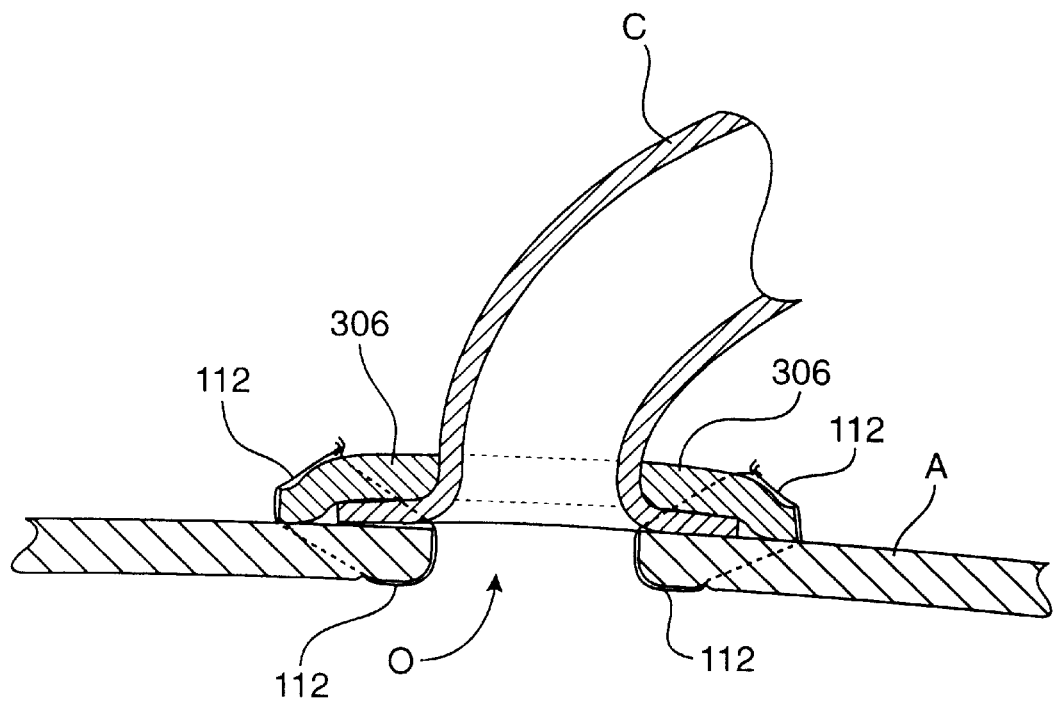
FIG. 35B is a sectional view through the anastomosis shown in FIG. 35A.
Figure 36:
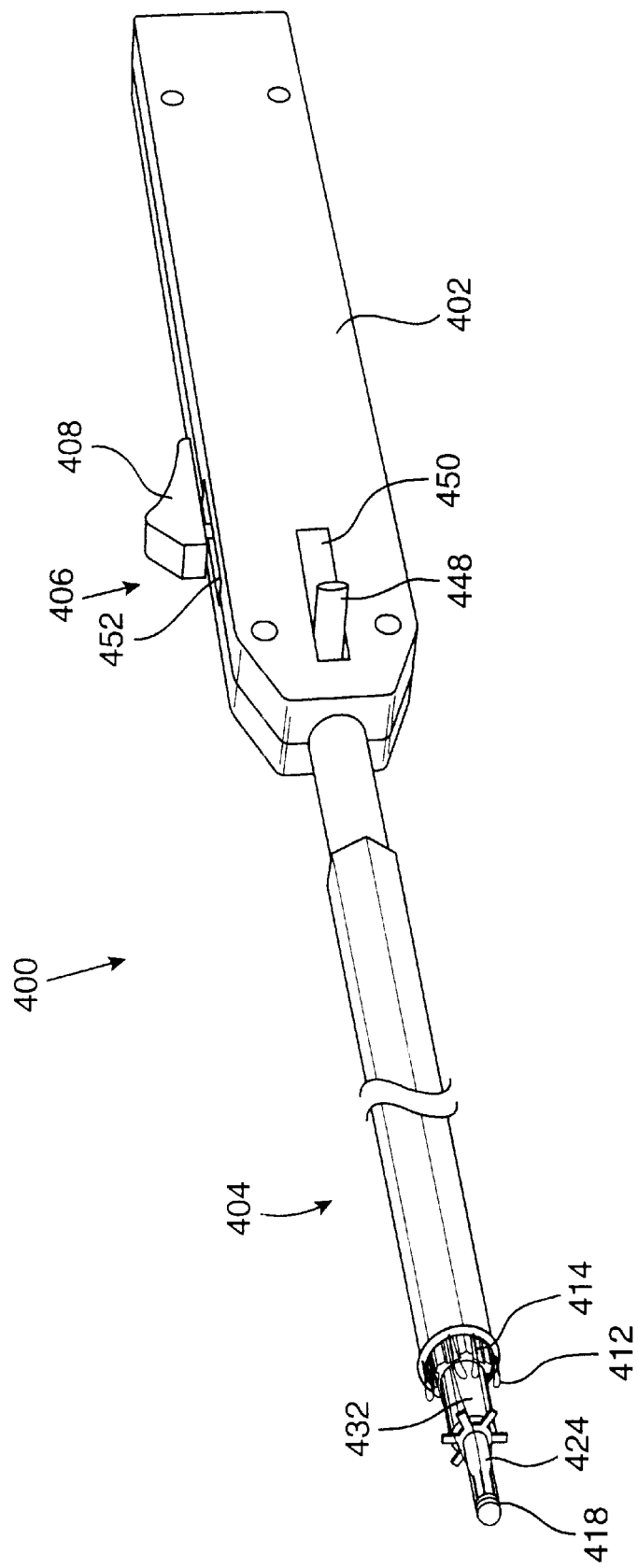
FIG. 36 is a perspective view of a needle passer constructed according to another embodiment of the invention.

After the shaft 302 has been withdrawn through the port P, the needles 114 are removed from the collar 304 and placed in the suture organizer 20. In the configuration shown in FIG. 34, the two ends of each suture length 112 are held in the same suture holding area 22, which permits the opposite ends of each suture length 112 to be knotted quickly and easily outside the patient's body. Alternatively, the lengths of suture may be knotted before the shaft 302 is withdrawn away from the patient's body. The knots are pushed down against the aorta or sealing element 306 and the free ends of the suture severed to form the anastomosis, as shown in FIGS. 35A and 35B. A suitable device for pushing the knots is disclosed in U.S. Pat. No. 5,601,576. It will be recognized that in lieu of knots, clips or other devices may be used to secure the suture. The vascular conduit C is now anastomosed to the aorta and is in fluid communication therewith.

As can be seen from FIG. 35B, the sealing element 306 is sized such that it overlies the everted end of the vascular conduit C. Of course, the size of the sealing element may be varied from that shown and depending on the application. As shown in FIG. 35B, each suture length 112 has a portion 112a which is threaded through the wall of the aorta A, and a portion 112b which extends into the aortotomy O and through the end of the conduit and the sealing element 306.

The portions 112a, 112b are secured, for example, by a knot, which results in the sealing element 306 compressing the end of the conduit against the wall of the aorta. The everted end of the conduit acts somewhat like a gasket and provides a secure and sealed anastomosis between the conduit C and the aorta A, due in part to the fact that the force applied by the suture lengths 112 is distributed around the entire periphery of the end of the conduit by the sealing element 306. This helps provide a fluid tight (or substantially fluid tight) seal which increases long term patency of the anastomosis.

The preferred sealing element 306 is formed of a biocompatible material suitable for long-term implantation in the body. Suitable materials include, for example, silicone, urethane, pebax, polypropylene (PP), polymethylmethacrylate (PMMA), and surgical felt comprising polyester or polytetrafluoroethylene (PTFE). The material may be flexible or stiff, however, a relatively resilient and compressible material is preferred. If the sealing element is formed of a relatively stiff material, such as PP or PMMA, then it may be necessary or desirable to reduce its thickness in order to provide some flexibility, as compared to a sealing element formed of a relatively soft material, such as silicone or urethane. In addition, the sealing element may be provided with radiopaque characteristics to function as a graft marker by permitting its detection, for example, by forming the element of silicone impregnated with 30% barium sulfate.

Further, the sealing element, rather than being formed of a single sheet or layer, may comprise multiple layers of either the same or different materials, e.g., a layer of bioabsorbable fabric laminated to a layer of PTFE. Persons skilled in the art will recognize that other materials may be used as well. In any case, the material forming the sealing element is preferably penetrable by a needle. Alternatively, or in addition to being formed of a material penetrable by a needle, the sealing element may be provided with openings which receive the needle(s) to allow the sealing element to be slid over the suture.

Additionally, while the illustrated sealing element is in the form of circular ring having a continuous periphery, it may instead have a noncircular shape and comprise discrete segments, for example, one segment per needle and length of suture. The segments could be separated by cuts that extend completely or partially through the material. Also, the material forming the sealing element may be provided with markings indicating an optimal location for placing the needles. It may be desirable to place the needles closer to the outer edge of the sealing element than the center in order to increase the pressure exerted against the edge of the conduit and the tissue; however, placement of the needles typically will vary depending on the application.

The size of the sealing element will vary depending on the application. For the ring-shaped element depicted in the Figures, the inside diameter (i.e., the diameter of the central opening) may be 3.5 mm and the outside diameter 7.5 mm. Other configurations may have an inside diameter of 4.5 mm and an outside diameter of 8.5 mm, or an inside diameter of 5.5 mm and an outside diameter of 9.5 mm. The thickness of the sealing element will also vary, but may be within a range of from about 0.010 to about 0.060 inch, with a preferred thickness of 0.030 inch.

Finally, while the sealing element is described and illustrated in connection with forming an anastomosis between a vascular conduit and a patient's aorta, it should be recognized that it may be used in other applications. For example, the sealing element may find use in securing a patch over an opening in tissue, such as attaching a pericardial patch over an atrial or ventricular septal defect, or repairing a patent ductus arteriosus. In this case, the sealing element may comprise a solid disc as the patch is used to close off the defect. Moreover, while the illustrated sealing element is secured to tissue by separate lengths of suture which form separate stitches, it could also be attached to tissue by a running stitch formed by a continuous length of suture.

Referring to FIGS. 36 and 37A–37D, a needle passer constructed according to an alternative embodiment of the invention is indicated by reference numeral 400 and comprises a handle 402 and a shaft assembly 404 which is operated by an actuator assembly 406. The needle passer 400 is preferably constructed so that a user can grasp and operate it using one hand. The handle 402 thus is configured to be held in one hand and the actuator assembly 406 includes a movable component, preferably in the form of a slide 408, which can be manipulated by the user's thumb or finger in order to actuate the shaft assembly 104 and pass one or more needles through tissue. The handle 402 may comprise two pieces secured together (as shown) or a single piece.

The shaft assembly 404 has essentially the same construction as the shaft assembly 104 of the needle passer 100 described above. The shaft assembly 404 supports one or more needles 410 configured to be passed through tissue, each needle 410 being secured to a first end of a length of suture 412. A second end of each suture length 412 is secured to one of a second set of needles 414 removably supported by a suture tube 432. While the second ends of the suture lengths 412 are preferably secured to the second set of needles 414, they could alternatively by secured to shaft assembly 404 (or another portion of the needle passer 400).

The needles 410 are supported on a shaft 416 via a collar 418 and an O-ring located in an annular groove defined in the collar. The O-ring engages the exterior of each needle 410 to frictionally retain it in the collar 418 so that the needles 410 can be moved between the radially non-extended position shown in FIGS. 37A and 37B to the radially extended position shown in FIGS. 37C and 37D. (The suture lengths 112 and the needles 114 are omitted from FIGS. 37A–37D.) The collar 418 preferably has slots which limit or control the extent to which the needles 410 can move radially. The shaft assembly 404 preferably has a protective cover 424 in the form of a sleeve slidably disposed over the shaft 416 and needles 410. The cover 424 has a plurality of slots 426 through which the suture lengths 412 pass from the first set of needles 410 to the second set of needles 414.

Figure 37A:
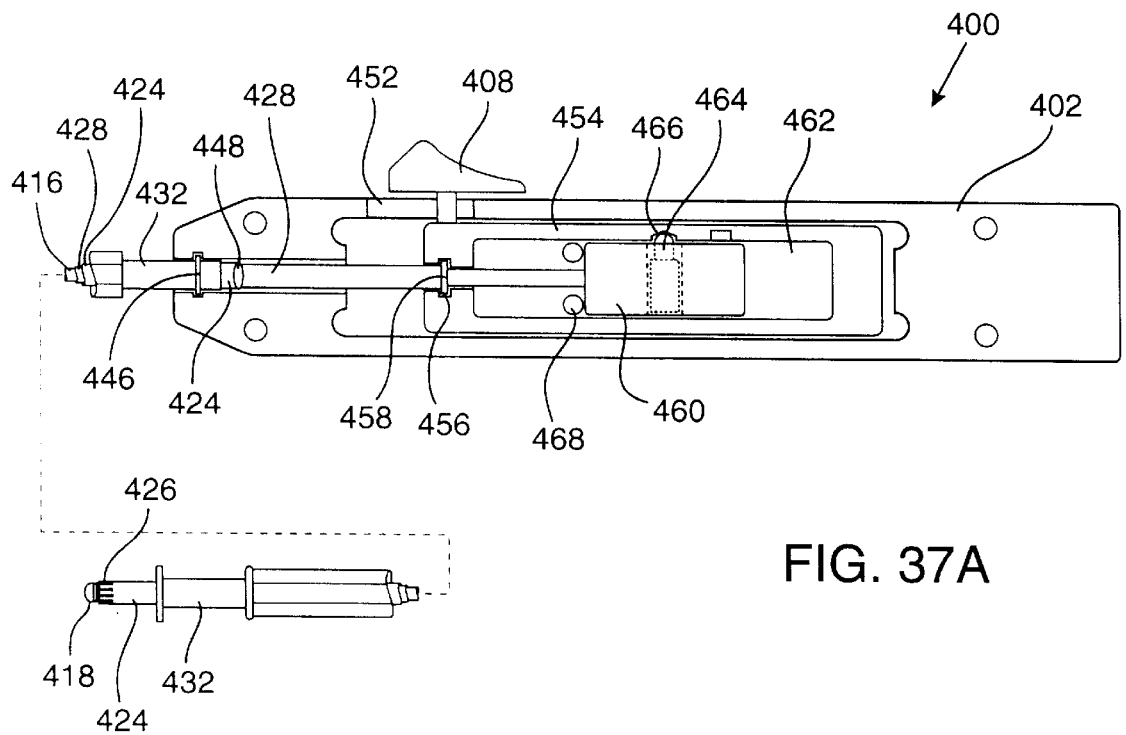
FIG. 37A is a side elevation view of the needle passer shown in FIG. 36 with part of the device broken away, the device shown prior to actuation.
Figure 37B:
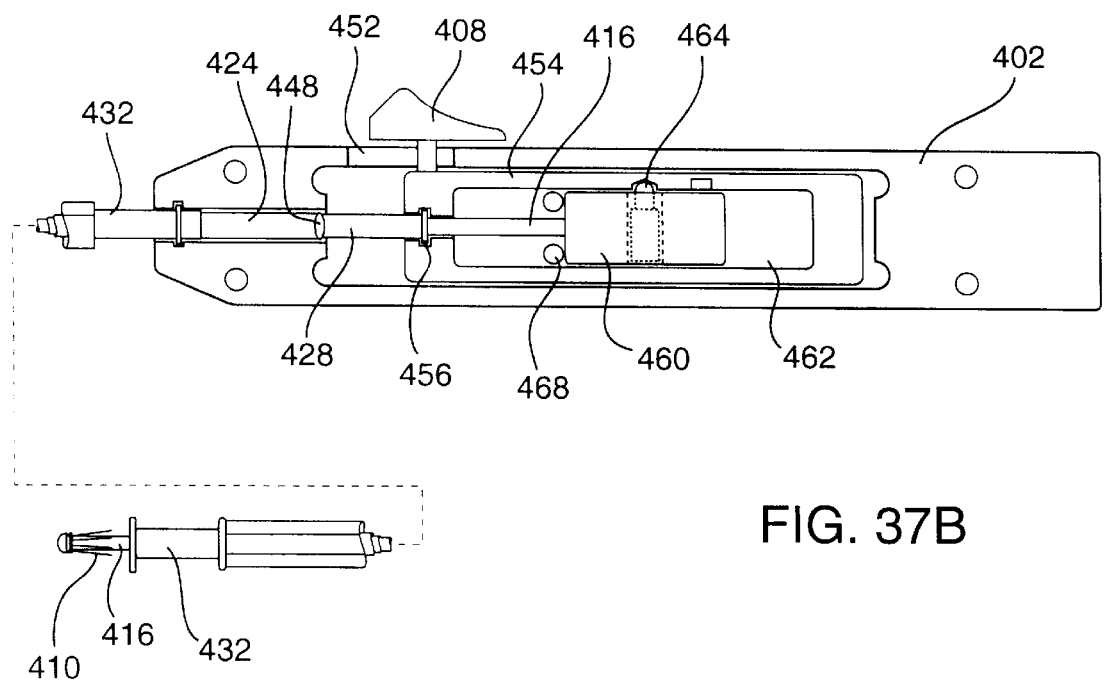
FIG. 37B is a side elevation view of the needle passer shown in FIG. 37A, with the device shown in a first stage of actuation.

The actuator 406 is used to move the cover 424 and expose the needles 410, this position of the cover being shown in FIG. 37B. Once exposed, the needles 410 are free to move into their radially extended position. In the prefelTed embodiment, the needles 410 are forced into their radially extended position by a ram sleeve 428 activated by the actuator 406. It will be recognized, however, that an alternative manner of moving the needles 410 to their radially extended position could be used, for example, any of the variations discussed above with respect to the previous embodiment.

Referring to FIG. 37A, the cover 424, ram sleeve 428 and shaft 416 are disposed in a suture tube 432 which has a flange 446 connected to the handle 402, the suture tube supporting the needles 414 and suture lengths 412. The actuator 406 is first used to uncover the needles 410. The cover 424 is moved by a lever 448 which is free to travel in a slot 450 formed in the handle 402. The lever 448 is secured to (or formed integrally with) the cover 424. The lever 448 thus is retracted with respect to the handle 402 to move the cover 424 from the position shown in FIG. 37A to the position shown in FIG. 37B, thereby exposing the needles 410. The cover 424 (or lever 448) is preferably frictionally engaged with the handle 402 so that the cover remains in its retracted position.

Next, the slide 408 of the actuator 406 is used to move the needles 410 into their radially extended position. The slide 408 travels within a slot 452 in the handle 402 and is connected to a ram driver 454 (FIG. 37C). The ram driver 454 has a groove 456 in which is fixed a flange 458 formed on the proximal end of the ram sleeve 428. A shaft driver 460 is fixed to the shaft 416 and is disposed in a chamber 462 of the ram driver 454. The shaft driver 460 contains a spring-loaded detent in the form of a ball plunger 464 engaged with a recess 466 formed in the ram driver 454. The shaft driver 460 engages a stop 468 which prevents movement of the shaft driver (and thus shaft 416 and needles 410) toward the distal end of the shaft assembly 104.

The slide 408 is moved forward from the position shown in FIG. 37B which moves ram driver 454 and ram sleeve 424 forward. The shaft driver 460, however, is prevented from moving forward by the stop 462. Moving the slide 408 forces the shaft driver detent 464 out of recess 466 to permit the ram driver 454 to move forward. The recess 466 is formed with tapered walls that permit the ball plunger 464 to be forced out of the recess. As the slide 408 continues to be moved, the ram driver 454 moves along the shaft driver 460 until the ball plunger 464 seats in a second recess 470 formed in the ram driver. At this point, shown in FIG. 37C, the ram sleeve 428 has forced the needles 410 into their radially extended position, and the relative position of the ram driver 454 and shaft driver 460 is fixed by the ball plunger 464 and recess 470. The recess 470 is preferably configured to prevent the ball plunger 464 from escaping once located therein.

Next, in order to pass the needles 410 through tissue, the slide 408 is moved rearward with respect to the handle 402. This moves the ram driver 454 and shaft driver 460 rearward to retract the shaft 416, needles 410 and ram sleeve 428, thereby passing the needles 410 through the tissue (not shown in FIGS. 37A–37D). The needles 410 may then be removed from the needle passer to thread the suture lengths 412 through the tissue, as described above with respect to the previous embodiment.

Figure 38:
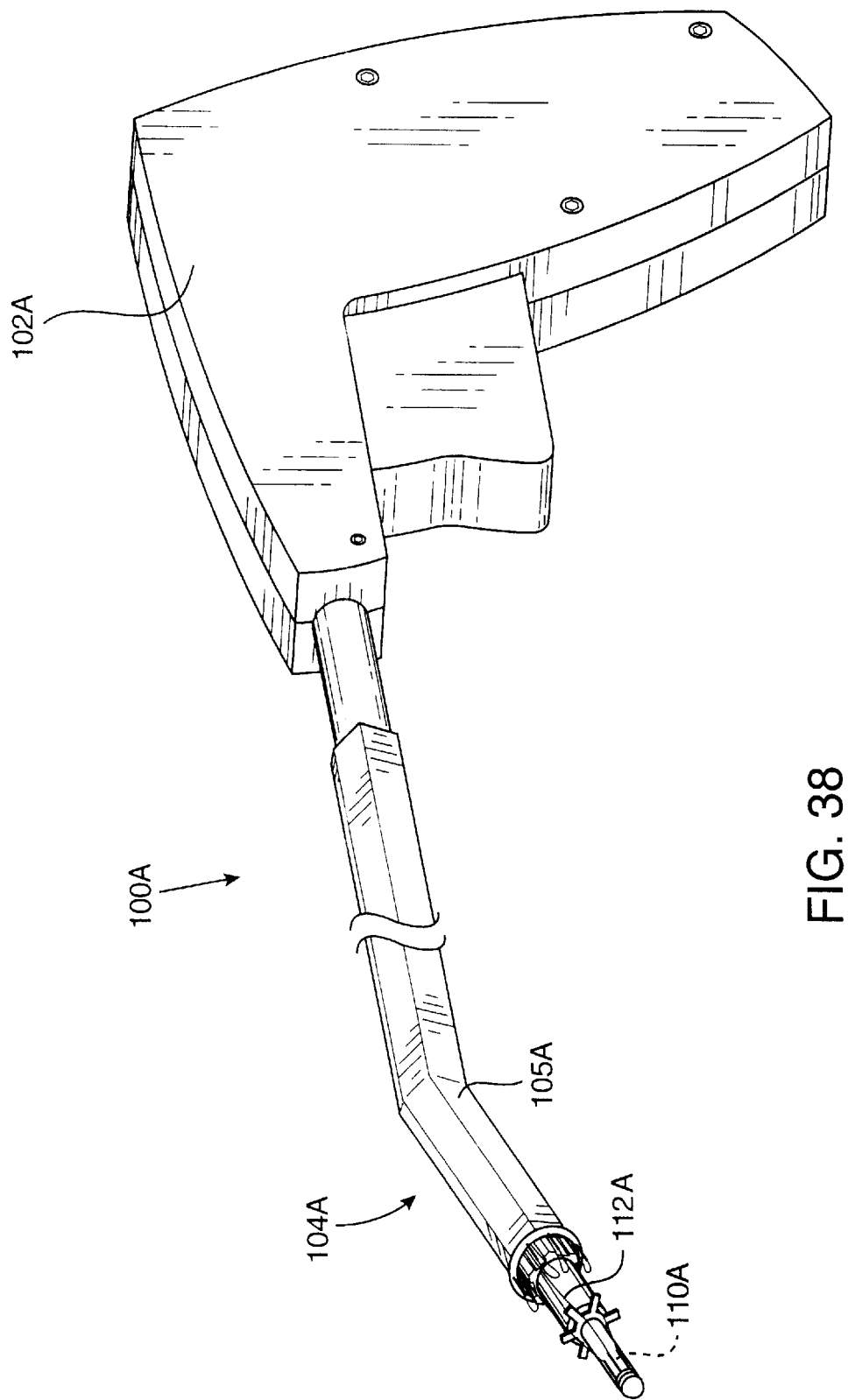
FIG. 38 is a perspective view of a needle passer constructed according to another embodiment of the invention.

While two specific embodiments of a needle passer have been described in detail, many modifications and variations of this aspect of the invention are possible. Although the shaft assemblies of the preferred and illustrated needle passers are straight over their length, they may instead be contoured. For example, as shown in FIG. 38, a needle passer 100A is constructed so as to include a shaft assembly 104A formed with a bend 105A so that the distal portion supporting the needles 110A and suture lengths 112A is offset from the proximal portion disposed adjacent the handle 102A. This may be useful in passing needles through a tissue site that is not aligned or directly accessible through the port or other opening in the patient's body. The outermost component (the suture tube in the illustrated embodiment) may be rigid and bent, while the shaft (and ram sleeve and cover, if used) are formed of a flexible material that permits axial movement of the shaft over the bend. The shaft entire shaft may be flexible, or only the portion that carries the needles may be flexible. Similarly, the entire ram sleeve and cover may be flexible, or only the portions thereof that move and cover the needles may be flexible.

In another alternative embodiment, the components of the shaft assembly are formed of a malleable or ductile material, thereby permitting the surgeon to shape the device into various configurations by moving the distal portion with respect to the proximal portion. Similarly, the shaft assembly could have an articulated construction that would permit the surgeon to adjust the position of the distal portion with respect to the proximal portion. Each of these embodiments would be useful in passing the needles through tissue located at areas that are not aligned with the port or other access opening in the patient.

Figure 39A:
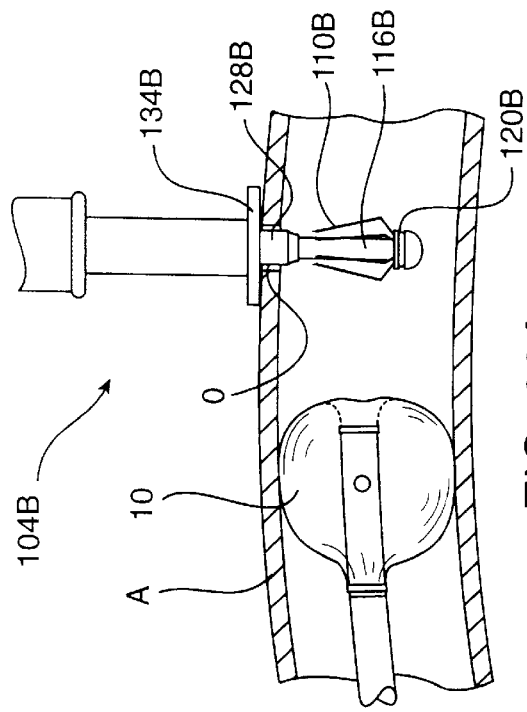
FIGS. 39A–39C are side elevation views, partly in section, of a portion of the shaft assembly of a needle passer constructed according to another embodiment of the invention, wherein the needle passer is being used to pass a first set of needles through the wall of an aorta.
Figure 39B:
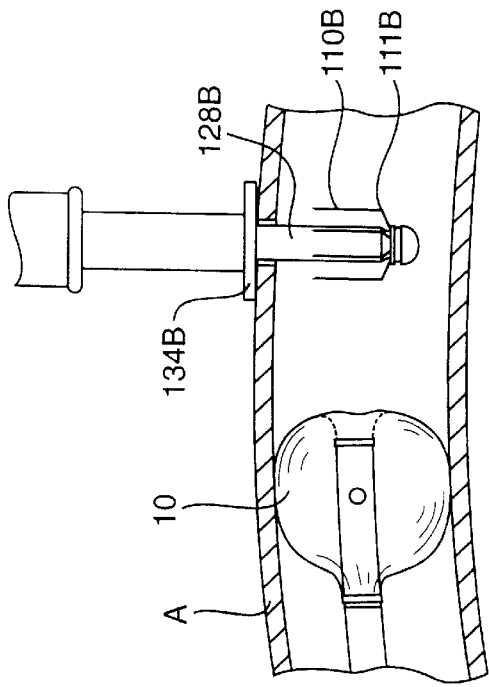
Figure 39C:
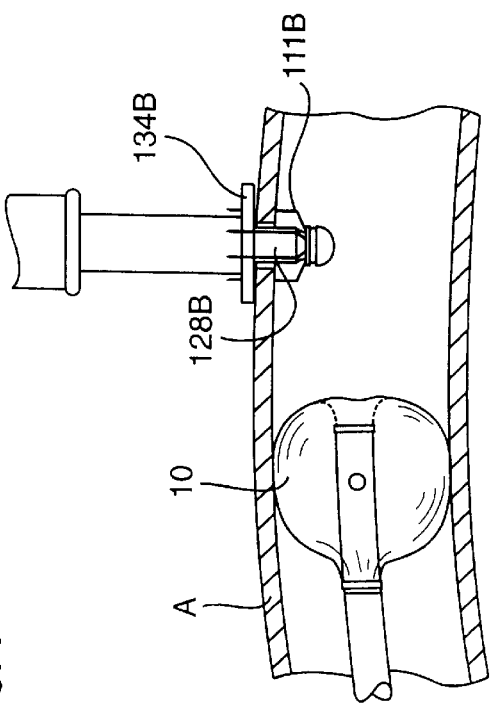

FIGS. 39A–39C show a shaft assembly 104B forming part of a needle passer constructed according to another variation of the invention. The distal end of the shaft assembly 104B is placed within the aorta A through the aortotomy O, the foot 134B resting on the outer surface of the aorta as shown in FIG. 39A. In order to ensure that the needle passer does not contact the balloon 10, the position of the balloon within the aorta A is preferably monitored or controlled as described above with respect to the previous embodiments. Next, the surgeon actuates the actuator assembly (not shown) to move the ram sleeve 128B to move the needles 110B to their radially extended position, shown in FIG. 39B. Although the embodiment of FIGS. 39A–39C does not include a cover which overlies the needles 110B, it should be recognized that a cover may be included if desired.

Further actuation of the actuator assembly moves the shaft 116A, needles 110A and ram sleeve 128B toward the handle (not shown) of the needle passer, which passes the radially extended needles 110B through the wall of the aorta A, as shown in FIG. 39C. The needles 110B pass through the aorta and between the fingers of the foot 134B, with the lengths of suture extending from the second set of needles and through the aortotomy O to needles 10A held in the collar by O-ring 120B. (The second set of needles and lengths of suture are omitted from FIGS. 39A–39C for explanatory purposes.) As can be seen from FIGS. 39A–39C, the needles 110B, rather than being straight over their length, are formed with a bend 111B which results in the axis of each needle being generally perpendicular to the aorta when in the radially extended position (FIG. 39B). This feature allows the needles 110B to be passed through the tissue with minimal force, as compared to passing the needles through the tissue at an angle as in the above embodiments. It will be understood that alternative needle configurations may be used if desired.

Figure 40B:
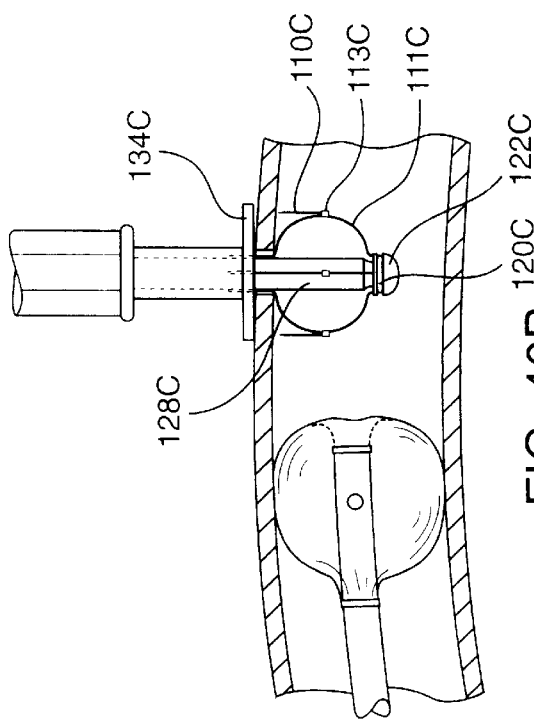
FIGS. 40A–40C are side elevation views, partly in section, of a portion of the shaft assembly of a needle passer constructed according to still another embodiment of the invention, wherein the needle passer is being used to pass a first set of needles through the wall of an aorta.
Figure 40C:
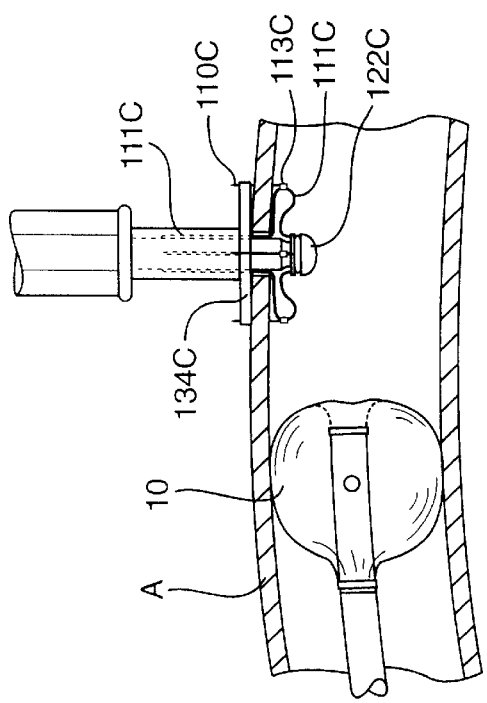
Figure 40A:
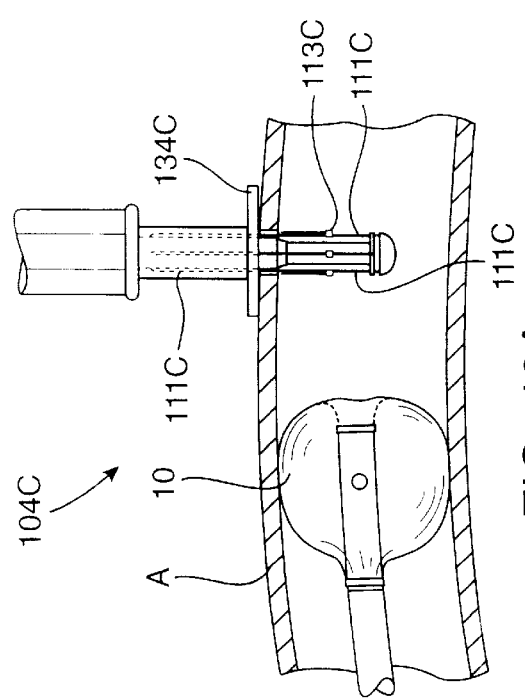

FIGS. 40A–40C show a shaft assembly 104C forning part of a needle passer constructed according to yet another variation of the invention. As above, the distal end of the shaft assembly 104C is placed within the aorta A through the aortotomy O with the foot 134C resting on the outer surface of the aorta, as shown in FIG. 40A. In order to ensure that the needle passer does not contact the balloon 10, the position of the balloon within the aorta A is preferably monitored or controlled as described above with respect to the previous embodiments. The shaft assembly 104C comprises a plurality of flexible struts 111C each of which is provided with a member, such as a tubular piece 113C, which supports a needle 110C. The struts 111C and thus the needles 110C are preferably positioned around the axis of the shaft assembly 104C in a spaced manner.

Each strut 111C has one end fixed to the collar adjacent the distal end 122C and an opposite end fixed to the ram sleeve 128C. While the embodiment shown in FIGS. 40A–40C does not include a cover which overlies the needles 110C, a cover may be included if desired. When the ram sleeve 128C is in its retracted position, as shown in FIG. 40A, the struts 111C are generally straight with the needles 110C disposed along the shaft assembly 104C. As the ram sleeve 128C is moved forward, the ends of each strut 111C are brought toward each other, which results in the struts flexing outward to the position shown in FIG. 40B. This moves the needles 110C to a radially extended position in which they are ready to be passed through the tissue. The struts 111C may be formed of a superelastic material, such as nitinol, although other resilient and flexible metals or polymers may be used.

Further actuation of the actuator assembly (not shown in FIGS. 40A–40C) moves the shaft, needles 110C and ram sleeve 128C toward the handle of the needle passer, which passes the radially extended needles 110C through the wall of the aorta A, as shown in FIG. 40C. The needles 110C pass through the aorta and between the fingers of the foot 134C, with the lengths of suture extending from the second set of needles and through the aortotomy O to needles 110C held in the collar by O-ring 120C. (The second set of needles and lengths of suture are omitted from FIGS. 40A–40C for explanatory purposes.) As can be seen from FIGS. 40B and 40C, the axis of each needle is generally perpendicular to the aorta when in the radially extended position. As explained above with respect to the embodiment of FIGS. 39A–39C, this allows the needles 110C to be passed through the tissue with minimal force, as compared to passing the needles through the tissue at angle.

In the illustrated and preferred embodiments the ram is moved forward and simultaneously forces all of the needles into their radially extended position. In some applications, it may be desirable to move the needles individually into the radially extended position. In order to accomplish this, the needle passer, for example, could include a ram with individual segments or portions corresponding to a respective needle. The actuator assembly would permit the surgeon to actuate the ram to move a specific needle into its radially extended position. Such a construction could be used in applications where the suture must be passed through a number of spaced tissue locations. The surgeon could position the needle passer at one site and actuate the ram to pass one needle through the tissue, and then move the needle passer to a different site and actuate the ram again to pass a different needle through the tissue. In this manner, the suture could be passed through tissue in a larger tissue pattern than if the needles are moved through the tissue simultaneously.

Additional modifications of the illustrated embodiments of the needle passer include utilizing the needle passer to form the opening in the hollow body structure, such as an aortotomy in the patient's aorta. This could be accomplished by providing a cutting element, such as trocar point, on the distal end of the needle passer. For example, the collar which carries the needles could include a trocar point or be formed with an aortic punch-like cutting member which forms the opening in the aorta through which the distal end of the needle passer is inserted. Further, a cutting mechanism could be coupled to the needle passer for cutting through the patient's chest wall and/or the aorta. It will be appreciated that modifications such as these are within the spirit and scope of the invention.

Another possible variation of the invention would be to provide a tubular component capable of extending through the patient's chest wall and functioning as a port or trocar sleeve by permitting instruments to be inserted therethrough. For example, the suture tube carried on the exterior of the needle passer could be constructed to serve as such a port by being removed from the shaft assembly of the needle passer after the needles and lengths of suture have been passed through the aorta. Alternatively, a separate tubular element could be carried by the shaft assembly over the suture tube and removed therefrom and left in place in the opening in the patient's chest wall to act as a port or trocar sleeve.

Further still, it may be desirable to couple an endoscope with the needle passer in order to enhance visualization of the anastomosis site. The endoscope could comprise a camera and fiber optic cables extending through the interior of the needle passer, for example, by extending through a hollow shaft which carries the needles, or by extending alongside the shaft or another component of the shaft assembly. The endoscope could either be incorporated into the needle passer or a separate device used with the needle passer.

Persons skilled in the art will recognize that performing an anastomosis is only one possible application of the devices and methods of the invention. Many other uses for the various aspects of the invention will be apparent to those skilled in the art. For example, the needle passer of the invention may be used to close an opening created in the wall of a blood vessel to carry out a catheter procedure, or to close an opening in the wall of a body cavity, such as a trocar opening in the abdominal wall. After passing the needles through the tissue, the sutures could be tied off or, alternatively, secured with clips or other fasteners in order to close the opening.

For these applications it may be desirable to use needles connected by a continuous length of suture the ends of which are tensioned and tied off (or secured with a clip) to close the opening. However, when using the needle passer in an anastomosis procedure, it is more desirable to use needles carrying separate lengths of suture so that the suture does not extend across the opening, and thus is less likely to adversely affect flow through the anastomosis site. It should nevertheless be appreciated that it is possible to use needles connected by a continuous length of suture to perform an anastomosis procedure, provided that the needles are passed through the tissue at locations which do not result in the suture extending significantly into or across the anastomosis opening.

Further, while in the preferred embodiment of an anastomosis procedure each suture length passes through the aortotomy and then through the tissue, alternative configurations may be used. For example, several pairs of needles may be provided, the needles in each pair being connected by a length of suture. The needles in each pair may be passed through the tissue at locations radially spaced from the periphery of the opening in the tissue. The suture lengths would then each pass under the tissue radially outward of the opening and then through the tissue; as such, the suture would not pass through the aortotomy. Similarly, the needles in a given pair could be passed through the tissue at areas located on opposite sides of the opening, the result being that the suture length extends across the opening.

Another possible application for the invention is placing sutures adjacent an opening in a vessel wall or body cavity wall and delivering a patch or similar element along the suture to close the opening. For example, the needle passer can be positioned through an atrial or ventricular septal defect in a patient's heart and used to pass needles and sutures through the tissue around the defect. The sutures may then be passed through a patch and the patch guided down to the tissue so as to overlie the defect, for example by using the delivery device of the invention. The sutures may then be tied off or secured with clips to secure the patch over the defect. In this case, it may be desirable to use needles carrying separate lengths of suture.

Alternatively, rather than using a patch, the sutures extending from the tissue could simply be tied off or otherwise secured to close the tissue around the defect. In the latter case, as in the case of closing an opening in a vessel or the wall of a body cavity, needles connected by a continuous length of suture may be used if desired. Other procedures for closing atrial and ventricular septal defects using patches and suture are disclosed in co-pending application Ser. No. 08/425,179, filed Apr. 20, 1995 and entitled METHOD AND APPARATUS FOR THORACOSCOPIC INTRACARDIAC PROCEDURES, the subject matter of which is incorporated by reference.

Further, the invention can be used in valve surgery by placing the needle passer in the annulus of a heart valve and passing needles therethrough. The needles may then be picked up to thread the suture through the annulus and carried to a suture organizer disposed outside the patient's body. The needles located at the other ends of the sutures can then be passed through a replacement valve supported on the delivery device and the valve moved along the sutures to the annulus and then secured thereto. Other devices and procedures for securing a replacement heart valve are disclosed in co-pending application Ser. No. 08/594,869, filed Jan. 31, 1996 and entitled ENDOSCOPIC SUTURING DEVICES AND METHODS, the subject matter of which is incorporated by reference.

According to another aspect of the invention, a device is provided for measuring the internal size of a tubular member and may be used, for example, to measure the inner diameter of a vascular conduit prior to anastomosing the conduit to the patient's aorta, as described above. Once the size of the conduit is determined, an appropriately sized sealing element can be selected to obtain the most secure and fluid tight anastomosis.

Figure 41:
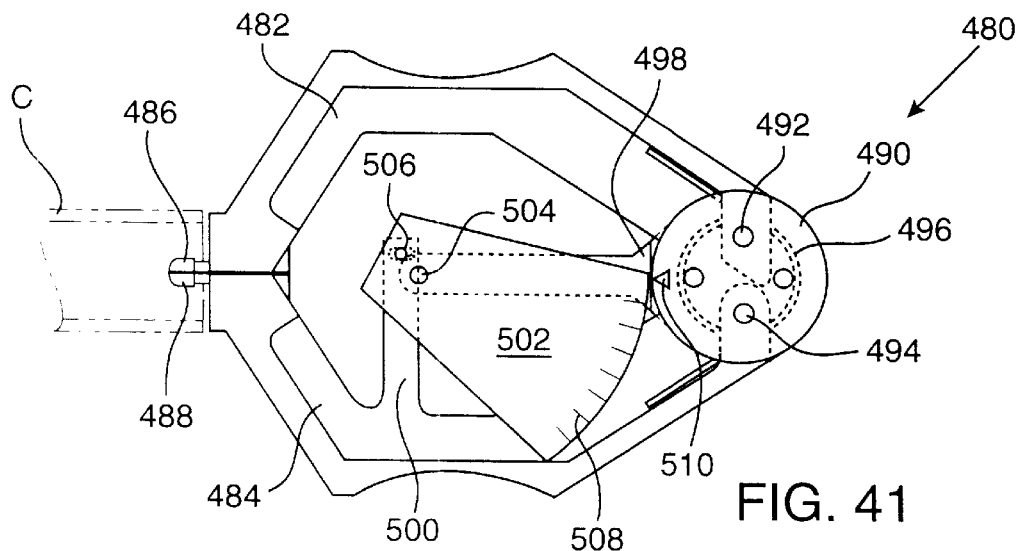
FIG. 41 is a side elevation view of a device constructed to one embodiment of the invention for measuring the inner diameter of a tubular member, such as a vascular conduit.
Figure 42:
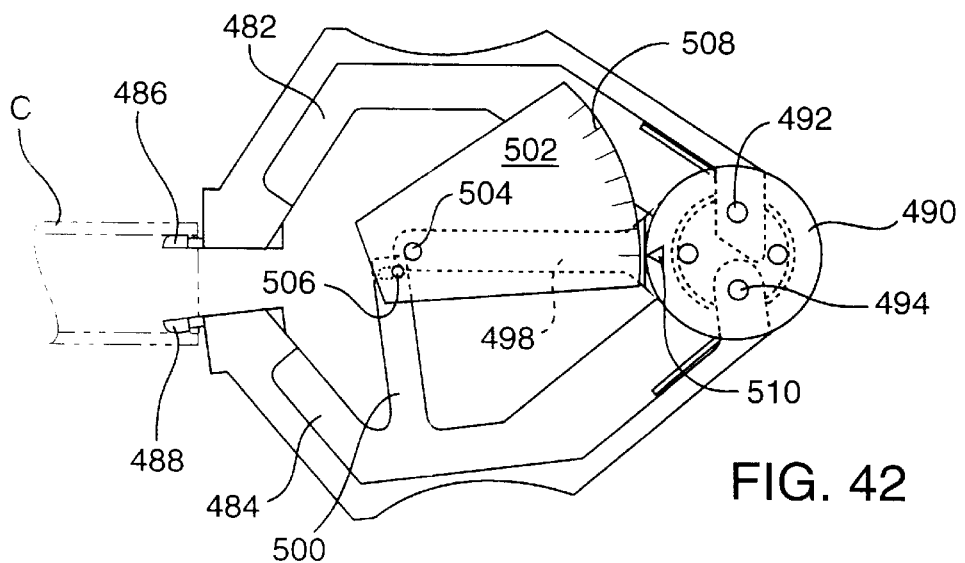
FIG. 42 is a side elevation view of the device shown in FIG. 41, wherein the device is in a measuring position.
Figure 43:
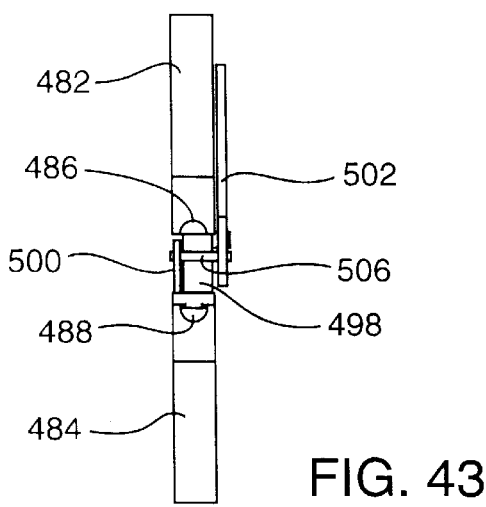
FIG. 43 is an end elevation view of the device shown in FIG. 41.
Figure 44:
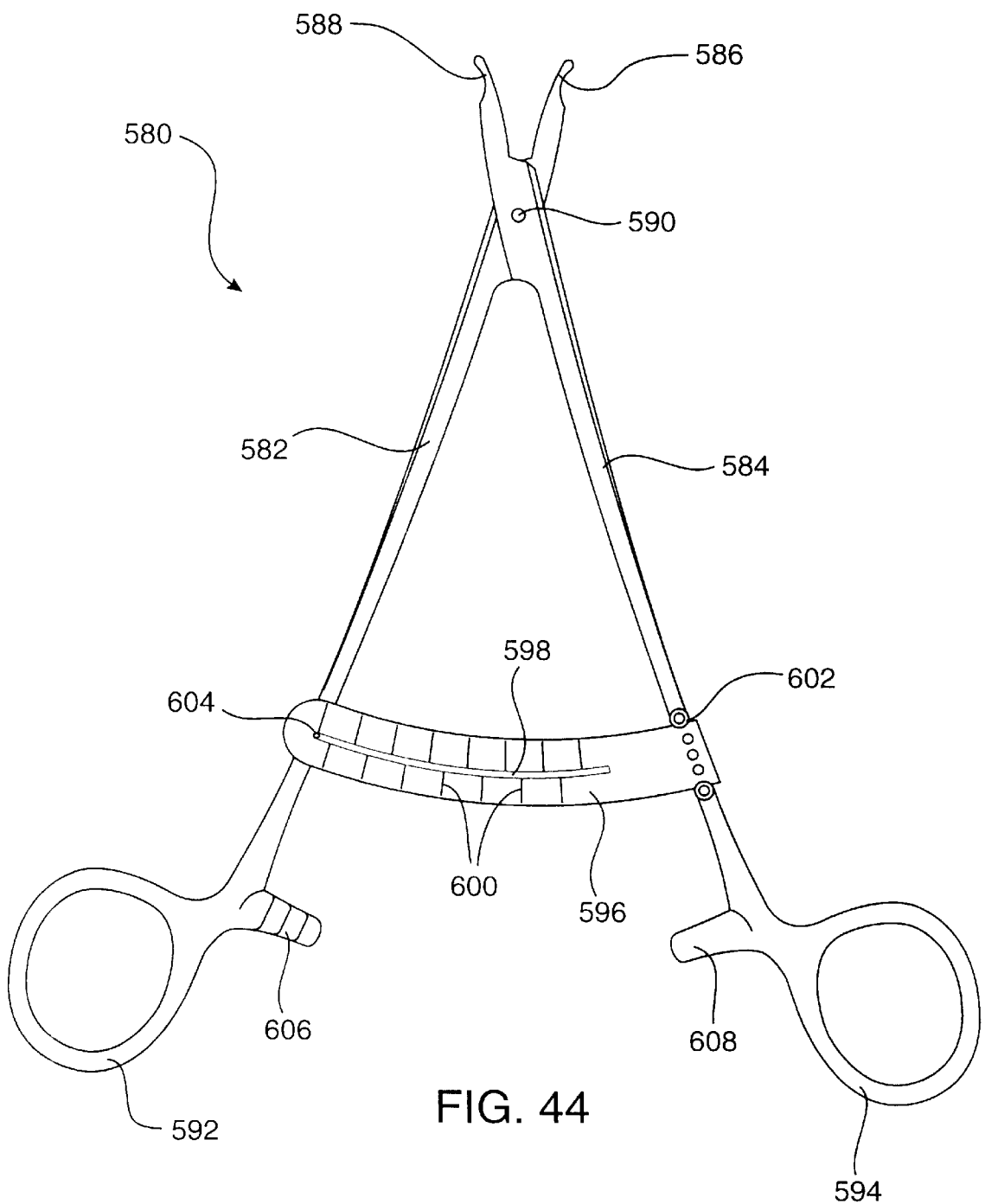
FIG. 44 is a side elevation view of a device constructed according to another embodiment of the invention for measuring the inner diameter of a tubular member, such as a vascular conduit.

A preferred embodiment of such a device is indicated by reference numeral 480 in FIGS. 41–43 and comprises a pair of jaws 482, 484 respectively provided with tips 486, 488 for contacting the opposite inner surfaces of a tubular member, such as the conduit C (shown in phantom). The jaws 482, 484 are relatively movable and are biased apart so that upon insertion into the conduit C, the tips 486, 488 move apart to contact the inner surfaces of the conduit. In the preferred embodiment, the jaw 482 is fixed to a spring housing 490 by a pin 492, while the jaw 484 is pivotally coupled to the spring housing 490 by a pivot pin 494. A coil spring 496 is disposed in the housing 490 has legs that bias the jaws 482, 484 in opposite directions.

A first arm 498 extends from the spring housing 490 and a second arm 500 extends from the jaw 484. The spring housing 490 is fixed to the jaw 482; thus, when the jaws 482, 484 move apart the arms 498, 500 move apart. A scale 502 is pivotally coupled to the first arm 498 by a pin 504, and is pivotally coupled to the second aim 500 by a pin 506. The pin 506 is located in a slot in the second arm 500 so that it is free to rotate and move laterally. As the jaws 482, 484 move apart (or together) the pins 504, 506 rotate the scale 502. The scale 502 has a series of markings 508 and the spring housing 490 has an indicator 510 located adjacent the markings. Each marking 508, when aligned with the indicator 510, corresponds to a given distance measured between the tips 486, 488.

In use, the jaws 482, 484 are brought together and the tips 486, 488 are positioned inside the conduit C (FIG. 38). The jaws 482, 484 are then released and the tips 486, 488 move into contact with the opposite sides of the interior of the lumen (FIG. 39). The indicator 510 aligns with one of the markings 508 to provide a measurement of the lumen size for the conduit, which measurement may be used, for example, to select a particular size sealing element in anastomosing the conduit C to the aorta or other vessel.

Another embodiment of a device for measuring the internal size of a tubular member is shown in FIG. 46 and is indicated by reference numeral 580. The device 580 comprises a pair of arms 582, 584 respectively provided with tips 586, 588 for contacting the opposite inner surfaces of a tubular member, such as a vascular conduit (not shown). The arms 582, 584 are relatively movable so that upon insertion into the conduit the tips 586, 588 may be moved apart to contact the inner surface of the conduit. In the illustrated embodiment, the arms 582, 584 are pivotally connected at 590, although other attachments may be used. The arms 582, 584 are preferably biased apart by a spring (not shown) extending between the arms. The arms 582, 584 are provided, respectively, at their ends opposite the tips 586, 588 with grasping portions, such as finger loops 592, 594. The loops 592, 594 are squeezed to close the tips 586, 588 for insertion into a conduit; the loops are then released to allow the tips to move away from each other and into engagement with the inner surface of the conduit.

A scale 596 is carried by one of the arms 582, 584 and comprises a slot 598 and a series of markings 600. In the illustrated embodiment, the scale 596 is fixed to the arm 584 at connection 602. A pin 604 is fixed to the arm 582 and is engaged with the slot 598 so that upon the tips 586, 588 moving into engagement with the conduit, the pin 604 moves within the slot 598. The pin 604 becomes aligned with one of the markings 600 to indicate the size of the internal diameter of the conduit (or width if the conduit is not circular). If desired, the arms 582, 584 may be provided with a mechanism for locking the tips 586, 588 in position, e.g., mating ratchet members 606, 608.

According to still another aspect of the invention, a device and method are provided for carrying out a procedure in a hollow body structure while fluid is flowing through the structure. This aspect of the invention may be used to substantially isolate a portion of the body structure, e.g., a patient's aorta, from fluid flowing therein. Referring to FIGS. 45 and 46A–46C, the device is indicated by reference numeral 610 and comprises an elongate member 612 which may be in the form of a rod or guidewire, and a tissue contacting member 614 which may be in the form of a sheet configured to engage the tissue. The member 612, which may be flexible or rigid, has a proximal end 616 and a distal end 618 secured to the member 614. The tissue contacting member 614 is preferably flexible so as to be collapsible for insertion and removal through an opening in the tissue. Although the illustrated member 614 is generally circular, other configurations may be used. The member 612 is preferably flexible; however, it may instead be rigid. For example, the member 612 may take the form of a conventional guidewire.

Figure 45:
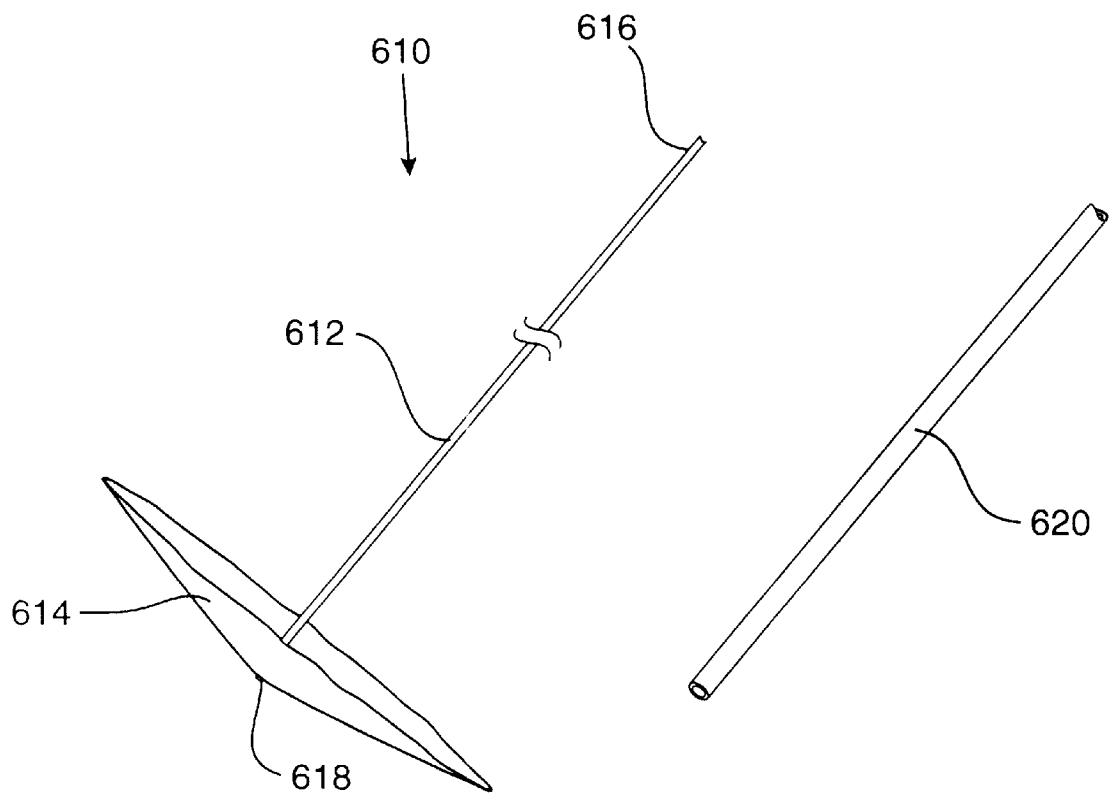
FIG. 45 is a perspective view of a device constructed according to the invention for occluding an opening in an aorta to permit a surgical procedure to be carried out therein while blood flows through the aorta.
Figure 46B:
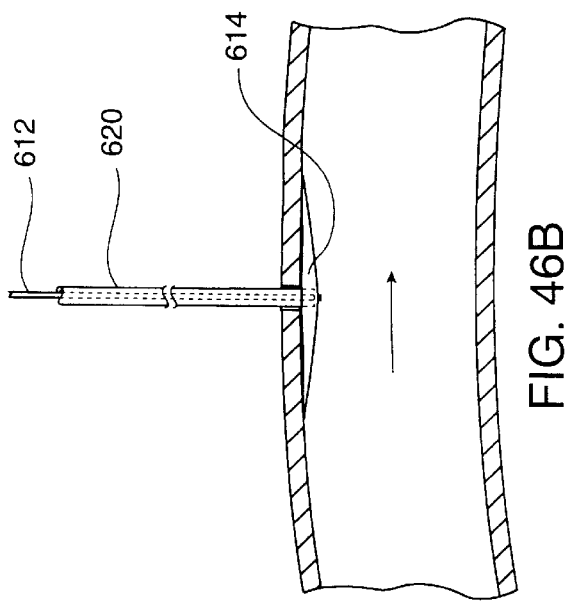
FIGS. 46A–46C are side elevation views, partly in section, of the device shown in FIG. 45 being positioned through an opening in an aorta.

The tissue contacting member 614 is collapsed from the position shown in FIG. 45 for insertion through an opening in the tissue of the hollow body structure. In order to aid in inserting the member 614 through the opening, which may be a slit or cut formed in the wall of the tissue structure, an introducer is preferably provided in the form of a hollow shaft 620. The tissue contacting member 614 is collapsed and placed in the bore of the shaft 620, as shown in FIG. 46A. The two components are then passed through the opening which, in the illustrated embodiment, is a passage P in the wall of an aorta A through which blood flows (as indicated by the arrow). Once positioned in the passage P, the member 612 is moved toward the aorta A until the tissue contacting member 614 emerges from the end of the shaft 620. The member 612 is then pulled away from the aorta A to expand the tissue contacting member 614 into engagement with the interior of the wall of the aorta, as shown in FIG. 46B. The member 614 prevents (or minimizes the amount of) blood which may escape through the passage P. Next, the introducer shaft 620 is removed from the member 612, leaving the tissue contacting member 614 against the wall of the aorta and the member 612 extending through the passage P, as shown in FIG. 46C.

Figure 46C:
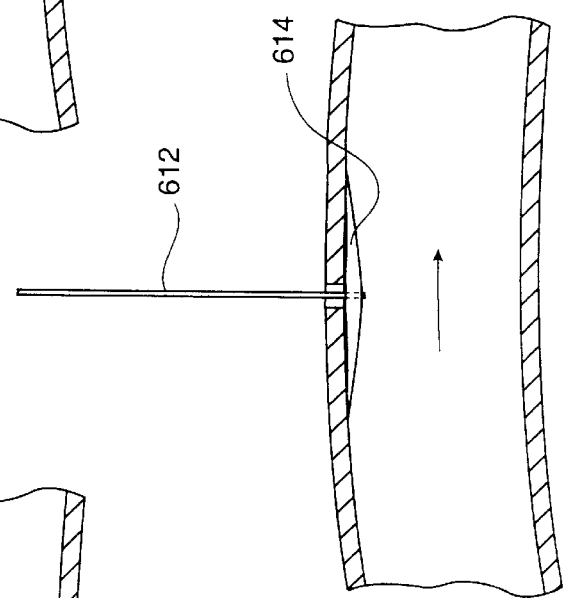
Figure 46A:
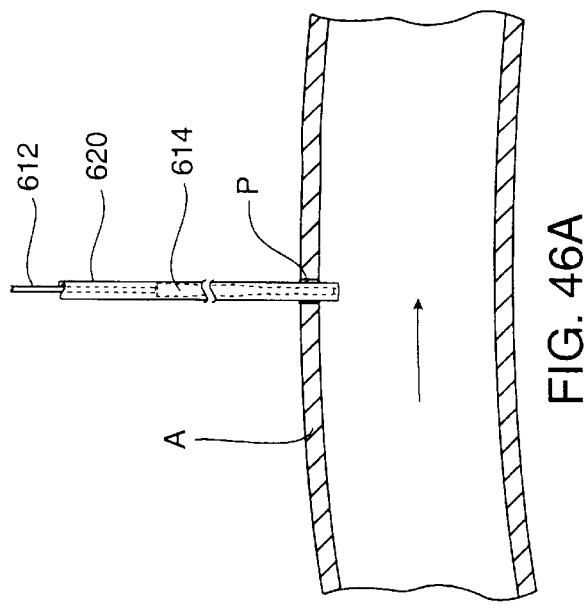

With the device 610 positioned as shown in FIG. 46C, various procedures may be performed without blood leaking through the passage P. For example, the anastomosis procedure described above with respect to the previous embodiments may be carried out by slightly modifying the needle passer and delivery device. To accomplish this, the aortic punch (not shown) may be formed with a bore that allows the punch to be slid over the member 612 and through the passage P, after which the punch is actuated to form an aortotomy. The tissue contacting member 614 prevents blood from leaking through the passage P or the aortotomy. Next, the shaft of the needle passer (not shown) may be formed with a bore that allows it to be slid along the member 612 and through the aortotomy, the tissue contacting member 614 preventing blood leakage. The distal end of the needle passer shaft assembly passes through the aortotomy and into contact with the member 614; however, the foot of the needle passer preferably contacts the exterior of the wall of the aorta which, due to the foot being larger than the aortotomy, serves to prevent blood leakage despite displacement of the tissue contacting member 614. After the needles and suture have been passed through the tissue, the needle passer is removed and the tissue contacting member 614 is pulled into contact with the wall of the aorta, thereby taking over the task of preventing leakage through the aortotomy.

Next, the shaft of the delivery device, sealing element and vascular conduit (not shown—but each of which is hollow) are slid down the suture and over the member 612 into contact with the wall of the aorta. The delivery device is then removed and the suture secured to anastomose the vascular conduit to the aorta. The shaft 620 may then be inserted through the vascular conduit and the member 612 pulled to collapse the tissue contacting member into the shaft. The shaft 620 and members 612, 614 may then be removed from the vascular conduit. Alternatively, the member 612 could simply be moved to the side and the vascular conduit anastomosed to the aorta. The shaft 620 could be used to collapse and withdraw the member 614 just before securing the final suture(s), and after such removal the anastomosis can be completed.

It will be appreciated that the device comprising member 612 and tissue contacting member 614 may be used to perform other procedures on a hollow body structure through which fluid is flowing. For example, the anastomosis could be performed by hand-suturing rather than with a needle passer. In addition, it will be recognized that other configurations may be used. For example, the tissue contacting member could be umbrella-shaped to that only the peripheral edge thereof contacts the tissue upon being moved into the expanded orientation, the member forming a working space between its interior and the interior surface of the hollow body structure. The tissue contacting member 614 may be formed of any suitable blood compatible, non-thrombogenic material, while the support member 612 may be formed of any suitable material such as those used for guidewires.

Many variations and modifications of the devices and methods disclosed herein will be readily apparent to persons skilled in the art. As such, it should be understood that the foregoing detailed description of preferred embodiments is made for purposes of setting forth a clear and complete disclosure, and is not intended to limit the scope of the invention which is defined by the claims which follow.

What is claimed is:

1. A device for passing at least one needle through tissue, the device comprising:
   a handle;
   a shaft assembly including a shaft movably coupled to the handle, at least one needle removably supported by the shaft and movable between radially extended and non-extended positions, and a protective cover overlying at least a portion of the shaft and needle when the needle is in said radially non-extended position, the cover being movable with respect to the shaft to allow the needle to move to said radially extended position, the shaft assembly having a ram slidably disposed over the shaft for moving the needle into said radially extended position, the protective cover being slidably disposed over the ram; and
   an actuator assembly operable using one hand for moving the cover to allow the needle to assume said radially extended position and moving the shaft to pass the needle through the tissue, the actuator assembly having a linkage coupled to a movable component, and movement of the movable component drives the linkage and moves the protective cover to allow the needle to assume said radially extended position, moves the ram to force the needle into said radially extended position, and moves the shaft to pass the needle through the tissue.

2. The device of claim 1, wherein the shaft comprises a solid rod, the ram comprises a first sleeve coaxially disposed over the solid rod, and the protective cover comprises a second sleeve coaxially disposed over the first sleeve.

3. The device of claim 1, wherein the shaft has proximal and distal ends, and the needle is supported at the distal end of the shaft.

4. A device for passing at least one needle through tissue, the device comprising:
   a handle;
   a shaft assembly including a shaft movably coupled to the handle, at least one needle removably supported by the shaft and movable between radially extended and non-extended positions, and a protective cover overlying at least a portion of the shaft and needle when the needle is in said radially non-extended position, the cover being movable with respect to the shaft to allow the needle to move to said radially extended position;
   an actuator assembly operable using one hand for moving the cover to allow the needle to assume said radially extended position and moving the shaft to pass the needle through the tissue; and
   at least one length of suture having two ends, one end being secured to the needle and the other end being removably supported by the shaft assembly.

5. The device of claim 4, wherein a first plurality of needles are removably supported adjacent the distal end of the shaft, and wherein one end of each of a plurality of lengths of sutures is secured to one of the needles, while the other end of each length of suture is removably supported by the shaft assembly.

6. The device of claim 5, further comprising a suture supporting member disposed on the shaft assembly, wherein the other end of each length of suture is removably supported by the suture supporting member.

7. The device of claim 6, wherein the suture supporting member comprises an inner sleeve having channels each of which receives a length of suture, and an outer tube disposed around the inner sleeve to enclose each length of suture in one of said channels.

8. The device of claim 6, wherein the suture supporting member is fixed to the handle assembly and has a distal end provided with a foot for contacting the tissue.

9. The device of claim 8, wherein the foot has a plurality of slots receiving the lengths of suture and the needles after the needles have passed through the tissue.

10. The device of claim 5, further comprising a second plurality of needles each of which is secured to the other end of one of the lengths of suture, wherein each of the second plurality of needles is removably supported by the shaft assembly.

11. The device of claim 1, further comprising a needle guard disposed around the needle when the needle is in said radially extended and non-extended positions.

12. The device of claim 11, wherein the needle guard comprises a cage disposed around the needle and movable between expanded and collapsed orientations.

13. A device for passing at least one needle through tissue, the device comprising:
a handle;
a shaft assembly including a shaft movably coupled to the handle, at least one needle removably supported by the shaft and movable between radially extended and non-extended positions, and a protective cover overlying at least a portion of the shaft and needle when the needle is in said radially non-extended position, the cover being movable with respect to the shaft to allow the needle to move to said radially extended position; and
an actuator assembly operable using one hand for moving the cover to allow the needle to assume said radially extended position and moving the shaft to pass the needle through the tissue;
a needle oguard disposed around the needle when the needle is in said radially extended and non-extended positions, the needle guard having a cage disposed around the needle and movable between expanded and collapsed orientations,
the cage having a plurality of flexible struts having one end secured to the shaft and another end secured to a ram slidably disposed over the shaft, wherein sliding the ram with respect to the shaft moves the needle into said radially extended position and moves the cage into said expanded orientation.

14. A device for passing at least one needle through tissue, the device comprising:
a handle assembly which is generally pistol shaped;
a shaft assembly including a shaft movably coupled to the handle, at least one needle removably supported by the shaft and movable between radially extended and non-extended positions, and a protective cover overlying at least a portion of the shaft and needle when the needle is in said radially non-extended position, the cover being movable with respect to the shaft to allow the needle to move to said radially extended position; and
an actuator assembly operable using one hand for moving the cover to allow the needle to assume said radially extended position and moving the shaft to pass the needle through the tissue, the actuator assembly having a trigger slidably mounted on the handle assembly.

15. The device of claim 14, wherein the trigger is movable in one direction to move the cover and the shaft, and the actuator assembly is provided with a mechanism preventing movement of the trigger in a different direction.

16. The device of claim 1, wherein the shaft assembly is substantially straight over the length thereof.

17. A device for passing at least one needle through tissue, the device comprising:
a handle;
a shaft assembly including a shaft movably coupled to the handle, at least one needle removably supported by the shaft and movable between radially extended and non-extended positions, and a protective cover overlying at least a portion of the shaft and needle when the needle is in said radially non-extended position, the cover being movable with respect to the shaft to allow the needle to move to said radially extended position the shaft assembly having a proximal portion adjacent the handle assembly and a distal portion, and the distal portion being angled with respect to the proximal portion; and
an actuator assembly operable using one hand for moving the cover to allow the needle to assume said radially extended position and moving, the shaft to pass the needle throuoh the tissue.

18. A device for passing a plurality of needles and a plurality of separate lengths of suture through tissue in a patient's body, the device comprising:
a handle;
a shaft assembly supporting a plurality of needles and a plurality of separate lengths of sutures, the shaft assembly having a distal portion configured to be positioned adjacent tissue of a patient's body through which the needles are to be passed, wherein the needles are located adjacent the distal portion of the shaft assembly and are movable between an extended position and a non-extended position, and one end of each length of suture is secured to one of the needles and the other end of each length of suture is located away from the needles; and
an actuator assembly operable to pass the needles through tissue.

19. The device of claim 18, wherein the shaft assembly includes a shaft to which the needles are mounted so as to be movable in a radial direction between said extended and non-extended positions, and the actuator is operable to move the shaft and pass the needles through tissue.

20. The device of claim 19, wherein the shaft assembly comprises a ram slidably disposed over the shaft for moving the needles into said radially extended position, and a protective cover slidably disposed over the ram.

21. The device of claim 20, wherein actuation of the actuator assembly moves the protective cover in a first direction, moves the ram in a second direction to force the needles into said radially extended position, and moves the shaft in said first direction to pass the needles through the tissue.

22. The device of claim 21, wherein the ram comprises a solid rod with individual portions each con-esponding to one of the needles, and the actuator assembly moves the individual portions of the ram in unison to force the needles into said radially extended position at the same time.

* * * * *